United States Patent
Nigam et al.

(10) Patent No.: US 10,691,220 B2
(45) Date of Patent: Jun. 23, 2020

(54) METHOD FOR DISPLAY OF INFORMATION FROM REAL WORLD ENVIRONMENT ON A VIRTUAL REALITY (VR) DEVICE AND VR DEVICE THEREOF

(71) Applicant: SAMSUNG ELECTRONICS CO., LTD., Suwon-si (KR)

(72) Inventors: Varun Nigam, Kanpur (IN); Veenu Pandey, Delhi (IN)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/896,732

(22) Filed: Feb. 14, 2018

(65) Prior Publication Data
US 2018/0232056 A1     Aug. 16, 2018

(30) Foreign Application Priority Data

Feb. 14, 2017     (IN) .............................. 201711005259

(51) Int. Cl.
| | | |
|---|---|---|
| G09G 5/00 | (2006.01) | |
| G06F 3/01 | (2006.01) | |
| G06F 3/16 | (2006.01) | |
| G06T 19/00 | (2011.01) | |
| A61B 5/16 | (2006.01) | |
| A61B 5/08 | (2006.01) | |
| A61B 5/024 | (2006.01) | |
| A61B 5/021 | (2006.01) | |
| A61B 5/01 | (2006.01) | |

(52) U.S. Cl.
CPC ............. *G06F 3/017* (2013.01); *G06F 3/011* (2013.01); *G06F 3/012* (2013.01); *G06F 3/013* (2013.01); *G06F 3/16* (2013.01); *G06F 3/167* (2013.01); *G06T 19/006* (2013.01); *A61B 5/01* (2013.01); *A61B 5/021* (2013.01); *A61B 5/024* (2013.01); *A61B 5/0816* (2013.01); *A61B 5/163* (2017.08); *G06F 2203/011* (2013.01); *G06T 2215/16* (2013.01)

(58) Field of Classification Search
CPC ................. G09G 5/14; G09G 2340/10; G09G 2340/125; G06T 11/60; G06T 15/503
USPC ....................................................... 345/629
See application file for complete search history.

(56) References Cited

U.S. PATENT DOCUMENTS

| | | | | |
|---|---|---|---|---|
| 2013/0293723 | A1* | 11/2013 | Benson ................ | G02B 27/017 348/164 |
| 2013/0335301 | A1* | 12/2013 | Wong ................. | G02B 27/0093 345/8 |
| 2016/0026381 | A1* | 1/2016 | Kim ..................... | G06F 3/04817 715/761 |
| 2016/0241836 | A1* | 8/2016 | Cole .................... | H04N 19/597 |
| 2017/0358141 | A1* | 12/2017 | Stafford ............... | G02B 27/017 |
| 2018/0093185 | A1* | 4/2018 | Black ................... | A63F 13/537 |

* cited by examiner

*Primary Examiner* — Gordon G Liu
(74) *Attorney, Agent, or Firm* — Sughrue Mion, PLLC

(57) ABSTRACT

The present invention relates to method (1100) for display of information from real world environment on a virtual reality (VR) device (101). In accordance with one embodiment, the method comprises capturing (1101) an event in a real world environment; and presenting (1103) information pertaining to the captured event on a VR enabled display unit (106) without absolute interruption of an ongoing rendering of content on the VR enabled display unit (106), if the event thus captured satisfies at least one predetermined rule.

18 Claims, 38 Drawing Sheets

METHOD FOR DISPLAY OF INFORMATION FROM REAL WORLD ENVIRONMENT ON A VIRTUAL REALITY (VR) DEVICE AND VR DEVICE THEREOF

CROSS-REFERENCE TO RELATED APPLICATION(S)

This application is based on and claims priority under 35 U.S.C. § 119 to Indian Patent Application No. 201711005259, filed on Feb. 14, 2017, in the Indian Intellectual Property Office, the disclosure of which is incorporated by reference herein in its entirety.

TECHNICAL FIELD

The present invention generally relates to virtual reality (VR). More particularly, the invention relates to display of information from real world environment on a VR device.

BACKGROUND

With advancement in technology, virtual reality technologies are gaining popularity. Virtual reality (VR) technologies refer to generation of a three-dimensional image or video of a real world environment with which a user can interact using a VR device. In one implementation, such VR device can be a standalone device having VR processing and VR rendering capabilities. In another implementation, a user may wear a VR device to enjoy a VR experience, wherein the VR device comprises a smart phone mounted in a secure manner in a mounting unit provided in a head mounted device (HMD), wherein the smart phone faces lenses of the HMD.

VR devices have been proposed for providing a variety of virtual reality based experience to a wearer such that the wearer is immersed in the virtual reality. However, such VR devices lead to reducing the wearer's ability to sense the real world environment. In one such example, the wearer may not be able to identify stairs. In another such example, the wearer may not be able to identify a speeding car. In one another such example, the wearer may not be able to hear someone calling the wearer or someone knocking at the door.

Additionally, the wearer has to remove the VR device to view and/or interact with the real world environment. However, such removal causes discomfort as the wearer has to perform manual activities, leading to poor user experience. Further, such frequent removals lead to discontinuity in VR experience, thereby further resulting poorer user experience.

Thus, there exists a need for a solution to overcome above-mentioned deficiencies and enable display of information from real world environment while the wearer continues having VR experience.

SUMMARY OF THE INVENTION

This summary is provided to introduce a selection of concepts in a simplified format that are further described in the detailed description of the invention. This summary is not intended to identify key or essential inventive concepts of the claimed subject matter, nor is it intended for determining the scope of the claimed subject matter.

In accordance with the purposes of the invention, the present invention as embodied and broadly described herein, provides for displaying of information from real world environment on a virtual reality (VR) device.

To this end, an event is captured in a real world environment. If the event thus captured satisfies at least one predetermined rule, information pertaining to the captured event is presented on a VR enabled display unit. Such information is presented without absolute interruption of an ongoing rendering of VR content on the VR enabled display unit.

The advantages of the invention include, but not limited to, enabling viewing of events/incidents happening in the real world environment while continuing having VR experience. This eliminates a need for physically removing the VR device. In addition, a user can perform multitasking while viewing the VR content by simultaneously viewing VR content and information from the real world environment without any discomfort or hassle of manual switching. Further, physical harm or external risks can be quickly identified and presented on the VR device without interrupting the VR experience. Each of the above aspect contributes to considerably improving user-experience.

These aspects and advantages will be more clearly understood from the following detailed description taken in conjunction with the accompanying drawings and claims.

BRIEF DESCRIPTION OF THE ACCOMPANYING DRAWINGS

To further clarify advantages and aspects of the invention, a more particular description of the invention will be rendered by reference to specific embodiments thereof, which is illustrated in the appended drawings. It is appreciated that these drawings depict only typical embodiments of the invention and are therefore not to be considered limiting its scope. The invention will be described and explained with additional specificity and detail with the accompanying drawings, which are listed below for quick reference.

Figure 3A:
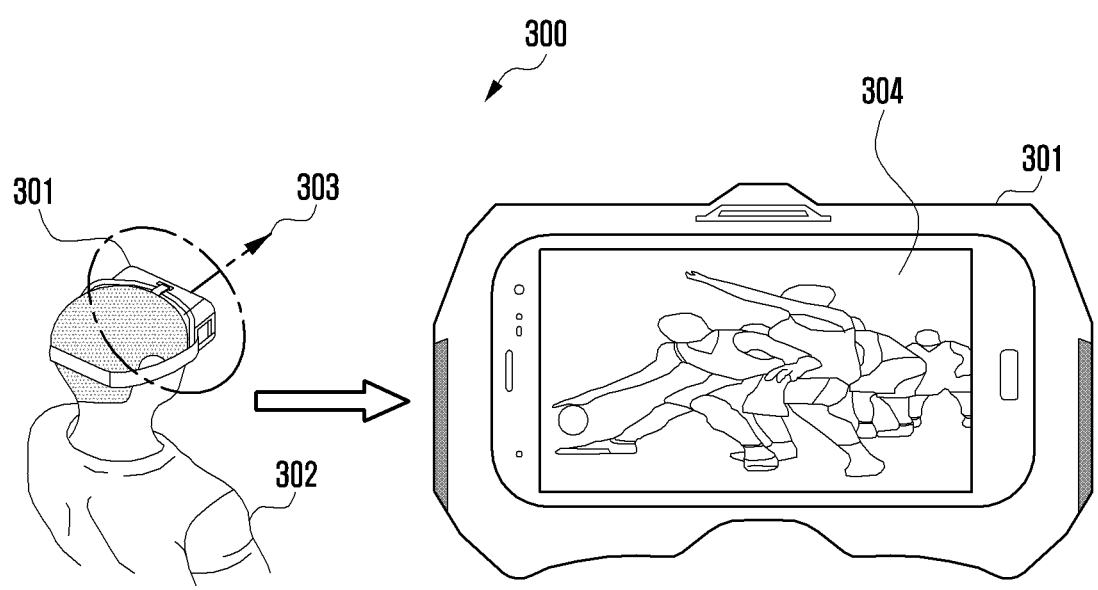
Figure 3B:
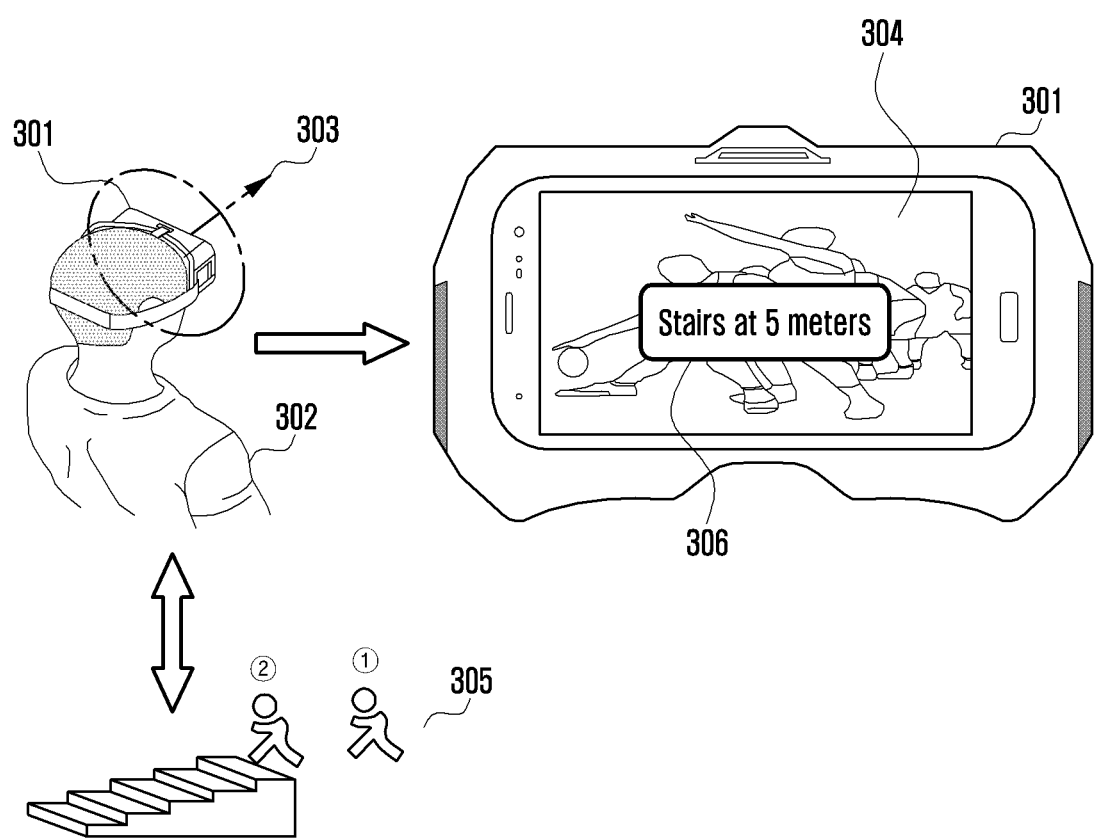
Figure 3C:
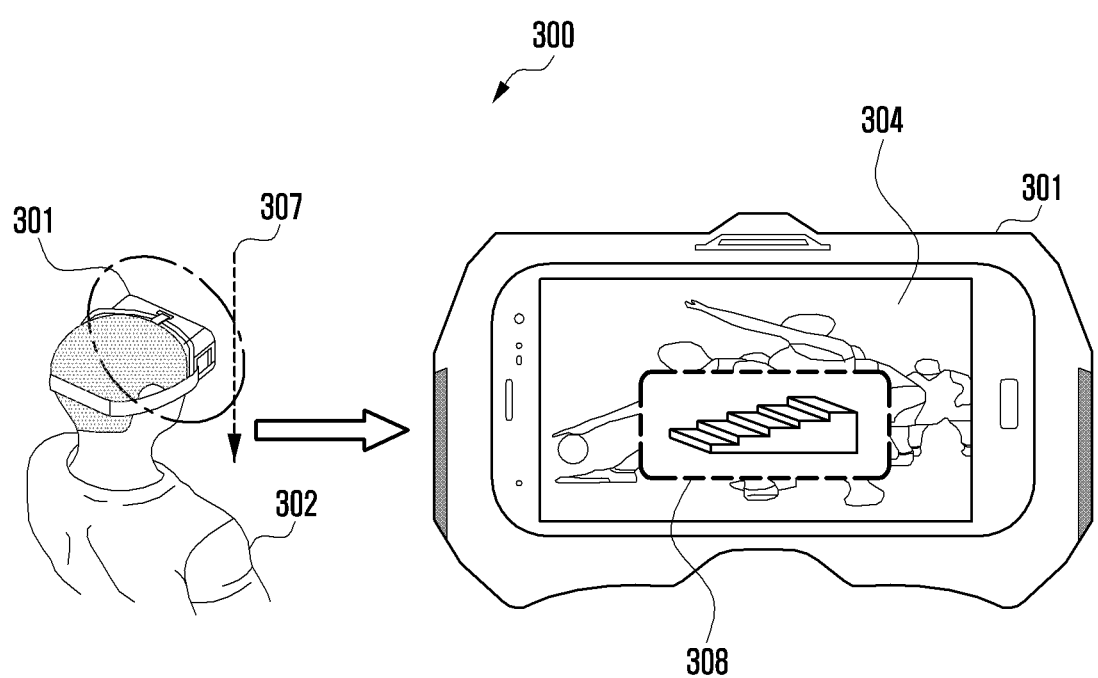

FIGS. 3A, 3B, and 3C illustrate first example of displaying of information from real world environment on a VR device, in accordance with an embodiment of the present invention.

FIGS. 4A, 4B, 4C, and 4D illustrate second example of displaying of information from real world environment on a VR device, in accordance with an embodiment of the present invention.

FIGS. 5A, 5B, 5C, and 5D illustrate third example of displaying of information from real world environment on a VR device, in accordance with an embodiment of the present invention.

FIGS. 6A, 6B, 6C, and 6D illustrate fourth example of displaying of information from real world environment on a VR device, in accordance with an embodiment of the present invention.

Figure 7A:
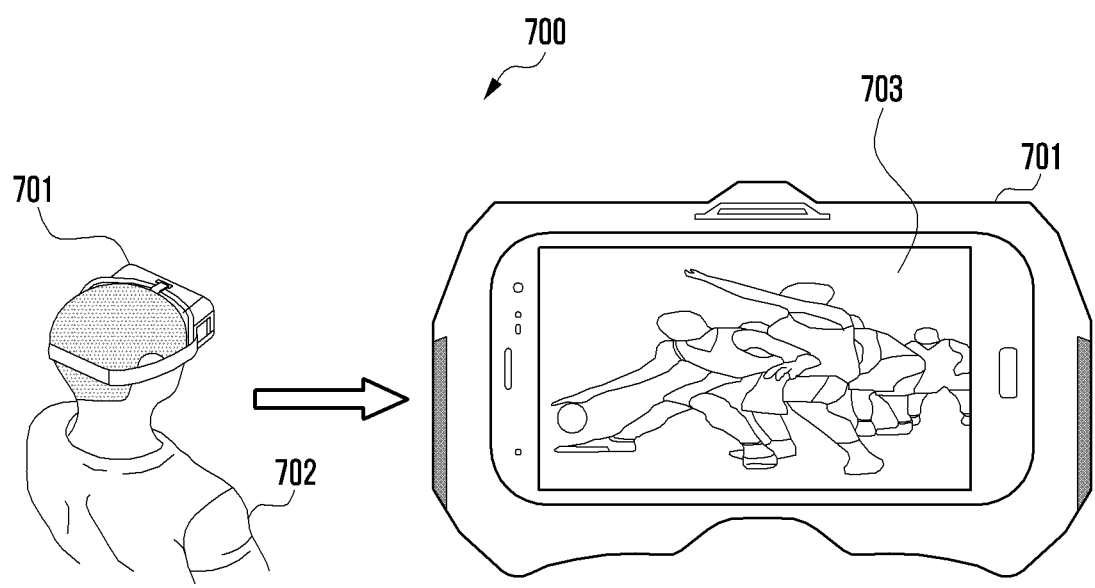
Figure 7B:
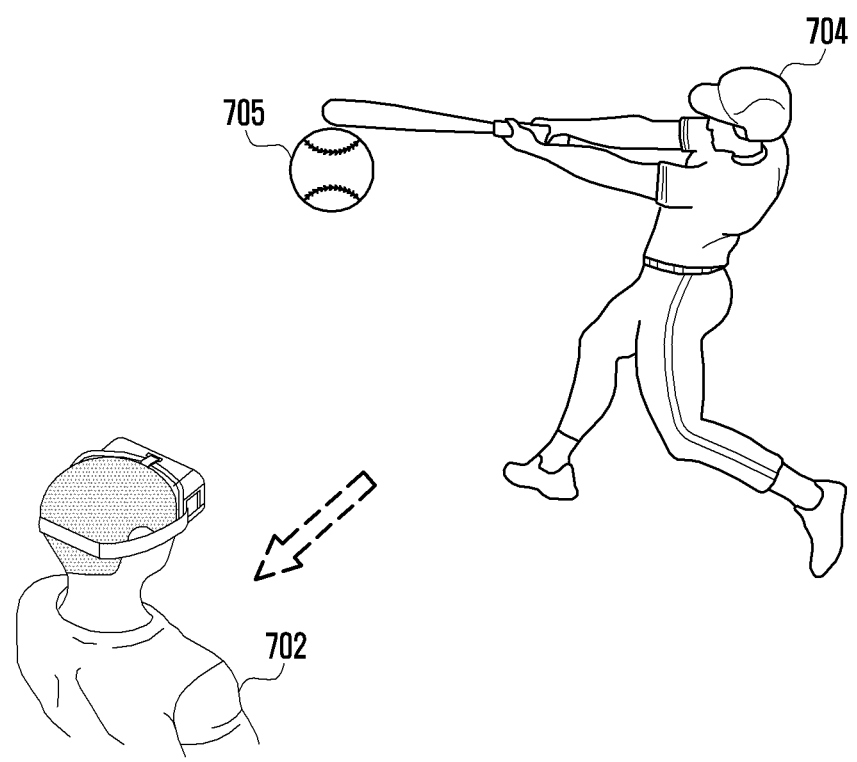
Figure 7C:
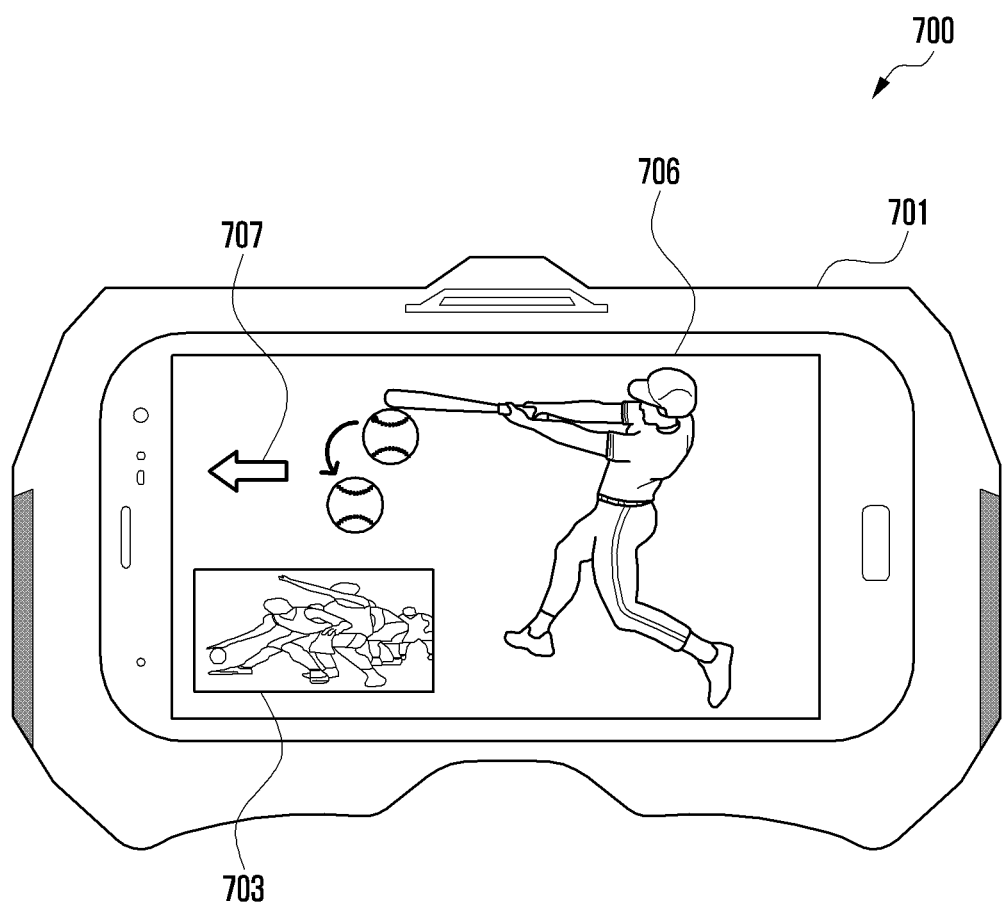

FIGS. 7A, 7B, and 7C illustrate fifth example of displaying of information from real world environment on a VR device, in accordance with an embodiment of the present invention.

FIGS. 8A, 8B, 8C, 8D, and 8E illustrate sixth example of displaying of information from real world environment on a VR device, in accordance with an embodiment of the present invention.

FIGS. 9A, 9B, 9C, 9D, 9E, and 9F illustrate seventh example of displaying of information from real world environment on a VR device and controlling presentation of the information based on user gestures, in accordance with an embodiment of the present invention.

Figure 10A:
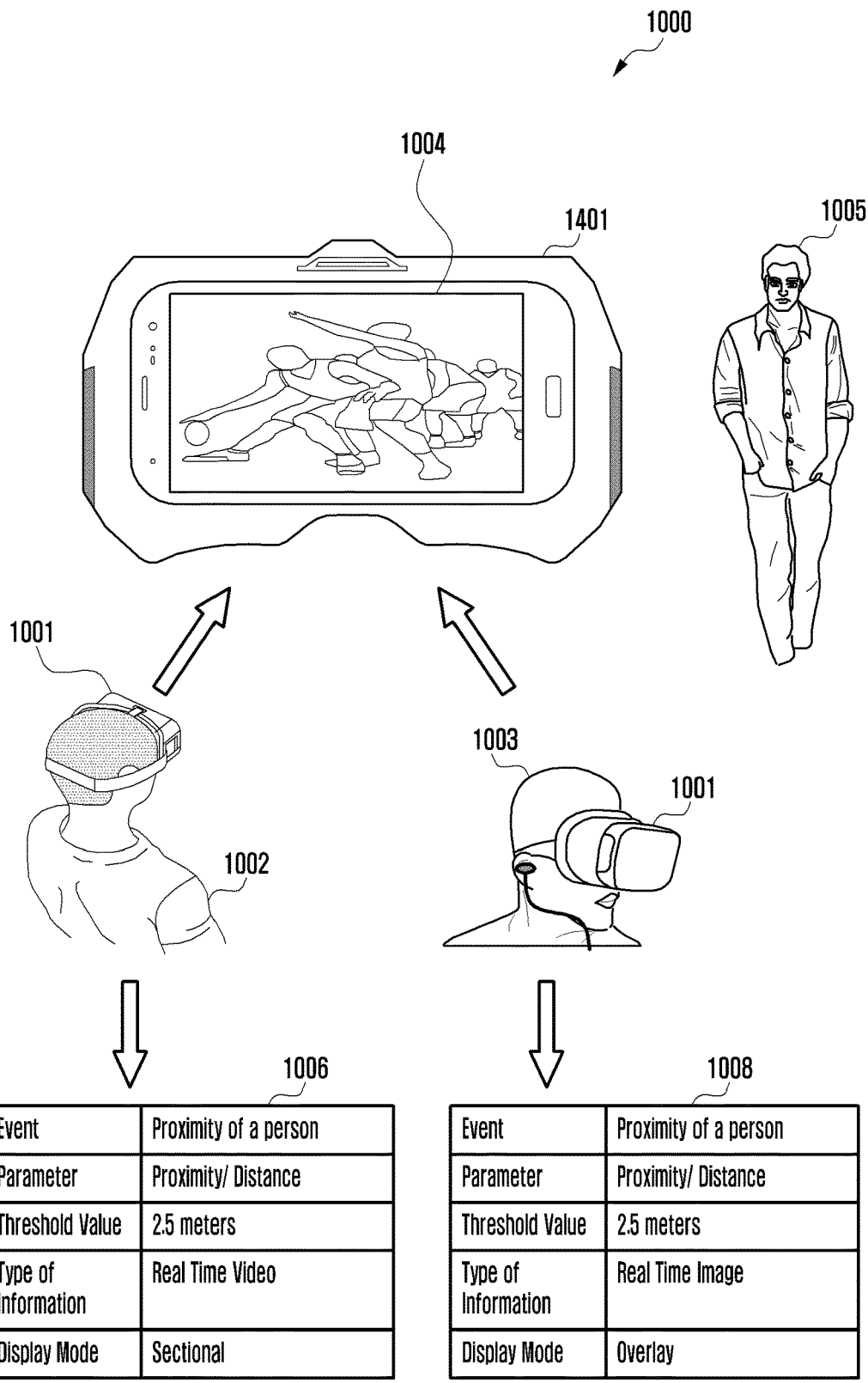
Figure 10B:
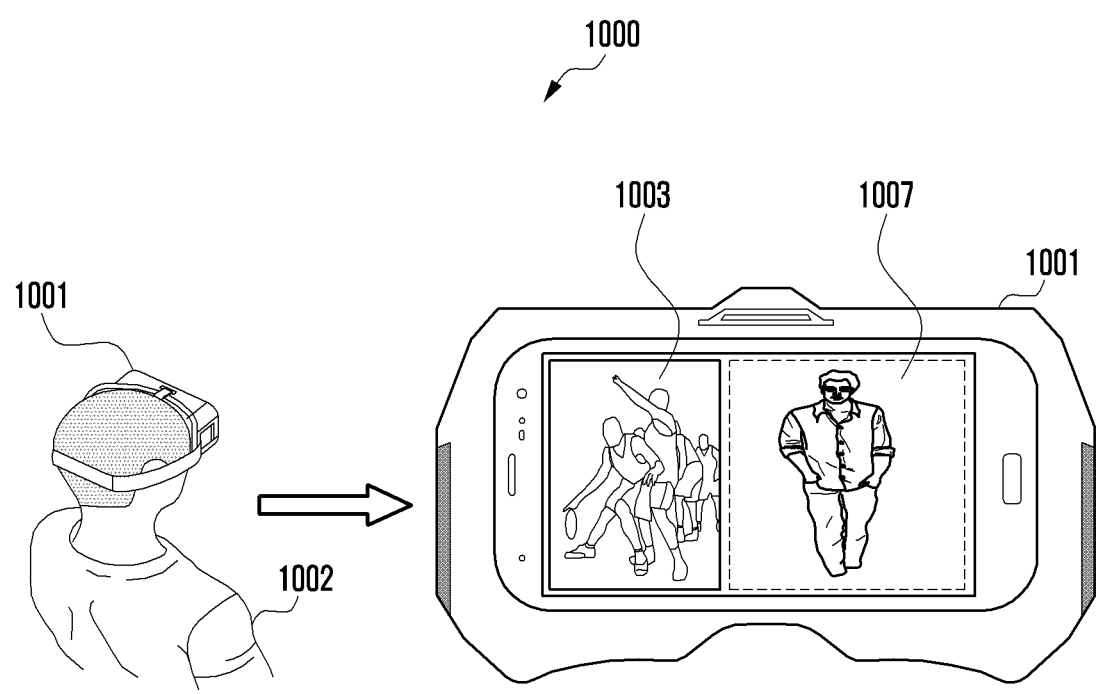
Figure 10C:
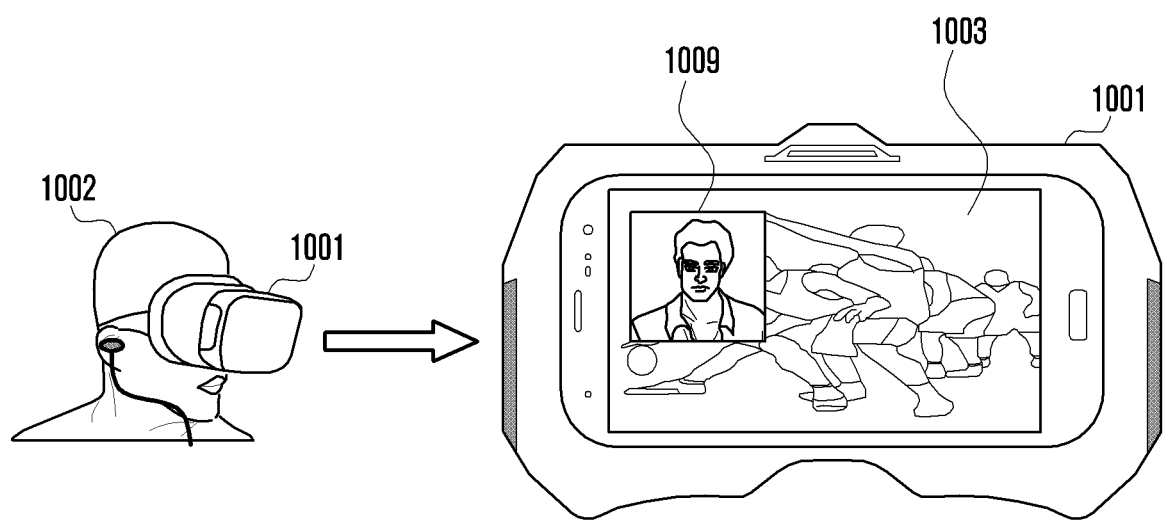

FIGS. 10A, 10B, and 10C illustrate eighth example of displaying of different information from real world environment on a VR device for different users, in accordance with an embodiment of the present invention.

Figure 11:
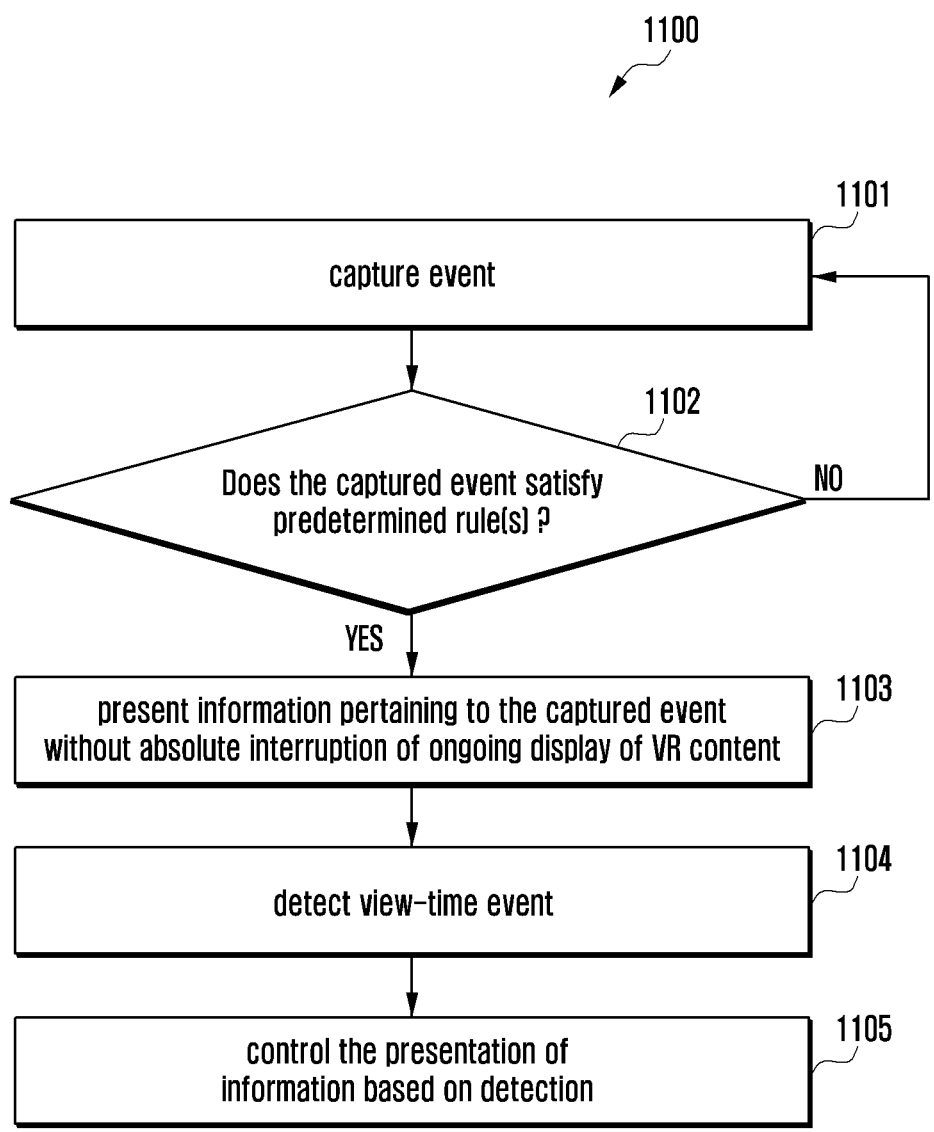

FIG. 11 illustrates an exemplary method for displaying of information from real world environment on a VR device, in accordance with an embodiment of the present invention.

Figure 12:
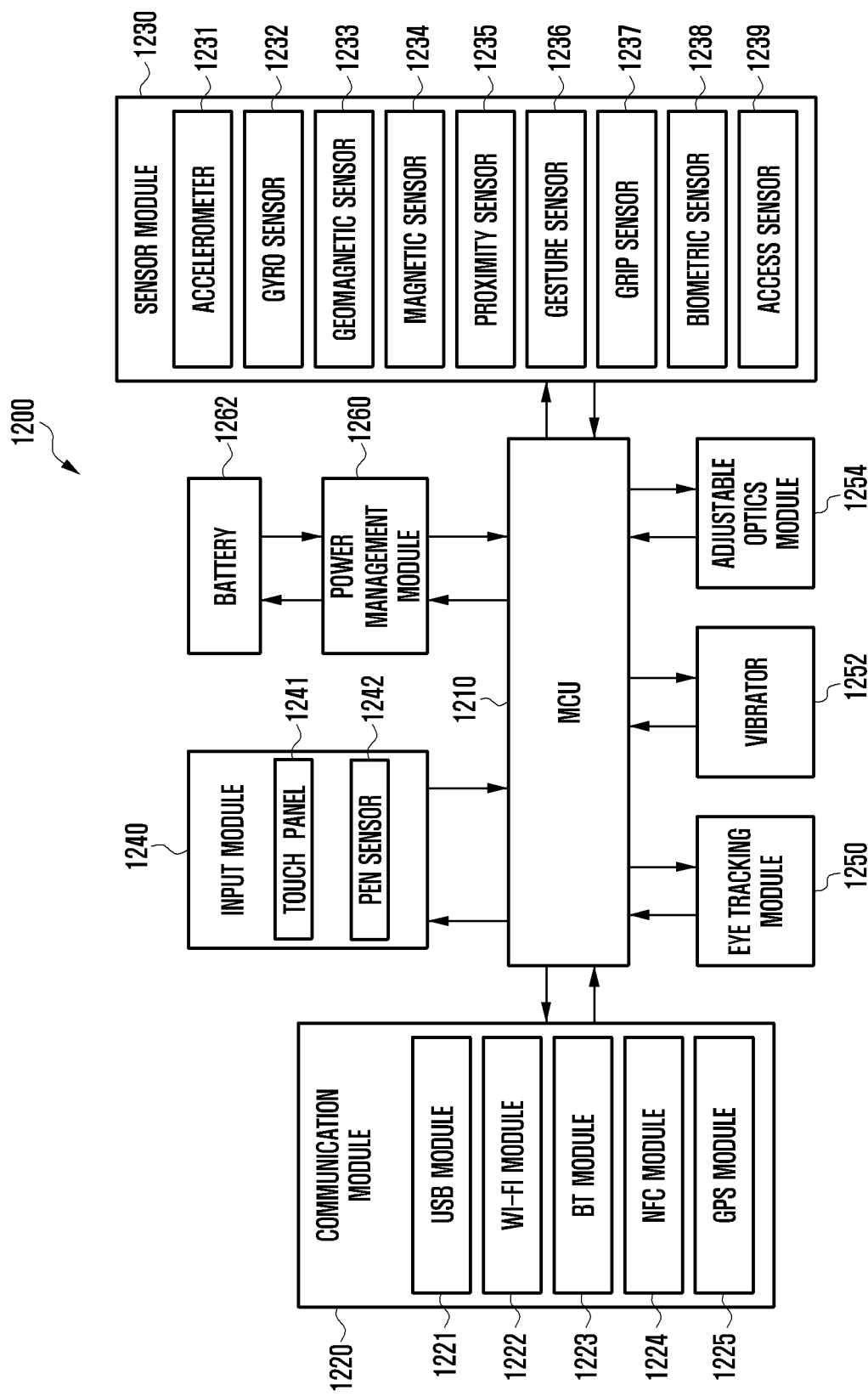

FIG. 12 illustrates a block diagram of a second electronic device according to an embodiment of the present invention.

Figure 13:
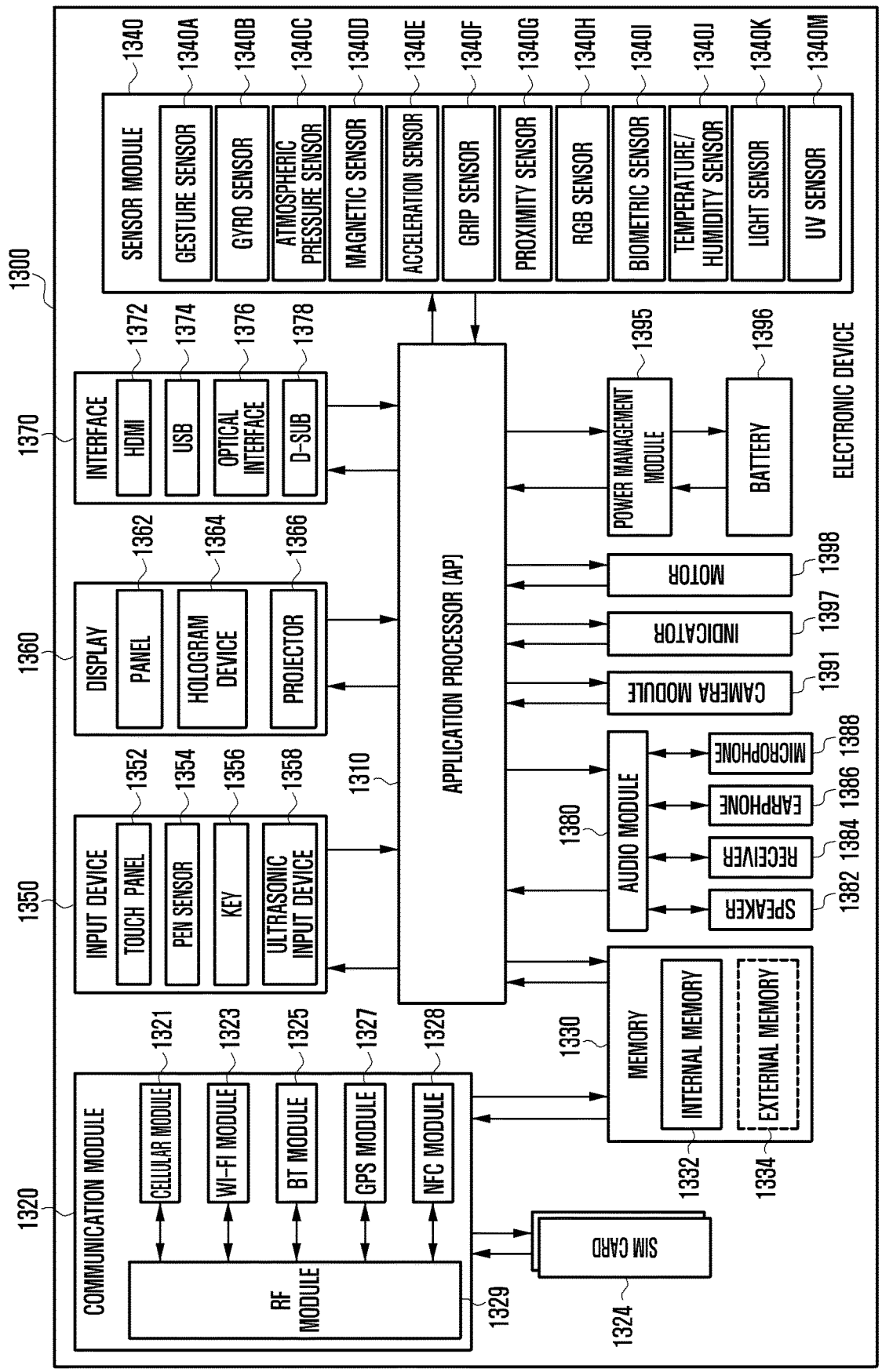

FIG. 13 illustrates a block diagram of a first electronic device according to various embodiments of the present invention or that includes an electronic device to which a method for displaying of information from real world environment on a VR device is applicable.

It may be noted that to the extent possible, like reference numerals have been used to represent like elements in the drawings. Further, those of ordinary skill in the art will appreciate that elements in the drawings are illustrated for simplicity and may not have been necessarily drawn to scale. For example, the dimensions of some of the elements in the drawings may be exaggerated relative to other elements to help to improve understanding of aspects of the invention. Furthermore, the one or more elements may have been represented in the drawings by conventional symbols, and the drawings may show only those specific details that are pertinent to understanding the embodiments of the invention so as not to obscure the drawings with details that will be readily apparent to those of ordinary skill in the art having benefit of the description herein.

DETAILED DESCRIPTION

It should be understood at the outset that although illustrative implementations of the embodiments of the present disclosure are illustrated below, the present invention may be implemented using any number of techniques, whether currently known or in existence. The present disclosure should in no way be limited to the illustrative implementations, drawings, and techniques illustrated below, including the exemplary design and implementation illustrated and described herein, but may be modified within the scope of the appended claims along with their full scope of equivalents.

The term "some" as used herein is defined as "none, or one, or more than one, or all." Accordingly, the terms "none," "one," "more than one," "more than one, but not all" or "all" would all fall under the definition of "some." The term "some embodiments" may refer to no embodiments or to one embodiment or to several embodiments or to all embodiments. Accordingly, the term "some embodiments" is defined as meaning "no embodiment, or one embodiment, or more than one embodiment, or all embodiments."

The terminology and structure employed herein is for describing, teaching and illuminating some embodiments and their specific features and elements and does not limit, restrict or reduce the spirit and scope of the claims or their equivalents.

More specifically, any terms used herein such as but not limited to "includes," "comprises," "has," "consists," and grammatical variants thereof do NOT specify an exact limitation or restriction and certainly do NOT exclude the possible addition of one or more features or elements, unless otherwise stated, and furthermore must NOT be taken to exclude the possible removal of one or more of the listed features and elements, unless otherwise stated with the limiting language "MUST comprise" or "NEEDS TO include."

Whether or not a certain feature or element was limited to being used only once, either way it may still be referred to as "one or more features" or "one or more elements" or "at least one feature" or "at least one element." Furthermore, the use of the terms "one or more" or "at least one" feature or element do NOT preclude there being none of that feature or element, unless otherwise specified by limiting language such as "there NEEDS to be one or more . . . " or "one or more element is REQUIRED."

Unless otherwise defined, all terms, and especially any technical and/or scientific terms, used herein may be taken to have the same meaning as commonly understood by one having an ordinary skill in the art.

Reference is made herein to some "embodiments." It should be understood that an embodiment is an example of a possible implementation of any features and/or elements presented in the attached claims. Some embodiments have been described for the purpose of illuminating one or more of the potential ways in which the specific features and/or elements of the attached claims fulfil the requirements of uniqueness, utility and non-obviousness.

Use of the phrases and/or terms such as but not limited to "a first embodiment," "a further embodiment," "an alternate embodiment," "one embodiment," "an embodiment," "multiple embodiments," "some embodiments," "other embodiments," "further embodiment", "furthermore embodiment", "additional embodiment" or variants thereof do NOT necessarily refer to the same embodiments. Unless otherwise specified, one or more particular features and/or elements described in connection with one or more embodiments may be found in one embodiment, or may be found in more than one embodiment, or may be found in all embodiments, or may be found in no embodiments. Although one or more features and/or elements may be described herein in the context of only a single embodiment, or alternatively in the context of more than one embodiment, or further alternatively in the context of all embodiments, the features and/or elements may instead be provided separately or in any appropriate combination or not at all. Conversely, any features and/or elements described in the context of separate embodiments may alternatively be realized as existing together in the context of a single embodiment.

Any particular and all details set forth herein are used in the context of some embodiments and therefore should NOT be necessarily taken as limiting factors to the attached claims. The attached claims and their legal equivalents can be realized in the context of embodiments other than the ones used as illustrative examples in the description below.

Figure 1A:
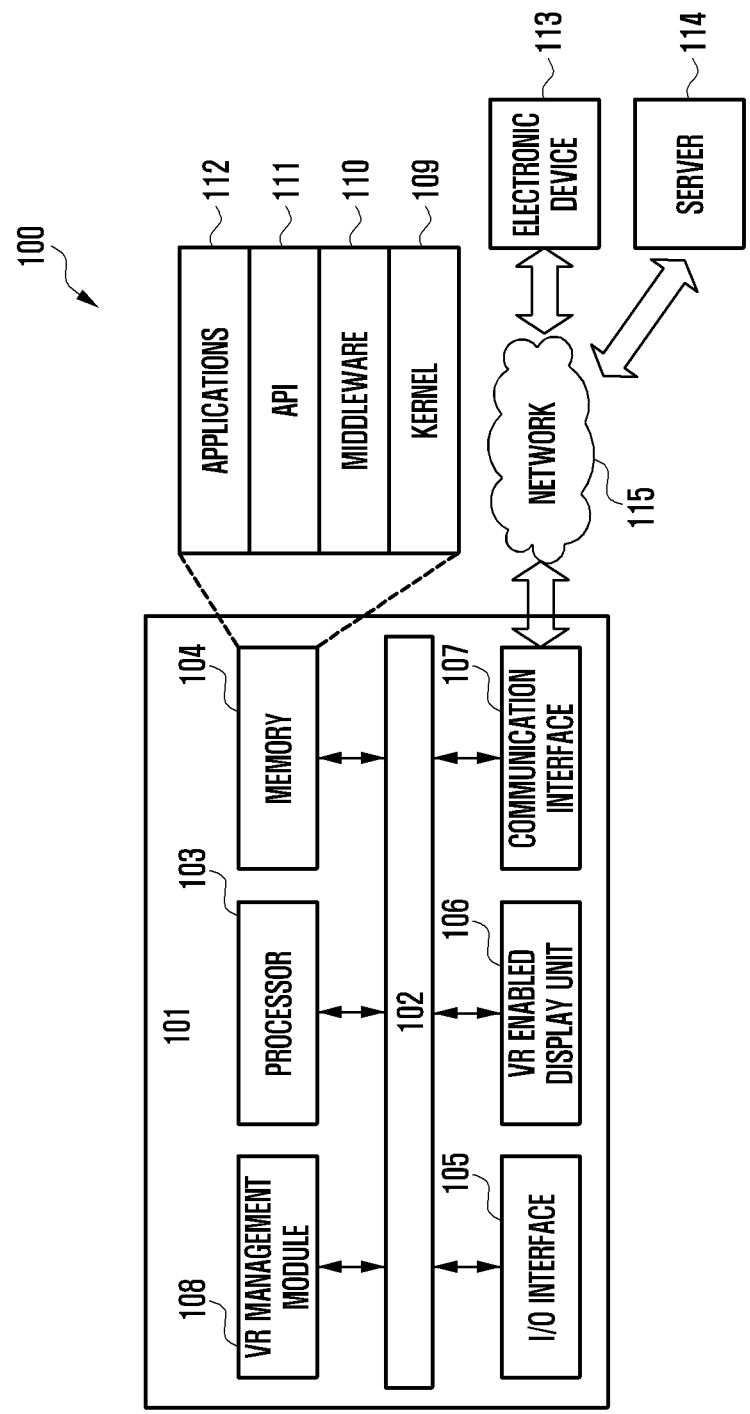
FIG. 1A is conceptual view illustrating a network environment that includes virtual reality (VR) device according to an embodiment of the present invention or that includes a VR device to which a method for displaying of information from real world environment is applicable.

FIG. 1A is a conceptual view illustrating a network environment that includes virtual reality (VR) device according to various embodiments of the present invention or that includes a VR device to which a method for displaying of information from real world environment is applicable.

Referring to FIG. 1A, a VR device 101 may include a bus 102, a processor 103, a memory 104, an input/output (I/O)

interface 105, a VR enabled display unit 106, a communication interface 107, and a virtual reality (VR) management module 108.

The bus 102 may be a circuit that connects the foregoing components and allows communication (for example, control messages) between the foregoing components.

The processor 103 may, for example, receive instructions from other components (for example, the memory 104, the I/O interface 105, the VR enabled display unit 106, or the communication interface 107), interpret the received instructions, and execute computation or data processing according to the interpreted instructions. The processor 103 may control one or more other components of the VR device 101 and/or processes an operation or data related to communication. The processor 103 may include one or more of a Central Processing Unit (CPU), an Application Processor (AP), and a Communication Processor (CP).

The memory 104 may, for example, store instructions or data that are received from, or generated by, other components (for example, the I/O interface 105, the VR enabled display unit 106, the communication interface 107, or the VR management module 108). For example, the memory 104 may include programming modules such as a kernel 109, a middleware 110, an application programming interface (API) 111, or an application 112. Each of the foregoing programming modules may include software, firmware, hardware, or a combination of at least two of software, firmware, and hardware.

The kernel 109 may control or manage system resources (for example, the bus 102, the processor 103, or the memory 104) that are used in executing operations or functions implemented in other programming modules such as the middleware 110, the API 111, or the application 112. In addition, the kernel 109 may provide an interface for allowing the middleware 110, the API 111, or the application 112 to access and control or manage individual components of the VR device 101.

The middleware 110 may be a medium through which the kernel 109 may communicate with the API 111 or the application 112 to transmit and receive data. In addition, the middleware 110 may perform control operations (for example, scheduling or load balancing) in regard to work requests by one or more applications 112 by, for example, assigning priorities for using system resources (the bus 102, the processor 103, or the memory 104) of the VR device 101 to the one or more applications 112.

The API 111 is an interface that may control functions that the application 112 provides at the kernel 109 or the middleware 110. For example, the API 111 may include at least one interface or function (for example, a command) for file control, window control, video processing, or text control.

According to various embodiments, the application 112 may include a short message service (SMS)/media messaging service (MMS) application, an email application, a calendar application, an alarm application, a health care application (for example, an application that measures the amount of exercise or a blood sugar level), or an environment information application (for example, an application that provides information about air pressure, humidity, or temperature). Alternatively or additionally, the application 112 may be an information exchange related application that allows for exchanging information between the VR device 101 and an external electronic device (for example, an electronic device 113). The information exchange-related application may be, for example, a notification relay application for transmitting specific information to the external electronic device or a device management application for managing the external electronic device.

For example, the notification relay application may include a function of transmitting notification information generated from another application (for example, an SMS/MMS application, an email application, a health care application, or an environment information application) to the external electronic device (for example, the electronic device 113). Alternatively or additionally, the notification relay application may receive notification information from the external electronic device (for example, the electronic device 113) and transmit the received notification information to a user. The device management application may manage (for example, install, delete, or update) at least a part of functions of the external electronic device (for example, the electronic device 113) communicating with the VR device 101 (for example, turn-on, turn-off of the external electronic device (or a part of its components) or control of the brightness (or resolution) of the display), an application executed in the external electronic device, or a service (for example, a call service or a message service) provided by the external electronic device.

According to various embodiments, the application 112 may include an application designated according to a property (for example, the type of the electronic device) of the external electronic device (for example, the electronic device 113). For example, if the external electronic device is a digital audio player, the application 112 may include an application related to music play. If the external electronic device is a mobile medical device, the application 112 may include an application related to health care. According to an embodiment, the application 112 may include at least one of an application designated in the VR device 101 or an application received from another electronic device (for example, a server 114 or the electronic device 113). The server 114 can be single server or may include a group of one or more servers.

Further, according to various embodiments of the present invention, another electronic device, or a plurality of electronic devices, such as the external electronic device 113 and the server 114, may perform some or all of the operations performed by the VR device 101. In one example, when the VR device 101 performs some functions or services automatically or by request, the VR device 101 may request the external electronic device 113 and the server 114 to perform at least some of the functions related to the functions or services, in addition to or instead of performing the functions or services by itself. In this case, external electronic device 113 and the server 114 may carry out the requested function or the additional function, and transfers the result to the VR device 101. The VR device 101 may provide the requested functions or services based on the received result as is or after additionally processing the received result. To this end, for example, cloud computing, distributed computing, or client-server computing technology may be used.

The I/O interface 105 may receive a command or data from a user through an I/O device (for example, a sensor, a keyboard, or a touch screen) to the processor 103, the memory 104, the communication interface 107, or the VR management module 108, for example, through the bus 102. For example, the I/O interface 105 may provide data of a user touch received through the touch screen to the processor 103. Further, the I/O interface 105 may, for example, output a command or data received from the processor 103, the memory 104, the communication interface 107, or the VR management module 108 through the bus 102 to the I/O device (for example, a speaker or a display). For example, the I/O interface 105 may output voice data processed by the processor 103 to a user through the speaker.

The VR enabled display unit 106 may display various types of information (for example, multimedia data or text data) to the user. The VR enabled display unit 106 may be configured to include, but not limited to, a liquid crystal display (LCD), a light emitting diode (LED) display, an organic LED (OLED) display, a plasma cell display, an electronic ink array display, an electronic paper display, a flexible LCD, a flexible electro-chromic display, and a flexible electro wetting display.

The communication interface 107 may provide communication between the VR device 101 and an external device (for example, the electronic device 113 or the server 114). For example, the communication interface 107 may be connected to a network 115 by wireless or wired communication and communicate with the external device over the network 115. The wireless communication may be conducted in conformance to, for example, at least one of wireless fidelity (WiFi), Bluetooth (BT), near field communication (NFC), GPS, and cellular communication (for example, long term evolution (LTE), LTE-Advanced (LTE-A), code division multiple access (CDMA), Wideband CDMA (WCDMA), universal mobile telecommunication system (UMTS), wireless broadband (WiBro), or global system for mobile communications (GSM)). The wired communication may be conducted in conformance to, for example, at least one of universal serial bus (USB), high definition multimedia interface (HDMI), Recommended Standard 232 (RS-232), or plain old telephone service (POTS).

According to an embodiment, the network 115 may be a communication network, for example, at least one of a computer network, the Internet, an Internet of things (IoT), and a telephone network. According to an embodiment, at least one of the application 112, the API 111, the middleware 110, the kernel 109, or the communication interface 107 may support a protocol (for example, a transport layer protocol, a data link layer protocol, or a physical layer protocol) for communication between the VR device 101 and the external device 113.

According to an embodiment of the present invention, the VR device 101 displays information from real world environment. Thus, the VR management module 108 may perform for example, an operation to capture an event in a real world environment and an operation to present information pertaining to the captured event on the VR enabled display unit 106 if the event satisfies at least one predetermined rule.

Figure 1B:
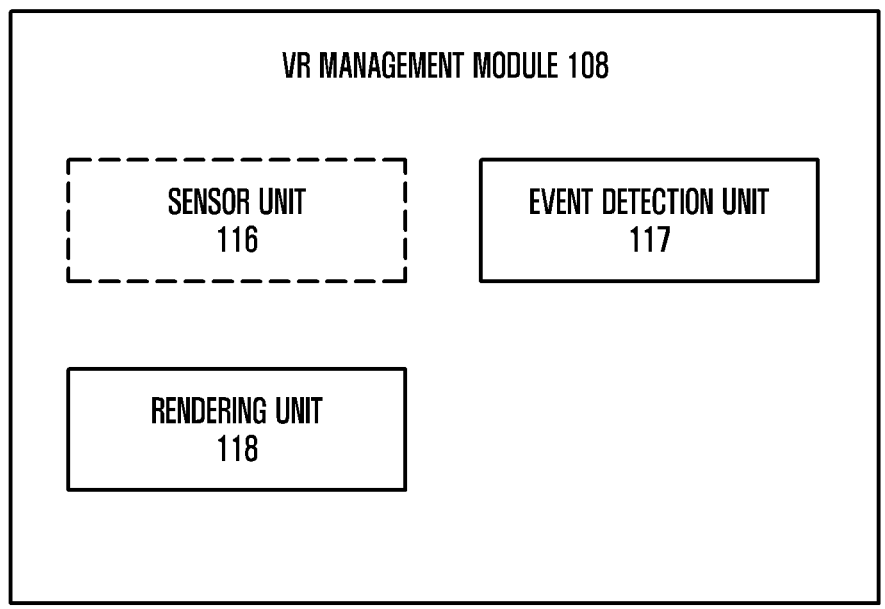
FIG. 1B illustrates a block diagram of a VR management module in the VR device according to an embodiment of the present invention.

Referring to FIG. 1B, a block diagram of the VR management module 108 in the VR device 101 is illustrated according to the embodiment of the present invention to perform various operations as mentioned above. The VR management module 108 includes a sensor unit 116, an event detection unit 117, and a rendering unit 118.

In one implementation, the event detection unit 117 and the rendering unit 118 can be software modules. In one implementation, the event detection unit 117 and the rendering unit 118 can be hardware modules. In one implementation, the event detection unit 117 and the rendering unit 118 can be combination of software and hardware modules. In one implementation, a single unit can perform functions of any combination of the units from the event detection unit 117 and the rendering unit 118.

In accordance with the present invention, the sensor unit 116 captures an event in a real world environment. Examples of the real world environment include, but not limited to, home, various rooms in home, vehicle, office, theatre, museum, park, and other buildings. In one implementation, the sensor unit 116 captures the event from the real world environment continuously. In one implementation, the sensor unit 116 captures the event from the real world environment periodically. The event corresponds to a change within a predefined area in the real world environment surrounding the VR device 101. The event can be related to a person or object or any external device near the VR device 101.

In one implementation, the event is a risk or a threat to a user/wearer of the VR device 101 (hereinafter referred to as VR user). In one example of such implementation, the risk can be user falling of stairs while being immersed in virtual reality. In another example of such implementation, the risk can be the user missing a speeding car towards himself while being immersed in virtual reality.

In one implementation, the event is a gesture input. In one example, the gesture input is from the VR user. In one example, the gesture input is from a secondary person present within a field of view of the sensor unit 116.

In one implementation, the event is an audio input. In one example, the audio input is audio/voice of the VR user. In one example, the audio input is audio/voice of a secondary person proximate to the sensor unit 116. In one example, the audio input is notification sound generated by a device. Example of the sound can be ringtones, bell sound, chimes, alarm, beep, tones, speech notification, buzzer, warning, announcement, etc. Examples of the device can be, clock, warning systems/device, announcement systems/device, digital home appliances such as TV, washing machine, speakers, music system, and home theatre system, mobile devices such as notebook, laptop, and mobile phone, connected electronic devices such as Internet of Things (IoT) devices. In one example, the audio input is a sound generated in the real world environment such as crashing/clashing of objects, honking from a vehicle, and thundering.

In one implementation, the event is an eye gaze movement. In one example, eye gaze movement is related to a secondary user watching/gazing at the VR user.

In one implementation, the event is a facial expression of a person proximate to the VR device 101. Examples of such facial expression can include, but not limited to, anxiety, surprise, panic, happy, etc. In one example, a secondary user can have facial expression of 'awesome' upon watching the VR user cycling while being immersed in virtual reality.

In one implementation, the event is movement of the VR device 101. In one example, the VR user while wearing the VR device is by moving his head to look down on table to see a plate of fruits. Such movement of head results in movement of the VR device.

In one implementation, the event is proximity of a person to the VR device 101. In one implementation, the event is proximity of an object to the VR device 101. In one implementation, the event is a sudden movement in proximity to the VR device 101.

In one implementation, the event is a physiological state of the user of the VR device. Examples of the physiological state include, but not limited to, neutral, anxiety, sleepy, anger, fear, sadness, happiness, physical stress, emotional stress, disgust, etc.

Further, the sensor unit 116 comprises an eye-tracing sensor, a facial expression sensor; a touch panel; a vibrator; an optics module; an accelerometer; a gyroscope; a geo-magnetic sensor; a magnetic sensor; a proximity sensor; a gesture sensor; a grip sensor; a biometric sensor; an access sensor; a camera module; an audio module; an atmospheric pressure sensor; RGB sensor; temperature sensor; humidity sensor; light sensor; physiological sensor; location/position detection sensor; and UV sensor. Examples of the camera module include, but not limited to, 3D camera, depth camera, and infrared camera. In one example implementation, the sensor unit 116 is integral to the VR device 101, as illustrated in the figure. In such implementation, the VR device 101 is a standalone device having VR processing and VR rendering capabilities. In another example implementation, the sensor unit 116 is external to the VR device 101 and is preferably coupled to the VR device 101 as an external electronic device. Example of such external electronic device is a Head Mounted Device (HMD), which is coupled with a smart phone (or VR device). In one another example implementation, the sensor unit 116 is part of an external electronic device communicatively coupled with the VR device 101. Examples of such external electronic device include, but not limited to, wearable devices such as wrist band, smart watches, fitness/health trackers, smart rings/bracelets, smart gloves, etc., weather sensor, cameras such as 3D camera, depth camera, infrared camera, etc., flame sensors, smoke sensors, etc.

Additionally, the sensor unit 116 may obtain at least one parameter associated with the event. In one example, the event is proximity of a person to the VR device 101. In such example, parameter associated with the event can be distance/proximity of the person from the VR device 101. In another example, the event is proximity of an object to the VR device 101. In such example, parameters associated with the event can be distance/proximity of the object from the VR device 101, speed of the object, and direction of the object. In another example, the event is physiological state of the user. In such example, parameters associated with the event can include, but not limited to, blood pressure, heartbeat, body temperature, sweat, respiration rate, perspiration rate, weight, and posture.

Further, the sensor unit 116 capture the events in the real world environment according to a field of view of the sensor unit 116. In addition, the sensor unit 116 captures the event and/or obtains the at least one parameter associated with the event by using various analysis techniques as known in the art. Examples of such analysis techniques include, but not limited to, image/video analysis techniques, position/location detection techniques, depth sensing techniques, range imaging techniques, speech recognition techniques, natural language processing techniques, physiological data processing techniques, face recognition techniques, and facial expression recognition techniques.

Upon capturing the event, the event detection unit 117 determines if the event satisfies at least one predetermined rules. The predetermined rules can indicate the following, but not limited to:

(a) the event or the at least one parameter associated with the event is predefined;

(b) the event or the at least one parameter associated with the event is specified by a VR user;

(c) the at least one parameter associated with the event is having a value higher than a predefined threshold value; and (d) the at least one parameter associated with the event is having a constant value for a predefined threshold value of time.

In one implementation, the predetermined rules can be predefined and stored in the memory 104 during manufacturing of the VR device 101. In another implementation, the predetermined rules can be defined/specified by the VR user via a user-interface, as described in the FIG. 2 later and further stored in the memory 104.

Accordingly, the event detection unit 117 fetches the predetermined rules from the memory 104. Thereafter, the event detection unit 117 analyses the event based on the fetched predetermined rules and determines if the captured event satisfies at least one predetermined rules. Additionally, the event detection unit 117 may determine/identify the parameter(s) associated with the event captured by the sensor unit 116. Thereafter, the event detection unit 117 analyses the identified parameter(s) based on the fetched predetermined rules and determine if the captured event satisfies at least one predetermined rules. Upon negative determination, the event detection unit 117 does not perform any further processing and the sensor unit 116 continues capturing events in the real world environment.

However, upon positive determination, the rendering unit 118 presents information pertaining to the captured event. The rendering unit 118 presents the information without absolute interruption of an ongoing display of VR content on the VR enabled display unit 106. Examples of the VR content include, but not limited to, movies, games, and animation. In one implementation, the VR content is streamed directly from a VR content server (not shown in the figure) over the network 115. In another implementation, the VR content is fetched from a storage unit coupled to the VR device 101 and rendered on the VR enabled display unit 106. Examples of the VR content storage unit include, but not limited to, an external electronic device such as personal computer, a memory such as the memory 104, and a USB drive.

In accordance with the present invention, the predetermined rules define the events and/or their associated parameters and value, which result in presentation of information from the real world environment. Table 1 below illustrates example predetermined rules for processing the example events. For the sake of brevity, only eleven events have been described. However, it is to be understood multiple types of events can also be defined.

TABLE 1

| S. No | Predefined Event | Parameter 1 | Threshold Value 1 | Parameter 2 | Threshold Value 2 | Real World Scenario | Present Information |
|---|---|---|---|---|---|---|---|
| 1. | Movement of VR device | Direction of movement | Vertically Down | | | VR user moves his head in Vertical down direction. | Yes |
| | | | | | | VR user moves his head in any direction other than vertical down direction. | No |
| 2. | Gesture Input | Shape of Gesture | Pair of inverted 'L' | | | VR user makes an area selection gesture | Yes |

TABLE 1-continued

| S. No | Predefined Event | Parameter 1 | Threshold Value 1 | Parameter 2 | Threshold Value 2 | Real World Scenario | Present Information |
|---|---|---|---|---|---|---|---|
| | | | | | | VR user makes any gesture other than area selection gesture | No |
| 3. | Proximity of a person to the VR device | Distance between the person and the VR device | 2.5 meters | Face | Pre-stored Image | Distance between a secondary person and a VR device | Yes |
| 4. | Proximity of a object to the VR device (Moving Object) | Speed of the object | 40 kmph | Distance between the object and the VR device | 10 meters | Object moving towards the VR user | Yes |
| 5. | Proximity of a object to the VR device (Stationary Object) | Distance between the object and the VR device | 5 meters | | | VR user moving towards stairs | Yes |
| 6. | Eye gaze movement | Time of Gaze | 15 seconds | | | Secondary person watching the VR user | Yes |
| 7 | Audio Input | Voice Pattern | Pre-stored voice pattern of secondary person 'TBZ' | | | Secondary person 'TBZ' calling the VR user | Yes |
| 8 | Audio Input | Phrase | ABC (name of VR user) | | | Secondary person 'WER' calling the VR user without using his name 'ABC' | No |
| 9 | Audio Input | Voice Pattern | Pre-stored voice pattern of secondary person GGP | Phrase | ABC (name of VR user) | Secondary person 'GGP' calling the VR user by using his name 'ABC' | Yes |
| 10 | Physiological state - Fear | Heart Rate | V11 | | | VR user is watching a VR content | Yes |
| 11 | Physiological state - Physical Stress due to exercising | Heart Rate | V12 | Perspiration Level | V21 | VR user is watching a VR content | Yes |

As indicated in the table above, column 'Predefined Event' defines the event, which results in presentation of information. Column 'Parameter' defines which parameters of the defined events are to be further analysed such that information can be presented when the parameter has value as indicated in column 'Threshold Value'. As indicated, each event can have one or more associated parameters. It would be understood that the value in the column 'Threshold Value' can be an arithmetical value for performing arithmetic test and an input which can be used for performing logical test/comparison for analysing the events. As such, more than one value or a range of values can be defined in the column 'Threshold Value'. For the sake of brevity only two parameters and corresponding threshold values are illustrated. However, it is to be understood other parameters can also be defined.

The table further includes two columns, namely, 'Real World Scenario' and 'Present Information'. The column 'Real World Scenarios' indicates some example events captured in real world environment by the sensor 116 that will be analysed based on data in columns 'Predefined Event', 'Parameter', and 'Threshold Value'. The column 'Present Information' indicates whether information pertaining to the 'Real World Scenarios' will be presented or not based on the analysis. The column 'Real World Scenarios' is provided for the sake of clarity and understanding only and therefore will not form a part of 'predetermined rules'. The following paragraphs describe how the example events in 'Real World Scenarios' are analysed based on data in columns 'Predefined Event', 'Parameter', and 'Threshold Value'. Based on the analysis and rules a decision in respect of whether or not to present information is taken and the same is depicted by yes/no phrase in the column 'Present Information'.

In one example, the VR user moves his head in vertical down direction with respect to ground surface. As such, the sensor unit 116 captures a movement of the VR device 101. In addition, the sensor unit 116 obtains a direction, i.e., vertical down direction, and speed associated with the movement. Referring to table 1 and serial number 1, the event detection unit 117 then determines the event, i.e., the movement of the VR device 101, satisfies the rules since the captured direction is 'vertically down' irrespective of the captured speed. Consequently, the rendering unit 118 presents information pertaining to the 'movement of the VR device 101' on the display unit 106, indicated by value 'Yes' in column 'Present Information'.

On the contrary, in another example, the VR user moves his head in any direction other than the vertical direction. As such, the sensor unit 116 captures a movement of the VR device 101 and obtains a direction, and/or speed associated with the movement. Referring to table 1 and serial number 1, the event detection unit 117 then determines the event, i.e., the movement of the VR device 101, does not satisfy the rules since the captured direction is different from 'vertically down'. Consequently, the rendering unit 118 does not present any information on the display unit 106, indicated by value 'No' in column 'Present Information'.

In one example, VR user makes an area selection gesture. As such, the sensor unit 116 captures a gesture input from the VR user and obtains a shape associated with the gesture input, i.e., pair of inverted 'L' shapes. Referring to table 1 and serial number 2, the event detection unit 117 then determines the event, i.e., the gesture input, satisfies the rules since the shape of the gesture input is pair of inverted 'L'. Consequently, the rendering unit 118 presents information pertaining to the 'gesture input' on the display unit 106, indicated by value 'Yes' in column 'Present Information'.

On the contrary, in another example, the VR user makes a gesture different from the 'area selector' gesture, such as swipe gesture. As such, the sensor unit 116 captures a gesture input and obtains a shape associated with the gesture input. Referring to table 1 and serial number 2, the event detection unit 117 then determines the event, i.e., the gesture input, does not satisfy the rules since the captured gesture input has a shape that is different from pair of inverted 'L'. Consequently, the rendering unit 118 does not present any information on the display unit 106, indicated by value 'No' in column 'Present Information'.

In one example, a secondary user is approaching the VR user. The sensor unit 116 captures the event as 'a person in proximate to the VR device 101'. The event detection unit 117 may obtain a distance between the person and the VR user/the VR device 101 from the sensor unit 116. Accordingly, referring to table 1 and serial number 3, the event detection unit 117 then determines the event, i.e., the proximity of the person to the VR device 101, satisfies the rules when the distance is equal to 2.5 meters. Consequently, the rendering unit 118 presents information pertaining to the secondary person on the display unit 106, indicated by value 'Yes' in column 'Present Information'. On the contrary, the event detection unit 117 determines the event, i.e., the proximity of the person to the VR device 101, does not satisfy the rules when the distance is different from 2.5 meters. Consequently, the rendering unit 118 does not present any information on the display unit 106.

Additionally, the event detecting unit 117 obtain an image of the secondary person from the sensor unit 116 and may perform a comparison of the image with pre-stored images to identify whether the secondary person is a 'known person' or 'unknown person'. When the secondary person is identified as 'known person' and the distance is equal to 2.5 meters, the rendering unit 118 may present a first type of information on the display unit 106. Likewise, when the secondary person is identified as an 'unknown person' and the distance is equal to 2.5 meters, the rendering unit 118 may present a second type of information on the display unit 106.

Alternatively, the event detecting unit 117 may determine facial expression of the secondary person from the image of the person. The rendering unit 117 may then present a third type of information in accordance with the determined facial expression.

In one example, an object is moving/approaching towards the VR user. The sensor unit 116 captures the event as 'an object in proximate to the VR device 101'. In addition, the sensor unit 116 obtains speed of the object and a distance between the object and the VR device 101. Referring to table 1 and serial number 4, the event detection unit 117 then determines the event, i.e., the proximity of the object to the VR device 101, satisfies the rules when the speed is 40 kilometres per hour (kmph) and the distance is less than are equal to 10 meters. Consequently, the rendering unit 118 presents information pertaining to the 'proximity of the object to the VR device 101' on the display unit 106, indicated by value 'Yes' in column 'Present Information'. On the contrary, the event detection unit 117 determines the event, i.e., the proximity of the object to the VR device 101, does not satisfy the rules when either the speed is not equal to 40 kmph or the distance is more than 10 meters. Consequently, the rendering unit 118 does not present any information on the display unit 106

In another example, VR user is moving towards a stationary object such as stairs. The sensor unit 116 captures the event as 'an object in proximate to the VR device 101'. In addition, the sensor unit 116 obtains a distance between the object and the VR user. Referring to table 1 and serial number 5, the event detection unit 117 then determines the event, i.e., the proximity of the object to the VR device 101, satisfies the rules when the distance between the VR user and the stairs is 5 meters. Consequently, the rendering unit 118 presents information pertaining to the 'proximity of the object to the VR device 101' on the display unit 106, indicated by value 'Yes' in column 'Present Information'.

In one example, a secondary person is watching/staring/gazing at the VR user. The sensor unit 116 captures the event as 'eye gaze movement'. The event detection unit 117 may obtain data from the sensor unit 116 to identify whether the gaze is constant for 15 seconds. Referring to table 1 and serial number 6, the event detection unit 117 then determines the event, i.e., the eye gaze movement, satisfies the rules when the gaze was constant for 15 seconds. Consequently, the rendering unit 118 presents information pertaining to the 'eye gaze movement' on the display unit 106 when the time of gaze is 15 seconds and more, indicated by value 'Yes' in column 'Present Information'. On the contrary, the rendering unit 118 does not present any information on the display unit 106 when the time of gaze is less than 15 seconds, indicated by value 'No' in column 'Present Information'.

In one example, a secondary person TBZ is calling the VR user. In one example, a secondary person WER is calling the VR user. In one example, a secondary person GGP is calling the VR user. In all the examples, the sensor unit 116 captures the event as 'audio input', obtains a voice pattern of the secondary user and words/phrases from the secondary person's speech. For the three different persons TBZ, WER, and GGP, different rules are saved as illustrated in serial numbers 7, 8, and 9, respectively, in table 1.

Referring to table 1 and serial number 7, the event detection unit 117 determines the event, i.e., the audio input satisfies the rules when the voice pattern of the secondary person TBZ matches with the pre-stored voice of the secondary person, even if the secondary person does not say any 'pre-stored phrase' or call the VR user by name. Consequently, the rendering unit 118 presents information pertaining to the 'audio input' on the display unit 106, indicated by value 'Yes' in column 'Present Information'.

However, referring to table 1 and serial number 8, the event detection unit 117 determines the event, i.e., the audio input does not satisfy the rules when the obtained words/phrases does not match with the pre-stored phrases, even if the voice pattern of the secondary person WER matches with a pre-stored voice of the secondary person. In other words, the speech of the secondary person WER does not include name of the VR user. Consequently, the rendering unit 118 does not present any information on the display unit 106, indicated by value 'No' in column 'Present Information'.

Likewise, referring to table 1 and serial number 9, the event detection unit 117 determines the event, i.e., the audio input satisfies the rules when the voice pattern of the secondary person GGP matches with the pre-stored voice of the secondary person and the obtained words/phrases matches with the pre-stored phrases (or name of VR user). Consequently, the rendering unit 118 presents information pertaining to the 'audio input' on the display unit 106, indicated by value 'Yes' in column 'Present Information'. On the contrary, if neither the voice pattern matches with pre-stored voice pattern nor the phrase matches with pre-stored phrases, the event detection unit 117 determines the event, i.e., the audio input does not satisfy the rules.

In one example, the VR user can experience physiological state/conditions while watching the VR content. As such, the sensor unit 116 captures various physiological parameters such as blood pressure, heartbeat, body temperature, sweat, respiration rate, perspiration rate, weight, and posture. For different physiological states, i.e., fear and physical stress due to exercising, different rules can be determined and saved as illustrated in serial numbers 10 and 11, respectively, in table 1.

Referring to table 1 and serial number 10, the event detection unit 117 determines the physical state as fear when the heart rate is equal to as, or more than V11. Consequently the rendering unit 118 presents information on the display unit 106, indicated by value 'Yes' in column 'Present Information' Likewise, referring to table 1 and serial number 11, the event detection unit 117 determines the physical state as physical stress due to exercising when the heart rate is equal to or more than V12 and perspiration rate is equal to or more than V21. Consequently, the rendering unit 118 presents information on the display unit 106, indicated by value 'Yes' in column 'Present Information'.

Further, in accordance with the invention, more than one sensor unit 116 can capture different events and/or obtain associated parameter(s) concurrently or consecutively. Accordingly, different rules can be defined for processing combination of events that may occur concurrently or consecutively.

In one example, a first sensor unit may capture eye gaze movement of the secondary person and a second sensor unit 116 may capture an image of the secondary person. Accordingly, the event detecting unit 117 may perform a comparison of the image with pre-stored images to identify the secondary person as 'known person' or 'unknown person' in addition to determining if the gaze is constant for a predefined value. When the secondary person is identified as a 'known person' and the gaze is constant for the predefined value, the rendering unit 118 presents a first type of information on the display unit 106. Likewise, when the secondary person is identified an 'unknown person' but the gaze is constant for a predefined value, the rendering unit 118 present may present a second type of information on the display unit 106.

In one example, a first sensor unit may capture eye gaze movement of the secondary person and a second sensor unit 116 may capture an audio/voice of the secondary person calling the VR user. Accordingly, the event detecting unit 117 determines if the audio includes pre-determined phrases in addition to determining if the gaze is constant for a predefined value. When the audio includes pre-determined phrases and the gaze is constant for a predefined value, the rendering unit 118 presents a first type of information on the display unit 106. Likewise, when the audio does not includes pre-determined phrases but the gaze is constant for the predefined value, the rendering unit 118 may present a second type of information on the display unit 106.

Although, only few examples of real world scenarios have been described above, it is to be understood that many real world scenarios can be defined and correspondingly multiple rules can be defined.

Further, as described earlier, upon determination of the event satisfying the rules, the rendering unit 118 presents the information related to the event on the VR enabled display unit 106. In one implementation, the information is a real time video depicting the real world environment. In one implementation, the information is a real time image depicting the real world environment. In one implementation, the information is a real time directional cue. In one implementation, the information is a text notification. Further, the rendering unit 118 presents the information in one of: an overlay mode, a picture-in-picture mode, a split screen mode, a split view mode, and sectional view mode.

In one implementation, the rendering unit 118 presents the information based on predetermined rules stored in the memory 104. The predetermined rules can indicate, but not limited to, the type of information to be presented and a display mode for presenting the type of information, based on the captured event. In one implementation, the predetermined rules can be predefined and stored in the memory 104 during manufacturing of the VR device 101. In another implementation, the predetermined rules can be defined/specified by the VR user via a user-interface, as described in the FIG. 2 later and further stored in the memory 104.

Table 2 below illustrates example predetermined rules for displaying information related the example events. For the sake of brevity, only fourteen events have been described. However, it is to be understood multiple type of events can also be defined.

TABLE 2

| S. No | Predefined Event | Type of Information to be presented | Display mode |
|---|---|---|---|
| 1 | Movement of VR device | Real Time Video | PIP |
| 2 | Gesture Input | Real Time Image | Overlay |
| 3 | Proximity of a person to the VR device | Real Time Video | Sectional |
| 4 | Proximity of a object to the VR device (speed = 40 kmph; distance <= 10 meter) | Directional Cue, Real Time Video | Split |

TABLE 2-continued

| S. No | Predefined Event | Type of Information to be presented | Display mode |
|---|---|---|---|
| 5 | Proximity of a object to the VR device (distance <= 5 meters) | Text Notification (Distance = 5 meters); Real Time Image (Distance <5 meters); | Overlay |
| 6 | Eye gaze movement | Real Time Image | PIP |
| 7 | Audio Input (Pre-stored voice pattern only) | Real Time Image | Split |
| 8 | Audio Input (Pre-stored phrase only) | Real Time Video | PIP |
| 9 | Audio Input (Pre-stored voice pattern and pre-stored phrase) | Real Time Video | Sectional |
| 10 | Physiological state - Fear | Real Time Video | PIP |
| 11 | Physiological state - Physical stress due to exercising | Real Time Video | Sectional |
| 12 | Eye gaze movement + Image of Person | Text Notification (Gaze and unknown person); Real Time Image (Gaze and Known person); | Overlay; Split |
| 13 | Eye gaze movement + Facial Expression | Real Time Video | Split |
| 14 | Eye gaze movement + Audio Input (pre-stored phrase only) | Real Time Video | Sectional |

As indicated in the table above, column 'Predefined Event' defines the event, which results in presentation of information, as described with reference to Table 1. Data in columns 'Type of Information to be presented' and 'Display Mode' define what and how the information is to be displayed/presented. The following paragraphs describe what and how the information is displayed upon analysing example events in 'Real World Scenarios' of Table 1.

In one example, the sensor unit 116 captures a movement of the VR device 101, as described in reference to table 1 and serial number 1. As such, the event detection unit 117 determines the event, i.e., the movement of the VR device 101, satisfies the rules when the captured direction is 'vertically down'. Accordingly, referring to table 2 and serial number 1, the rendering unit 118 presents a 'real time video' from the real world environment in 'picture in picture (PIP)' mode when the VR device is moved in 'downwards' direction.

In one example, the sensor unit 116 captures a gesture input from the VR user, as described in reference to table 1 and serial number 2. As such, the event detection unit 117 then determines the event, i.e., the gesture input, satisfies the rules when a shape associated with the gesture input is' 'pair of inverted L shape'. Accordingly, referring to table 2 and serial number 2, when the event is satisfies the rules, the rendering unit 118 presents a 'real time image' from the real world environment in an 'overlay' mode.

In one example, the sensor unit 116 captures a person in proximate to the VR device 101, as described in reference to table 1 and serial number 2. As such, the event detection unit 117 determines the event, i.e., the proximity of the person to the VR device 101, satisfies the rules when the distance is less than or equal to 10 meters. Accordingly, referring to table 2 and serial number 3, the rendering unit 118 presents a 'real time video' of the person from the real world environment in a 'sectional' mode.

In one example, the sensor unit 116 captures an object in proximate to the VR device 101, as described in reference to table 1 and serial number 4. As such, the event detection unit 117 determines the event, i.e., the proximity of the object to the VR device 101, satisfies the rules when the speed is 40 kmph. Accordingly, referring to table 2 and serial number 4, the rendering unit 118 presents a 'directional cue' based on movement of the object and a 'real time video' of the moving object from the real world environment in a 'split' mode.

In one example, the sensor unit 116 captures an object in proximate to the VR device 101, as described in reference to table 1 and serial number 5. As such, the event detection unit 117 determines the event, i.e., the proximity of the object to the VR device 101, satisfies the rules when the distance is less than or equal to 5 meters. Accordingly, referring to table 2 and serial number 5, the rendering unit 118 presents a 'text notification' indicative of the stairs from the real world environment in an 'overlay' mode when the distance is equal to 5 meters. However, when the distance is less than 5 meters, the rendering unit 118 presents a 'real time image' of the stairs.

In one example, the sensor unit 116 captures an eye gaze movement of a person staring at the VR user, as described in reference to table 1 and serial number 6. As such, the event detection unit 117 determines the event, i.e., the eye gaze movement, satisfies the rules when the gaze was constant for 15 seconds. Accordingly, referring to table 2 and serial number 6, the rendering unit 118 presents a 'real time image' of the person staring at the VR user from the real world environment in a 'PIP' mode.

In one example, the sensor unit 116 captures an audio input, i.e., audio of the secondary person TBZ calling the VR user, as described in reference to table 1 and serial number 7. As such, the event detection unit 117 determines the event, i.e., the audio input, satisfies the rules when voice pattern of the secondary person TBZ matches with the pre-stored voice pattern. Accordingly, referring to table 2 and serial number 7, the rendering unit 118 presents a 'real time image' of the secondary person TBZ calling the VR user from the real world environment in a 'split' mode.

In one example, the sensor unit 116 captures an audio input, i.e., audio of the secondary person WER calling the VR user, as described in reference to table 1 and serial number 8. As such, the event detection unit 117 determines the event, i.e., the audio input, satisfies the rules when phrase from the audio match with the pre-stored phrases. Accordingly, referring to table 2 and serial number 8, the rendering unit 118 presents a 'real time video' of the secondary person WER calling the VR user from the real world environment in a 'PIP' mode.

In one example, the sensor unit 116 captures an audio input, i.e., audio of the secondary person GGP calling the VR user, as described in reference to table 1 and serial number 9. As such, the event detection unit 117 determines the event, i.e., the audio input, satisfies the rules when voice pattern of the secondary person GGP match with the pre-stored voice pattern and phrase from the audio match with the pre-stored phrases. Accordingly, referring to table 2 and serial number 9, the rendering unit 118 presents a 'real time video' of the secondary person GGP calling the VR user from the real world environment in a 'sectional' mode.

In one example, the sensor unit 116 captures physiological state (fear) of the VR user, as described in reference to table 1 and serial number 10. As such, the event detection unit 117 determines the event, i.e., the physiological state, satisfies the rules when the heart rate is equal to or more than V11. Accordingly, referring to table 2 and serial number 10, the rendering unit 118 presents a 'real time video' from the real world environment in a 'PIP' mode.

In one example, the sensor unit 116 captures physiological state (physical stress due to exercising) of the VR user, as described in reference to table 1 and serial number 10. As such, the event detection unit 117 determines the event, i.e., the physiological state, satisfies the rules when the heart rate is equal to or more than V12 and the perspiration rate is equal to or more than V21. Accordingly, referring to table 2 and serial number 11, the rendering unit 118 presents a 'real time video' from the real world environment in a 'sectional' mode.

As described earlier, in accordance with the invention, more than one sensor unit 116 can capture different events and/or obtain associated parameter(s) concurrently or consecutively. Accordingly, different rules can be defined for presenting information pertaining to combination of events that may occur concurrently or consecutively.

In one example, a first sensor unit may capture eye gaze movement of the secondary person and a second sensor unit 116 may capture an image of the secondary person. Accordingly, the event detecting unit 117 may perform a comparison of the image with pre-stored images to identify the secondary person as 'known person' or 'unknown person' in addition to determining if the gaze is constant for a pre-defined value. Referring to table 2 and serial number 12, when the secondary person is identified as a 'known person' and the gaze is constant for the predefined value, the rendering unit 118 presents a real time image of the person in a 'split' mode. However, when the secondary person is identified as an 'unknown person' but the gaze is constant for the predefined value, the rendering unit 118 presents only text notification in a 'overlay' mode indicating a person is staring at the VR user.

In one example, a first sensor unit may capture eye gaze movement of the secondary person and a second sensor unit 116 may capture an audio/voice of the secondary person calling the VR user. Accordingly, the event detecting unit 117 determines if the audio includes pre-determined phrases in addition to determining whether duration of the gaze. Referring to table 2 and serial number 14, when the audio includes pre-determined phrases and the gaze is constant for a predefined value, the rendering unit 118 presents a real time video of the secondary person in 'sectional' mode. On the contrary, when the audio does not includes pre-determined phrases but the gaze is constant for the predefined value, the rendering unit 118 may present information pertaining to 'eye gaze movement' only. Thus, referring to table 2 and serial number 6, the rendering unit 118 may present a real time image of the secondary person in a 'PIP' mode.

Although, only few examples of real world scenarios have been described above, it is to be understood that many real world scenarios can be defined and correspondingly multiple rules can be defined.

Further, in one implementation, the presentation of information can include determination of a display area and/or a display position. Accordingly, in one such implementation, the rendering unit 118 determines a direction of the event thus captured. Based on the determined direction, the rendering unit 118 determines a position on the VR enabled display unit 106. The rendering unit 118 then selects a display area on the VR enabled display unit 106 based on the determined position. Upon determining the display area, the rendering unit 118 presents the information at the selected display area on the VR enabled display unit 106.

In one example, the sensor unit 116 captures an object in proximate to the VR device 101, as described in reference to table 1 and serial number 4. As such, the event detection unit 117 determines the event, i.e., the proximity of the object to the VR device 101, satisfies the rules when the speed is 40 kmph. Accordingly, the rendering unit 118 determines a direction of the object, i.e., whether the object is approaching towards the VR user or not. Consequently, the rendering unit 118 determines position and area based on the determined direction. As such, referring to table 2 and serial number 4, the rendering unit 118 presents the 'real time video' of the moving object in the determined position and area.

In another such implementation, the rendering unit 118 determines, based on at least one predetermined rule, at least one of a type of the captured event, a priority level of the event, and a type of application currently rendering the VR content. Upon determining the type and/or the priority level of the captured event and/or the type of application currently rendering the VR content, the rendering unit 118 selects a display area on the VR enabled display unit 106 based on said determination. Upon determining the display area, the rendering unit 118 presents the information at the selected display area on the VR enabled display unit 106. In addition, the rendering unit 118 may determine the display area based on pre-stored settings corresponding to display area based on display mode. Examples of such settings include, but not limited to, window size in PIP mode, pane size in overlay mode, and window size in sectional mode.

Examples of the type of captured event can include, but not limited to, negligible threat, low level of threat, medium level of threat, and high level of threat. In one example, the priority level can have two options such as 'low' and 'high'. In another example, the priority level can have three options such as 'low', 'medium', and 'high'. Thus, the priority level can have at least two options selected from 'n' options; where n is greater than 2. Examples of the application rendering the VR content can include, but not limited to, media streaming application, media player application, and gaming application.

In one implementation, the predetermined rules can be predefined and stored in the memory 104 during manufacturing of the VR device 101. In another implementation, the predetermined rules can be defined/specified by the VR user via a user-interface and further stored in the memory 104.

The predetermined rules can be stored in the memory 104. Table 3 illustrates example predetermined rules for displaying information related the example events. For the sake of brevity, only eight events have been described. However, it is to be understood multiple types of events can also be defined.

TABLE 3

| S. No | Predefined Event | Type of Event | Priority Level | Type of Application |
|---|---|---|---|---|
| 1 | Movement of VR device | Negligible Threat | | |
| 2 | Gesture Input | Negligible Threat | | |
| 3 | Proximity of a person to the VR device | Medium level of Threat | Low | |
| 4 | Proximity of a object to the VR device (speed = 40 kmph; distance <= 10 meter) | High Level of Threat | High | Media player |
| 5 | Proximity of a object to the VR device (speed = 0 kmph; distance <= 5 meters) | High Level of Threat | High | Gaming Application |
| 6 | Eye gaze movement | | Medium | |
| 7 | Physiological state - Fear | Low level of Threat | Medium | Streaming Media |
| 8 | Physiological state - Physical stress due to exercising | | Medium | Media player |

As indicated in the table above, column 'Predefined Event' defines the event, which results in presentation of information based on at least one of type of event defined in column 'Type of Event', priority level defined for the captured event in column 'Priority Level', and type of application defined in column 'Type of Application'. Data in the columns define where the information is to be displayed/presented. As would be understood, data for all the columns need not be defined for each of the event. The following paragraphs described what, how, and where the information is displayed upon analysing example events in 'Real World Scenarios' of Table 1.

In one example, the sensor unit 116 captures a movement of the VR device 101, as described in reference to table 1 and serial number 1. As such, the event detection unit 117 determines the event, i.e., the movement of the VR device 101, satisfies the rules when the captured direction is 'vertically down'. Accordingly, referring to table 3 and serial number 1, the rendering unit 118 determines the type of event as 'negligible threat'. As such, referring to table 2 and serial number 1, the rendering unit 118 presents a 'real time video' from the real world environment in a 'PIP' mode. In one example of the 'PIP' mode, a display area of the real time video is smaller than display area for the VR content based on pre-stored settings. In another example of the 'PIP' mode, a display area of the real time video is greater than display area for the VR content based on pre-stored settings.

In one example, the sensor unit 116 captures a gesture input from the VR user, as described in reference to table 1 and serial number 2, the event detection unit 117 then determines the event, i.e., the gesture input, satisfies the rules when the gesture input is indicative of 'pair of inverted L shape'. Accordingly, referring to table 3 and serial number 2, the rendering unit 118 determines the type of event as 'negligible threat' and priority level as 'low'. As such, referring to table 2, when the event is 'area selector', the rendering unit 118 presents a 'real time image' from the real world environment in an 'overlay' mode. In one example of the 'overlay' mode, a display area of the real time video is smaller than display area for the VR content based on pre-stored settings. In another example of the 'overlay' mode, a display area of the real time video is greater than display area for the VR content based on pre-stored settings.

In one example, the sensor unit 116 captures a person in proximate to the VR device 101, as described in reference to table 1 and serial number 3. As such, the event detection unit 117 determines the event, i.e., the proximity of the person to the VR device 101, satisfies the rules when the distance is less than or equal to 10 meters. Accordingly, referring to table 3 and serial number 3, the rendering unit 118 determines the type of event as 'medium level of threat' and priority level as 'low'. As such, referring to table 2 and serial number 3, the rendering unit 118 presents a 'real time video' of the person from the real world environment in a 'sectional' mode. In one example of the 'sectional' mode, a display area of the real time video is greater than display area for the VR content.

In one example, the sensor unit 116 captures an object in proximate to the VR device 101, as described in reference to table 1 and serial number 4. As such, the event detection unit 117 determines the event, i.e., the proximity of the object to the VR device 101, satisfies the rules when the speed is 40 kmph. Accordingly, referring to table 3 and serial number 4, the rendering unit 118 determines the type of event as 'high level of threat' and priority level as 'high'. Further, the rendering unit 118 determines a direction of the object, i.e., whether the object is approaching towards the VR user or not. Consequently, the rendering unit 118 determines position and area based on the determined direction. As such, referring to table 2 and serial number 4, the rendering unit 118 presents a 'directional cue' and a 'real time video' of the object from the real world environment in a 'split' mode. The rendering unit presents the 'directional cue' to indicate the VR user to move to a direction different from the approaching object.

Furthermore, the rendering unit 118 determines the type of application through which the VR user is viewing the VR content. If the determined type of application is 'media player' as indicated in table 3 and serial number 4, the rendering unit 118 determines the display area for the real time video as being greater than a display area of the VR content. However, if the determined type of application is different from the 'media player', the rendering unit 118 determines the display area for the real time video as being equal to the display area of the VR content. Thus, the VR user is able to identify the approaching object.

In one example, the sensor unit 116 captures an object in proximate to the VR device 101, as described in reference to table 1 and serial number 5. As such, the event detection unit 117 determines the event, i.e., the proximity of the object to the VR device 101, satisfies the rules when the speed is 0 kmph and the distance is 5 meters. Accordingly, referring to table 3 and serial number 5, the rendering unit 118 determines the type of event as 'high level of threat' and priority level as 'high'. As such, referring to table 2 and serial number 5, the rendering unit 118 presents a 'text notification' from the real world environment in an 'overlay' mode such that the 'text notification' is present in centre of the screen and has bold letters.

Furthermore, the rendering unit 118 determines the type of application through which the VR user is viewing the VR content. If the determined type of application is 'gaming application' as indicated in table 3 and serial number 5, the rendering unit 118 presents the text notification at top of the screen in the 'overlay mode'. However, if the determined type of application is different 'gaming application', the rendering unit 118 presents the text notification at centre of the screen in the 'overlay mode'.

In one example, the sensor unit 116 captures an eye gaze movement of a person staring at the VR user, as described in reference to table 1 and serial number 6. As such, the event detection unit 117 determines the event, i.e., the eye gaze movement, satisfies the rules when the gaze was constant for 15 seconds. Accordingly, referring to table 3 and serial number 6, the rendering unit 118 determines the priority level as 'medium' for the captured event. As such, referring to table 2 and serial number 6, the rendering unit 118 presents a 'real time image' of the person from the real world environment in a 'PIP' mode.

In one example, the sensor unit 116 captures physiological state (fear) of the VR user, as described in reference to table 1 and serial number 10. As such, the event detection unit 117 determines the event, i.e., the physiological state, satisfies the rules when the heart rate is equal to or more than V11. Accordingly, referring to table 3 and serial number 7, the rendering unit 118 determines the type of event as 'low level of threat' and priority level as 'medium'. As such, referring to table 2 and serial number 10, the rendering unit 118 presents a 'real time video' of the real world environment in 'PIP' mode.

Further, the rendering unit 118 determines the type of application through which the VR user is viewing the VR content. If the type of application is 'streaming media', the rendering unit 118 presents the real time video as main picture and the VR content in secondary picture in the PIP mode. If the type of application is different from the 'streaming media', the rendering unit 118 presents the VR content as main picture and the real time video in secondary picture in the PIP mode.

In one example, the sensor unit 116 captures physiological state (physical stress due to exercising) of the VR user, as described in reference to table 1 and serial number 10. As such, the event detection unit 117 determines the event, i.e., the physiological state, satisfies the rules when the heart rate is equal to or more than V12 and the perspiration rate is equal to or more than V21. Accordingly, referring to table 3 and serial number 8, the rendering unit 118 determines priority level as 'medium'. Further, the rendering unit 118 determines the type of application through which the VR user is viewing the VR content. If the type of application is 'media player', the rendering unit 118 presents a 'real time video' of the real world environment in a 'sectional' mode as indicated in table 2 and serial number 11. The real time video is presented such that the display area of the real time video is larger than a display area of the VR content. If the type of application is different from the 'media player', the rendering unit 118 presents the real time video such that the display area of the real time video is equal to the display area of the VR content.

Although, only few examples of real world scenarios have been described above, it is to be understood that many real world scenarios can be defined and correspondingly multiple rules can be defined.

Further, upon presenting the information, the event detection unit 117 detects a view-time event. The view-time event controls the presentation of the information on the VR enable display unit 106. In one implementation, the view-time event is expiry of a predetermined time from a time of capturing of the event. In one implementation, the view-time event is movement of the VR device from a first position to a second position subsequent to capturing of the event. In one implementation, the view-time event is reception of predefined gesture input. In one implementation, the view-time event is reception of predefined audio input.

Accordingly, in one implementation, the event detection unit 117 sets a time to a predetermined time from a time of capturing of the event. In one such implementation, the predetermined time can be defined/specified by a user in the memory 104 via a user-interface, as described in FIG. 2. In one such implementation, the predetermined time can be a default time defined/specified in the memory 104 during manufacturing of the VR device 101. The event detection unit 117 detect the view-time event upon expiry of the predetermined time.

In another implementation, the sensor unit 116 captures a further event and the event detection unit 117 detects whether the captured further is the view-time event. Thus, in one example, the sensor unit 116 captures an event indicative of movement of the VR device 101 from a first position to a second position subsequent to capturing of the event. In such example, the event detection unit 117 detects the movement of the VR device 101 as view-time event.

In another example, the sensor unit 116 captures gesture input. In such example, the event detection unit 117 determines if the received gesture input is predetermined in the memory 104. Examples of such predetermined gesture input can include, but not limited to, pinch out, swipe horizontal, swipe vertical, and return. Upon positive determination, the event detection unit 117 determines the received gesture input is the view-time event.

In one another example, the sensor unit 116 captures audio input. In such example, the event detection unit 117 determines if the received audio input is predefined in the memory 104 such as a predefined phrase and predefined voice pattern. Upon positive determination, the event detection unit 117 determines the received audio input is the view-time event.

Upon detection of the view-time event, the rendering unit 118 controls the presentation of the information on the VR enabled display unit 106. In one implementation, the rendering unit 118 controls the presentation of the information by deleting or removing the information from the VR enabled display unit 106. The deletion of the information enables continual viewing of the VR content on the VR enabled display unit 106.

In one implementation, the rendering unit 118 controls the presentation of the information by modifying at least one parameter of the information being presented. In one example, the information currently being presented on the VR display unit 106 is a text notification. In such example, the rendering unit 118 controls the presentation by enlarging font of characters in the text notification.

In one implementation, the rendering unit 118 controls the presentation of the information by replacing existing information with new information. In one example, the information currently being presented on the VR display unit 106 is a text notification. In such example, the rendering unit 118 controls the presentation by replacing the text notification with a real time video/image.

In one implementation, the rendering unit 118 controls the presentation of the information by modifying a display area within which the information is being presented. In one example, the information currently being presented on the VR display unit 106 is a real time video. The real time video is presented in an 'overlay' mode such that a display area of the real time video is smaller than display area for the VR content. In such example, the rendering unit 118 controls the presentation by increasing the display area of the real time video such that the display area of the real time video is greater than the display area for the VR content, i.e., zooming out the real time video.

In one implementation, the rendering unit 118 controls the presentation of the information by modifying display mode through which the information is presented. In one example, the information currently being presented on the VR display unit 106 is a real time video in an overlay mode. In such example, the rendering unit 118 controls the presentation by presenting the real time video in a sectional mode.

In one implementation, the rendering unit 118 controls the presentation of the information by moving a position of the information. In one example, the information currently being presented on the VR display unit 106 is a real time video. The real time video is presented in a PIP mode on left side of the screen. In such example, the rendering unit 118 controls the presentation by changing the position to right side of the screen.

In one implementation, the rendering unit 118 controls the presentation of the information by continuing presenting the information on the VR enabled display unit 106 until a further view-time event is detected. In one example, the information currently being presented on the VR display unit 106 is a real time image of a secondary person trying to interact with the VR user. In such example, the rendering unit 118 controls the presentation by continuing presenting the real time image when the VR user starts interacting with the secondary user, upon detecting voice of the VR user. The rendering unit 118 may further control the presentation upon detecting a specific word from the VR user.

Figure 2:
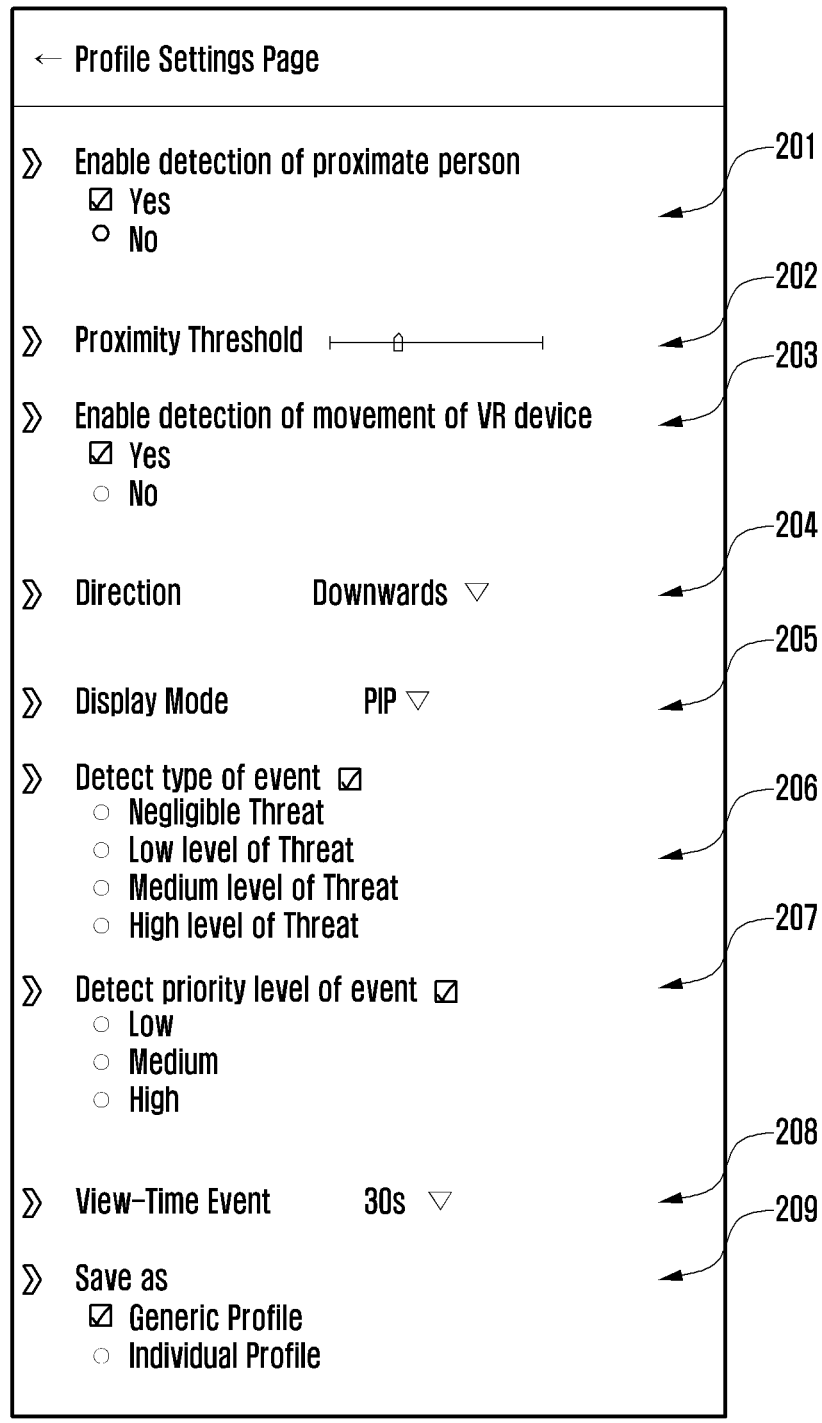
FIG. 2 illustrates example user-interface to set rules according to an embodiment of the present invention.

FIG. 2 illustrates example user-interface 200 to set rules according to an embodiment of the present invention. In one implementation, the event detection unit 117 provides the user-interface 200. The user-interface can be accessed by mechanisms as known in the art. In one example, the user-interface corresponds to a profile settings page. The profile settings page can be accessed on the VR device 101 or on the external electronic device 113. The user-interface 200 provides various options to select event(s), parameter(s) associated with the event(s), threshold value(s) corresponding to the at least one parameter, action associated with the event, and type(s) of the event(s) to set corresponding rules for the event(s). The options can be selected/enabled using mechanism as known in the art. Upon receiving user-input corresponding to enabling the various options, the rules are stored in the memory 104.

Referring to FIG. 2, the user-interface 200 provides an option 201 to enable detection of event indicative of a person proximate to the VR device 101. The user can enable the option 201 (represented by tick mark) in a manner as known in the art. The user-interface 200 further provides option 202 to set a threshold value for distance/proximity, a parameter associated with the above event. The user can set the threshold value (represented by a sliding bar) in a manner as known in the art.

The user-interface 200 further provides an option 203 to enable detection of movement of the VR device 101. The user can enable the option 201 (represented by tick mark) in a manner as known in the art. The user-interface 200 further provides option 204 to set a value of a direction of the movement, a parameter associated with the above event. The value of the direction can be selected from a list comprising of directions. The user can set the threshold value (represented by drop-down menu) in a manner as known in the art. In the figure, the direction is set as vertical downwards with respect to ground. In a similar manner, for each event the user-interface 200 provides options to set rules.

The user-interface 200 further provides options to set rules for display or presentation of information such as display mode, type of event, and priority level. As such, the user-interface 200 provides an option 205 to select the display mode from a list comprising of an overlay mode, a picture-in-picture (PIP) mode, a split screen mode, a split view mode, and sectional view mode. The user can select the display mode (represented by drop-down menu) in a manner as known in the art. In the figure, the display mode is set as PIP.

The user interface 200 further provides an option 206 to select type of event as negligible threat, low level of threat, medium level of threat, and high level of threat. The user interface 200 further provides an option 207 to select priority level as medium, high, and low. The user can enable the options 206 and 207 (represented by tick mark) in a manner as known in the art.

The user interface 200 further provides an option 208 to select the view-time event from a list comprising of time, gesture input, audio input, and movement of the VR device. In the figure, the view-time event is set as time/duration to 30 seconds.

Upon receiving user-input corresponding to selection of various rules via the user-interface 200, the event detection unit 117 stores the rules in the memory 104. In an example, as described earlier, the rules can be stored in a tabular form.

Further, in one implementation, the event detection unit 117 enables multiple users to create/select rules according to interests of the multiple users using the VR device 101. Thus, multiple VR users can create/select customised group of rules for themselves to process only those event(s) that match their interests. Each such customised group of rules can be saved as a profile of the corresponding user in the memory 104.

Accordingly, the user-interface 200 can provide an option 209 to save the customised group of rules as generic rules or profile specific rules. When the user selects the option 209 to save the rules as generic rules, the rules are applied irrespective of any user using the VR device 101. On the contrary, when the user selects the option 209 to save the rules as profile specific rules, the rules are applied in accordance with a user using the VR device 101. The user can enable the option 209 (represented by tick mark) in a manner as known in the art.

Further, when the rules are saved as profiles for multiple users, the event detection unit 117 fetches a profile of a user currently using the VR device 101 from the memory 104 and processes the captured event in accordance with the rules saved in the profile. In one implementation, the event detection unit 117 fetches the profile based on a user-input indicating selection of the profile prior to viewing the VR content by the user on the VR device 101. The user-input can be voice command, gesture command, and touch based input. In another implementation, the sensor unit 116 detects the user based on biometric parameters such as face and fingerprint, and provides corresponding signal/data to the event detection unit 117.

FIGS. 3 to 10 illustrate various examples of displaying information on a VR device, in accordance with one embodiment of the present invention.

FIGS. 3A, 3B, and 3C illustrate first example 300 of displaying of information from real world environment on a VR device 301, in accordance with an embodiment of the present invention. The VR device 301 includes the units as described in reference to FIGS. 1A and 1B.

Referring to FIG. 3A, a user 302 wears the VR device 301 directed in a horizontal direction 303 (represented by dashed horizontal arrow) with respect to ground surface. The rendering unit 118 renders a VR content 304 on the VR enabled display unit 106. The below table indicates the predetermined rules set in the example:

| | |
|---|---|
| Event 1 | Proximity of Object |
| Parameter 1.1 | Proximity/Direction |
| Threshold Value 1.2.1 | 5 m |
| Threshold Value 1.2.2 | 1 m |
| Type of Information 1 | Text Notification; Real Time Image |
| Display Mode 1 | Overlay |
| Event 2 | Movement of VR device |
| Parameter 2.1 | Direction |
| Threshold Value 2.2 | Vertically Down with respect to ground surface |
| Type of Information 2 | Real Time Video |
| Display Mode 2 | Picture in Picture (PIP) |
| View-time event | 45 seconds |

Referring to FIG. 3B, the user 302 is moving towards stairs in a real world environment 305. The sensor unit 116 captures the event as 'Proximity of an object' in the real world environment 305, i.e., proximity of the stairs, and distance of the user 302 from the stairs. Upon capturing, the event detection unit 117 determines if the event satisfies the predetermined rules as described earlier, i.e., by determining whether the distance between the stairs and the user is greater than or equal to 5 meters. When the distance is equal to the 5 meters (represented by reference numeral 1), the rendering unit 118 presents a text notification 306 indicating the user 302 is approaching the stairs at 5 meters in an overlay mode.

Further, in the real world environment 305, the user 302 may keep moving towards the stairs. As such, the sensor unit 116 may again capture the event as 'Proximity of an object' in the real world environment 305, i.e., proximity of the stairs, and distance of the user 302 from the stairs. Upon capturing, the event detection unit 117 determines if the event satisfies the predetermined rules in the above table as described earlier, i.e., by determining whether the distance between the stairs and the user is equal to 1 meter. The rendering unit 118 may present either a further text notification or an image of the stairs when the distance is equal to the 1 meter (represented by reference numeral 2).

Additionally, or in alternative, referring to FIG. 3C, the user 302 may move the VR device 301 in a downward direction 307 (represented by dashed horizontal arrow) by moving the head to look down the stairs at a distance of 1 meter or less. Accordingly, the sensor unit 116 captures the event as 'movement of the VR device'. Upon capturing the event, the event detection unit 117 determines the event satisfies the predetermined rules in the above table as described earlier, i.e., by determining whether the movement of the VR device 301 is in vertically down direction.

Accordingly, the rendering unit 118 presents a real time video 308 of the real world environment 305, i.e., the stairs in PIP mode. The event detection unit 117 then sets a timer to 45 seconds. Upon expiry of the 45 seconds, the event detection unit 117 detects the view-time event. Consequently, the rendering unit 118 removes the real time video 307 from the VR enabled display unit 106 and only the VR content 304 is displayed as illustrated in FIG. 3A. Further, the rendering unit 118 removes the real time video 308 upon expiry of 45 seconds as described earlier.

In a similar manner, the user might want to eat in real world environment while viewing the VR content. As such, the user may move the VR device in a downward direction by moving the head to look down a table in the real world environment. Accordingly, the sensor unit 116 captures the event as 'movement of the VR device'. Upon capturing the event, the event detection unit 117 determines the event satisfies the predetermined rules in the profile as described earlier. Accordingly, the rendering unit 118 presents a real time image of the real world environment, i.e., a plate with food, in PIP mode. The rendering unit 118 then displays the frame in PIP mode for 45 seconds.

FIGS. 4A, 4B, 4C, and 4D illustrate second example 400 of displaying of information from real world environment on a VR device 401, in accordance with an embodiment of the present invention. The VR device 401 includes the units as described in reference to FIGS. 1A and 1B.

Figure 4A:
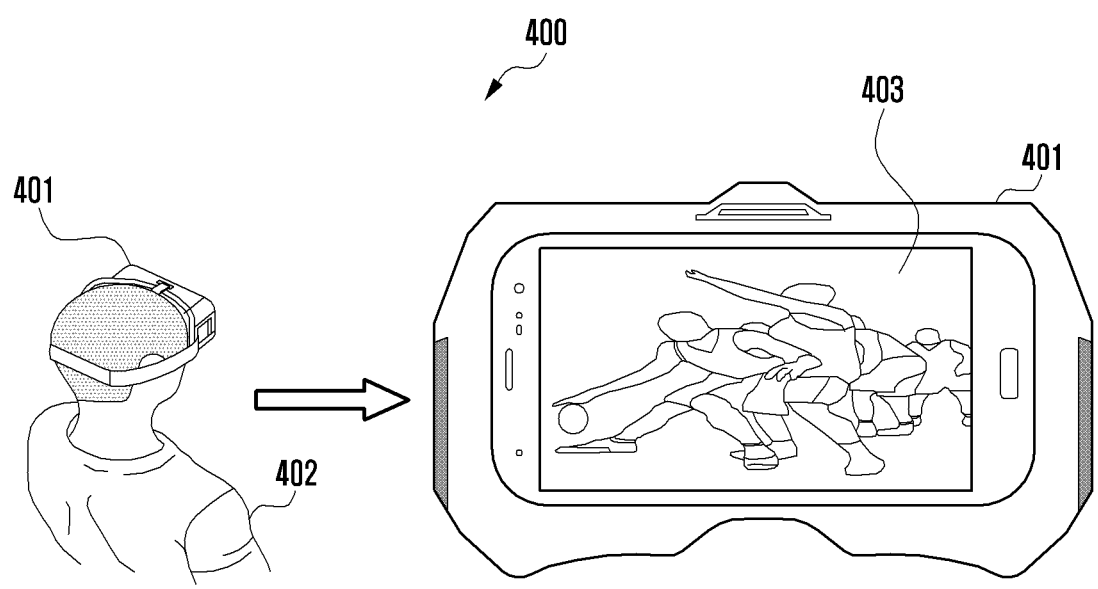

Referring to FIG. 4A, a user 402 wears the VR device 101 and the rendering unit 118 renders a VR content 403 on the VR enabled display unit 106. The below table indicates the predetermined rules set in the example:

| | |
|---|---|
| Event 1 | Eye Gaze Movement |
| Parameter 1.1 | Time of Gaze |
| Threshold Value 1.2 | 15 seconds |
| Type of Information 1 | Real Time Image |
| Display Mode 1 | PIP |
| View-time event 1 | 45 seconds |
| Event 2 | Audio Input |
| Parameter 2.1 | Phrase |
| Threshold Value 1.2 | ABC name of VR user |
| Type of Information 2 | Real Time Video |
| Display Mode 2 | Split Screen |
| View-time event 2.1 | 45 seconds |
| View-time event 2.2 | Voice Pattern of VR user |
| View-time event 2.3 | Phrase Bye |

Figure 4B:
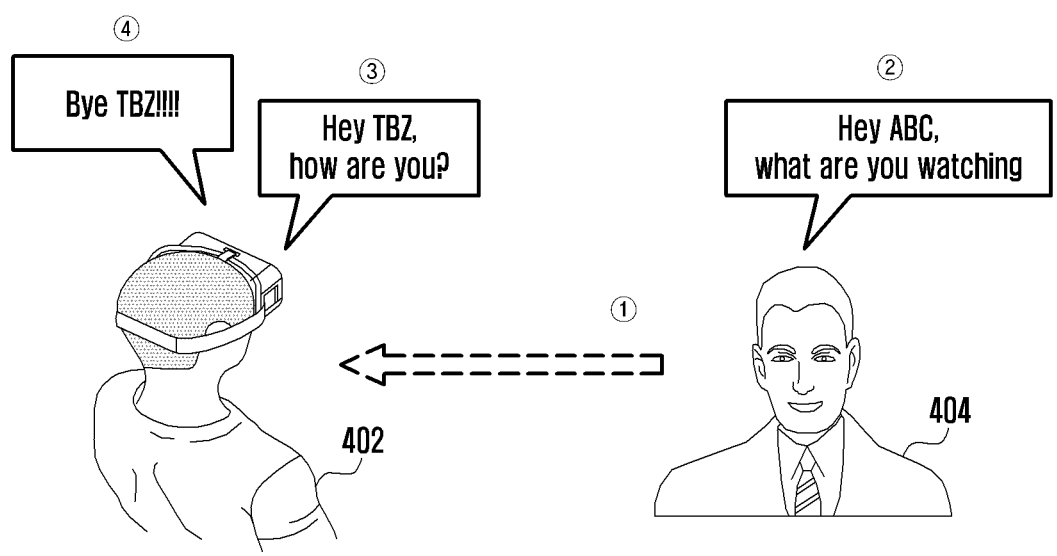

Referring to FIG. 4B, in one situation, secondary user 404 in a real world environment looks/gazes (represented by dashed arrow and reference numeral 1) at the user 402 while the user 402 is viewing the VR content 403 on the VR device 401. In such situation, the secondary user 404 may not try to interact with the user 402. Accordingly, the sensor unit 116 captures the event as 'eye gaze movement' only. Upon capturing the event, the event detection unit 117 determines the event satisfies the predetermined rules in the above table corresponding to event 1, as described earlier, i.e., by determining whether the gaze is constant for 15 seconds.

Figure 4C:
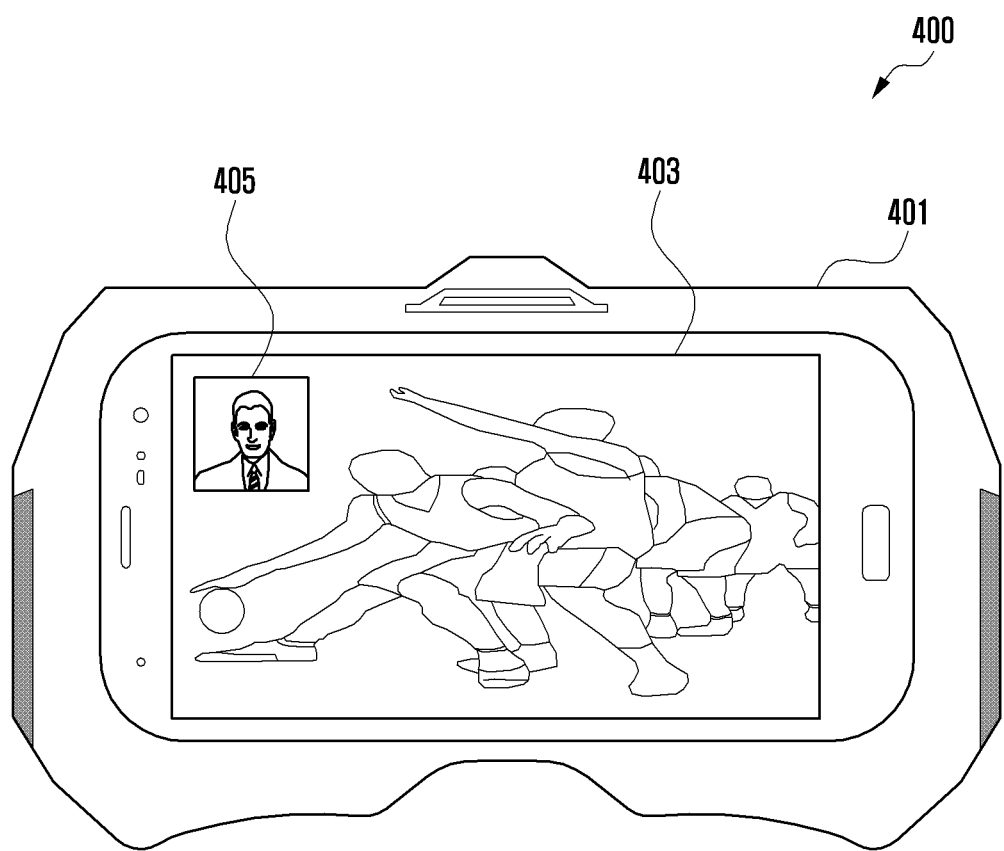

Accordingly, referring to FIG. 4C, the rendering unit 118 presents a real time image 405 of the real world environment, i.e., the secondary person in PIP mode, based on rules corresponding to event 1 on the VR enabled display unit 106. The rendering unit 118 removes the real time image 405 upon expiry of 45 seconds as described earlier.

In an alternative situation, the secondary person 404 tries to initiate an interaction with the user 402 upon gazing at the user 402 by calling name of the user 402 as Hey ABC, what are you watching? (represented by reference numerals 1 & 2). In one scenario, the secondary person 404 may call the name of the user 402 and gaze at the user 402 simultaneously. In another scenario, the secondary person 404 may gaze at the user 402 and then call the name of the user 404 after a delay of few seconds, say 15 seconds. Accordingly, the sensor unit 116 captures the event as 'eye gaze movement' and 'audio input'. Upon capturing the event, the event detection unit 117 determines the event satisfies the predetermined rules in the above table corresponding to events 1 & 2, as described earlier, i.e., by determining whether the gaze is constant for 15 seconds and whether the audio/speech of the secondary user 404 includes pre-stored phrase 'ABC'.

Figure 4D:
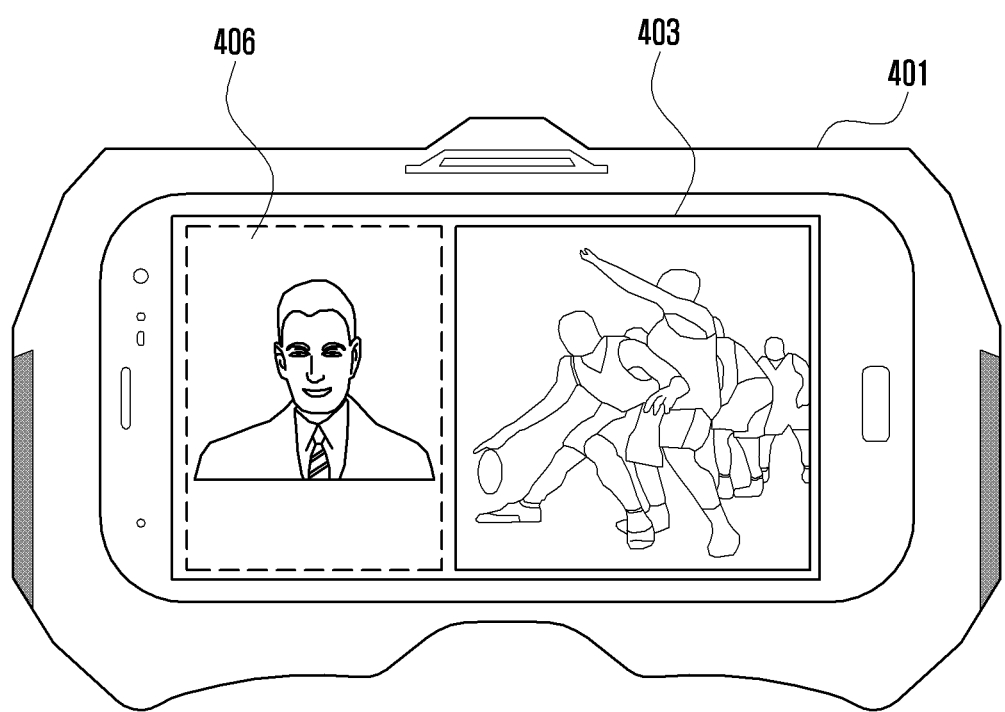

Accordingly, referring to FIG. 4D, the rendering unit 118 presents a real time video 406 of the real world environment, i.e., the secondary person 404 in split screen mode based on rules corresponding to event 2. In the split screen mode, the rendering unit 118 splits a screen area of the VR enabled display unit 106 into two portions (represented by dashed square and non-dashed square), with one portion displaying the real time image 406 and other portion displaying on-going VR content 403

In response to the presentation of the real time video 406, the user 402 may not interact with the secondary 404. In such scenario, the rendering unit 118 removes the real time video 406 upon expiry of 45 seconds as described earlier. Alternatively, the user 402 may interact with the secondary 404 by replying as Hey TBZ, how are you? (represented by reference numerals 1, 2, & 3). In such scenario, the event detection unit 117 detects the audio/voice pattern of the user 402 and continues presenting the real time video 406. Thereafter, the user 402 may terminate the interaction and use phrase bye (represented by reference numerals 1, 2, 3, & 4). The event detection 117 detects the phrase as view-time event and removes the real time video 406.

FIGS. 5A, 5B, 5C, and 5D illustrate third example 500 of displaying of information from real world environment on a VR device 501, in accordance with an embodiment of the present invention. The VR device 501 includes the units as described in reference to FIGS. 1A and 1B.

Figure 5A:
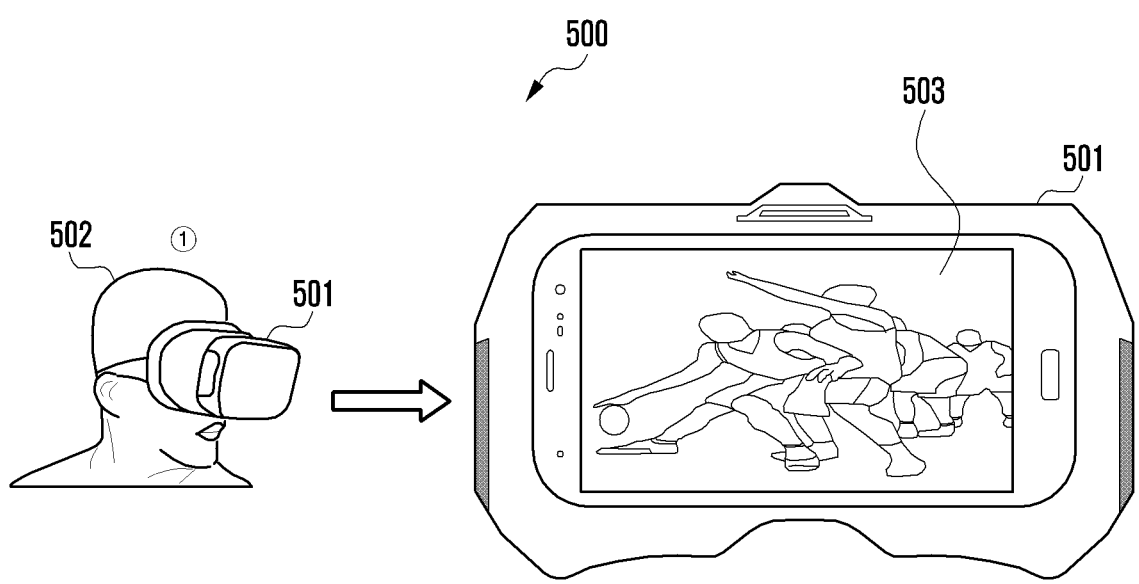

Referring to FIG. 5A, a user 502 wears the VR device 501 and the rendering unit 118 renders a VR content 503 on the VR enabled display unit 106. Initially, the user 502 is facing a first direction, represented by numeral one (1). Additionally, the user 502 may be unable to hear any external audio in a real world environment as the user 502 is wearing earphones (represented by a circle). The below table indicates the predetermined rules set in the example:

| | |
|---|---|
| Event 1 | Audio Input |
| Parameter 1.1 | Audio generated by an object |
| Threshold Value 1.1 | NA |
| Type of Information 1 | Text Notification |
| Display Mode 1 | Overlay |
| View-time event 1 | 45 seconds |
| Event 2 | Movement of VR device |
| Parameter 2.1 | Speed of movement |
| Threshold Value 2.1 | High |
| Type of Information 2 | Real Time Image |
| Display Mode 2 | Sectional |
| View Time-Out Event | Movement of VR device |

Figure 5B:
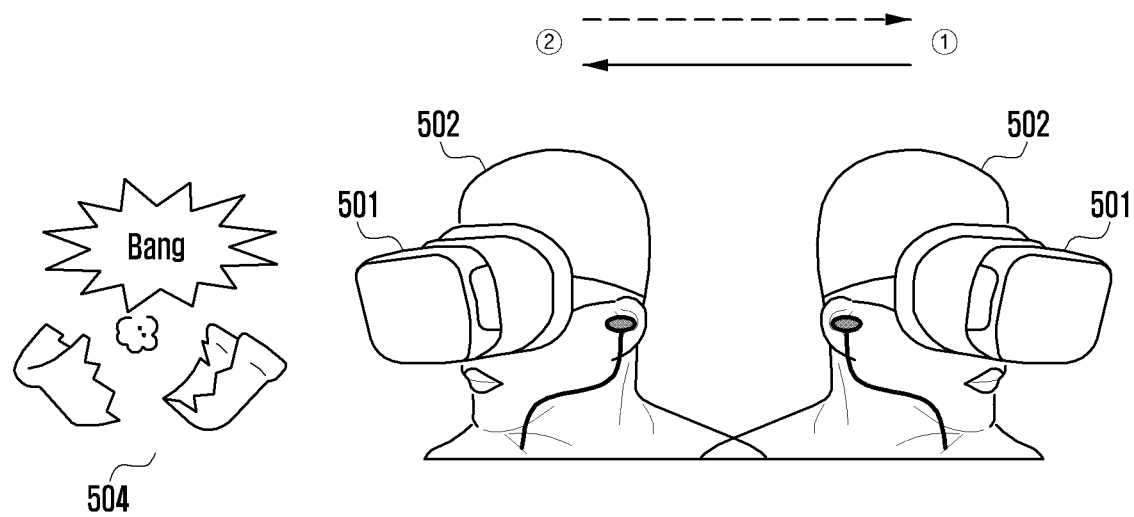

Referring to FIG. 5B, an object 504 may generate an audio in the real world environment. The object 504 can be a flowerpot and the audio is generated when the flowerpot falls and breaks. The audio may be generated in a second direction (represented by numeral one (2)), opposite to the first direction. The sensor unit 116 captures the event as 'audio input' in the real world environment, i.e., audio generated by the object 504. Upon capturing, the event detection unit 117 determines the event satisfies the predetermined rules in the above table as described earlier.

Figure 5C:
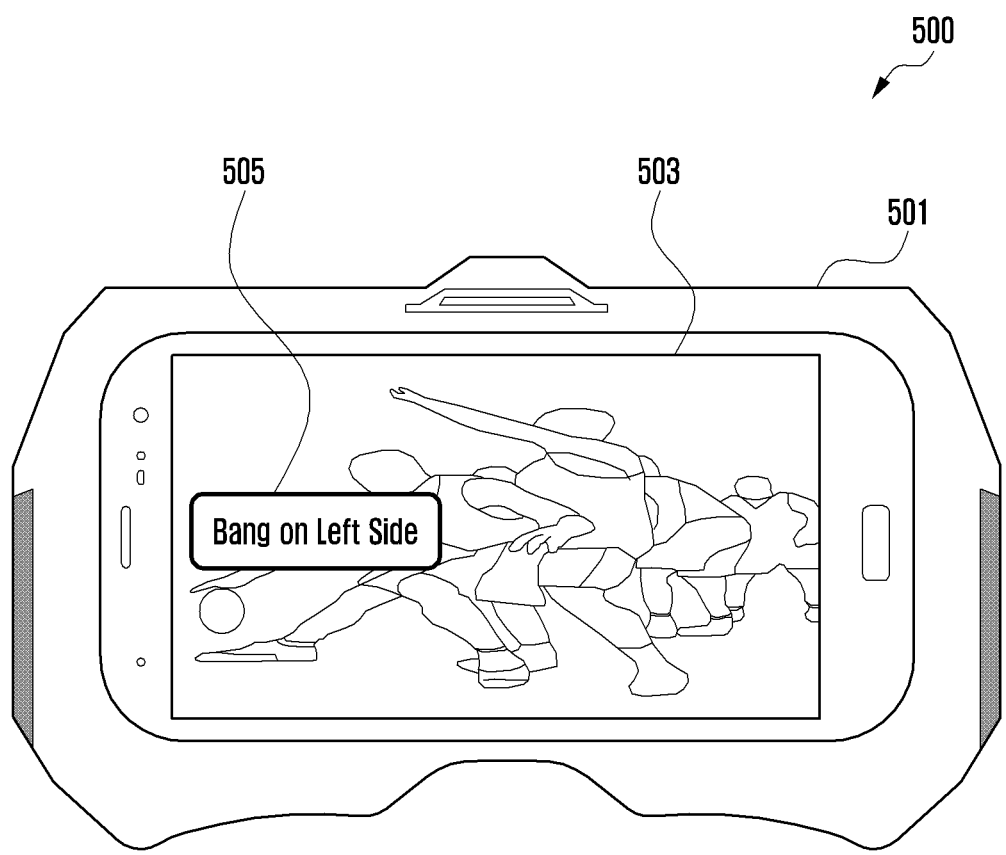

Accordingly, referring to FIG. 5C, the rendering unit 118 determines the direction associated with the audio and determines a position on the VR enabled display unit 106 as 'left side of the screen'. The rendering unit 118 then presents a text notification 505 in an overlay mode at the 'left side of the screen' indicating a sound originated in said direction. Further, the rendering unit 118 removes the text notification 505 upon expiry of 45 seconds as described earlier.

Additionally, or alternatively, referring to FIG. 5B again, the user 502 may spontaneously move the VR device 501 to the second direction by moving the head in the second direction in response to the text notification 505. The movement of the VR device 501 from the first direction to the second direction is represented by directional arrow. Accordingly, the sensor unit 116 captures the event as 'movement of VR device'. Upon capturing the event, the event detection unit 117 determines the event satisfies the predetermined rule in the above table as described earlier, i.e., whether movement of VR device was high.

Figure 5D:
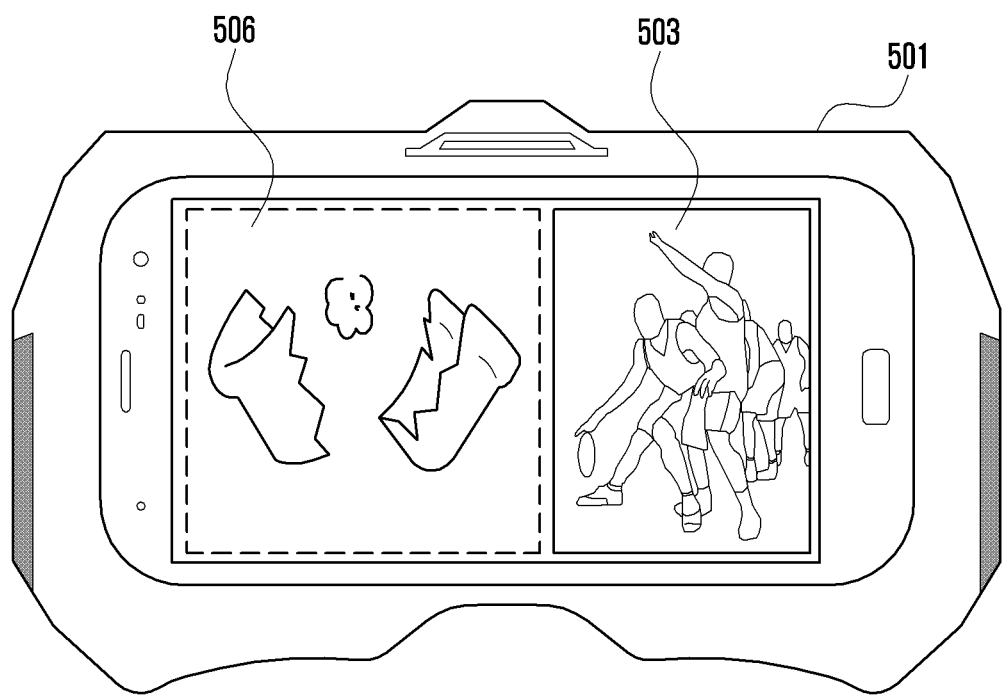

Accordingly, referring to FIG. 5D, the rendering unit 118 presents a real time image 506 of the real world environment, i.e., the object 504, in sectional mode (represented in dashed square). In the sectional mode, the real time image 506 occupies a larger area then the ongoing VR content 503.

Further, referring to FIG. 5B again, the user 502 may subsequently move the VR device 501 to the first direction from the second direction. The movement of the VR device 501 from second direction to first direction is represented by directional dashed arrow. Accordingly, the event detection unit 117 determines the movement of the VR device from second direction to the first direction as the view time-out event. Consequently, the rendering unit 118 removes the real time image 506 from the VR enabled display unit 106 and only the VR content is displayed, as illustrated in FIG. 5A.

FIGS. 6A, 6B, 6C, 6D illustrate fourth example 600 of displaying of information from real world environment on a VR device 601, in accordance with an embodiment of the present invention. The VR device 601 includes the units as described in reference to FIGS. 1A and 1B.

Figure 6A:
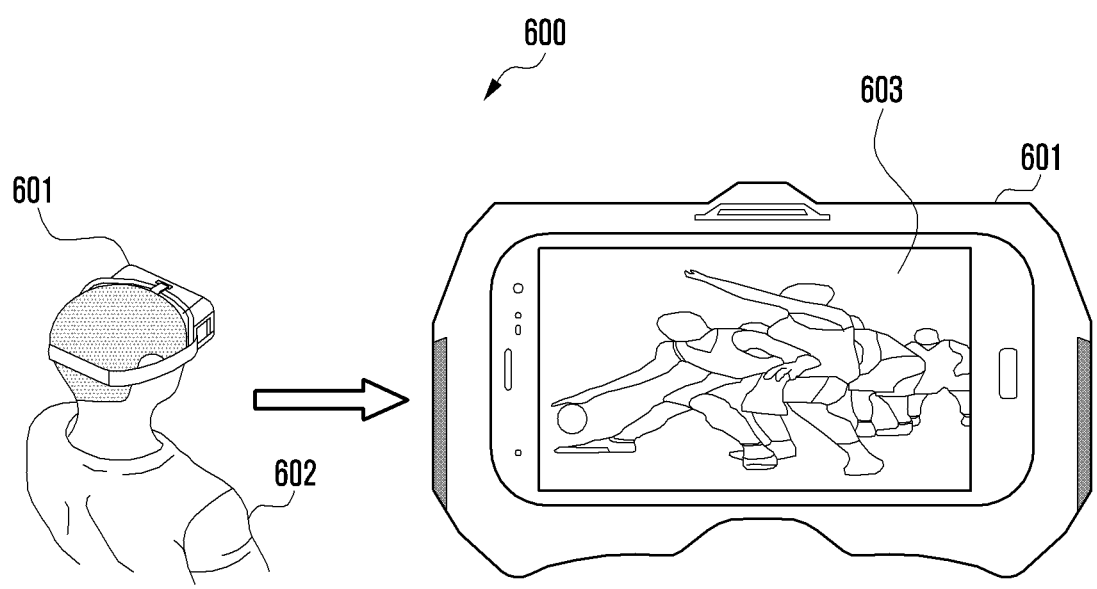

Referring to FIG. 6A, a user 602 wears the VR device 601 and the rendering unit 118 renders a VR content 603 on the VR enabled display unit 106. The below table indicates the predetermined rules set in the example:

| | |
|---|---|
| Event | Proximity of a person |
| Parameter 1 | Proximity/Distance |
| Threshold Value 1 | 2.5 meters |
| Parameter 2 | Face of the person |
| Threshold Value 2 | Pre-stored Image |
| Type of Information | Text Notification; Real Time Video |
| Display Mode | Sectional |
| View Time-Out Event | 25 seconds |

Figure 6B:
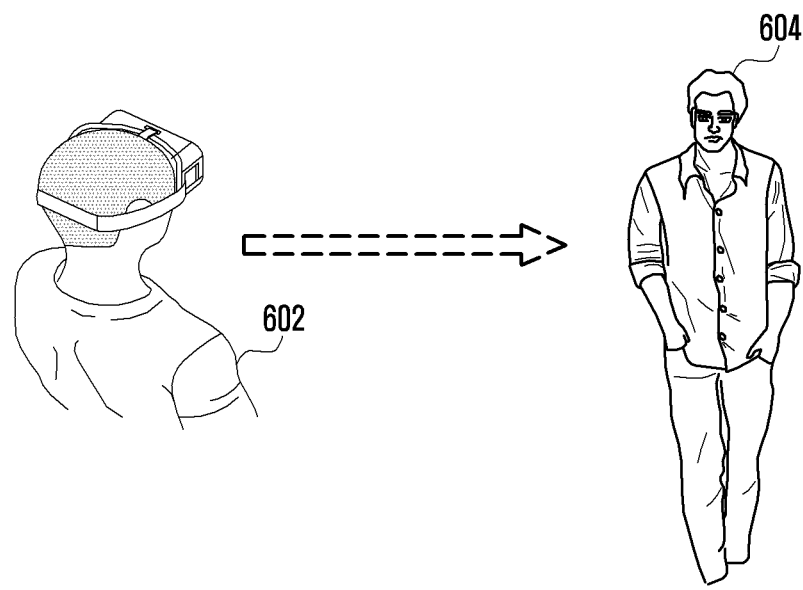

Referring to FIG. 6B, a secondary user 604 may pass by the VR device 601 in a real world environment. Accordingly, the sensor unit 116 captures the event as 'Proximity of a person' and a distance of the secondary user 604 from the VR device 601. Upon capturing the event, the event detection unit 117 determines the event satisfies the predetermined rules in the above table as described earlier, i.e., by determining whether the secondary user 604 is within the 5 meters distance. The distance is represented by directional dashed arrow.

Figure 6C:
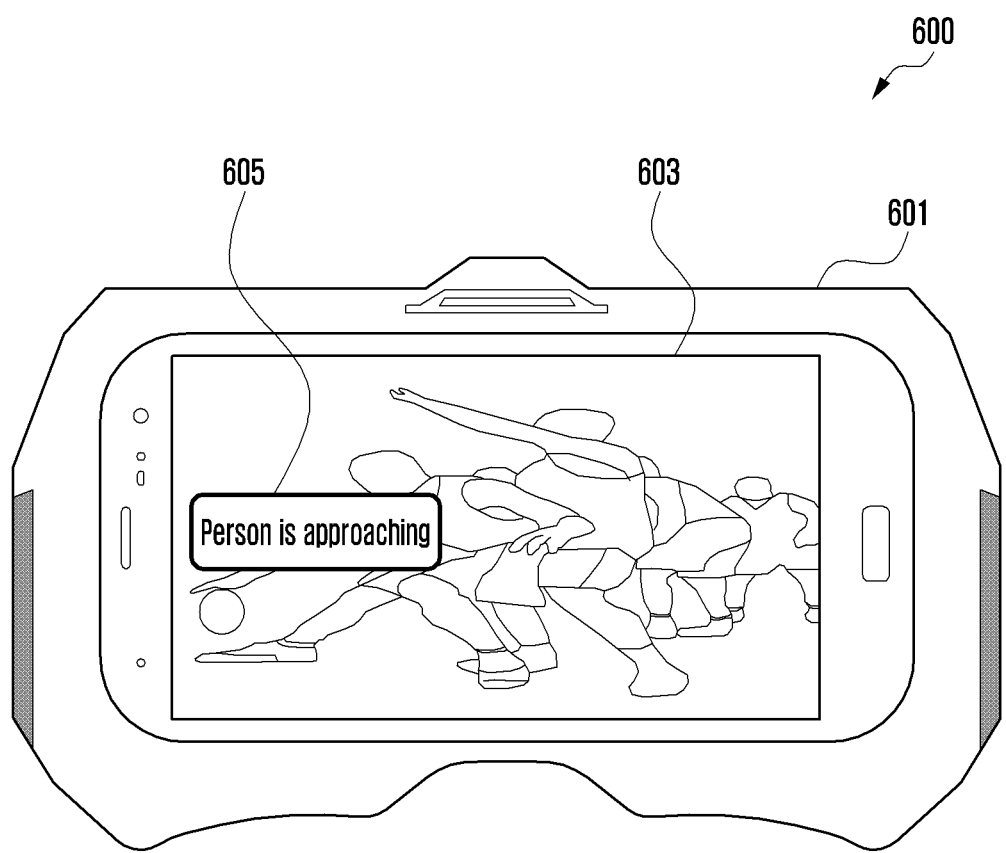
Figure 6D:
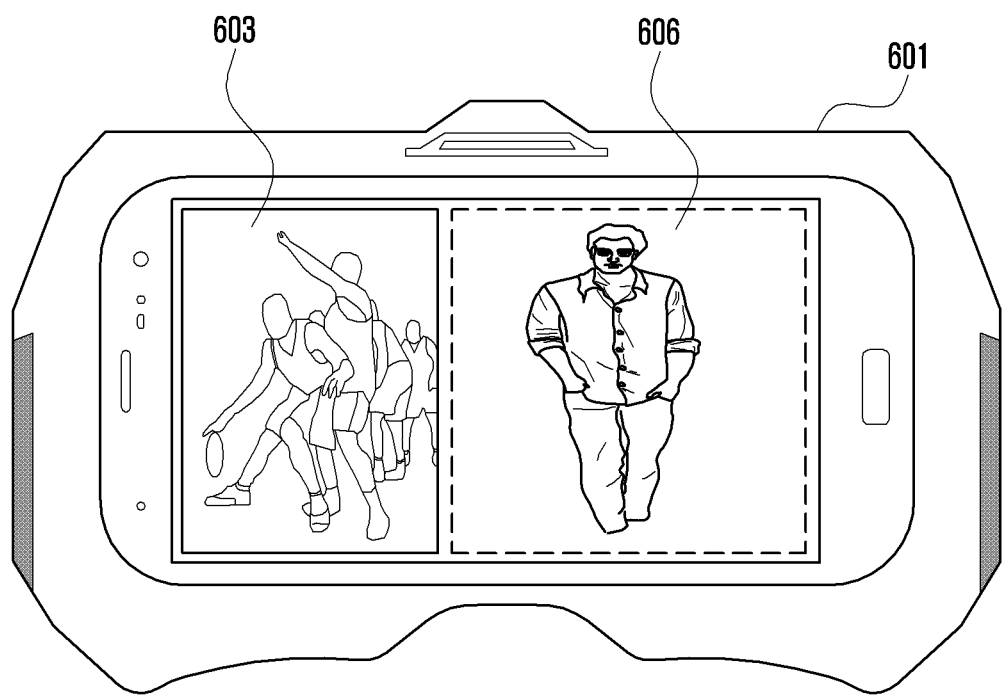

Additionally, the sensor unit 116 may capture an image of the secondary user 604. As such, the event detecting unit 117 may perform a comparison of the image with pre-stored images to identify the secondary user 604 is a 'known person' or 'unknown person'. When the secondary user 604 is identified as an 'unknown person' and is within 5 meters distance, the rendering unit 118 presents a text notification 605 indicating the secondary person 604 is approaching, as illustrated in FIG. 6C. However, when the secondary user 604 is identified as a 'known person' and is within the 5 meters distance, the rendering unit 118 presents a real time video 606 of the secondary user 604, as illustrated in FIG. 6D. The rendering unit 118 presents the real time video 606 in sectional mode such that the real time video 606 occupies a larger area then the ongoing VR content 603.

Further, the event detection unit 117 set a timer to 25 seconds. Upon expiry of the 25 seconds, the event detection unit 117 sends an instruction to the rendering unit 118 to delete or remove the real time video 606. Accordingly, the rendering unit 118 removes the real time video 606 and/or the text notification 605 from the VR enabled display unit 106 and only the VR content is displayed as illustrated in FIG. 6A. FIGS. 7A, 7B, and 7C illustrate fifth example 700 of displaying of information from real world environment on a VR device 701, in accordance with an embodiment of the present invention. The VR device 701 includes the units as described in reference to FIGS. 1A and 1B.

Referring to FIG. 7A, a user 702 wears the VR device 701 and the rendering unit 118 renders a VR content 703 on the VR enabled display unit 106. The user has created a profile with predetermined rules as below:

| Event | Proximity of an object |
| Parameter 1 | Proximity/Distance |
| Threshold Value 1 | 10 meters |
| Parameter 2 | Speed |
| Threshold Value 2 | 40 kmph |
| Type of Information | Directional Cue, Real Time Video |
| Display Mode | Sectional |

Referring to FIG. 7B, a secondary user 704 might throw an object 705 in a real world environment. In the example, the secondary user 704 is a player playing baseball and the object 705 is a ball. The object 705 or the ball may be moving in direction of the user 702, represented by directional dashed arrow. Accordingly, the sensor unit 116 captures the event as 'Proximity of an object', a distance of the object 705 from the VR device 701, and a speed of the object 705. Upon capturing the event, the event detection unit 117 determines the change in distance and speed of the moving object 705. Accordingly, the event detection unit 117 determines the event satisfies the predetermined rules in the above table as described earlier. Further, the rendering unit 118 determines a direction of the moving object 704 towards the user 702.

Accordingly, referring to FIG. 7C, the rendering unit 118 presents real time video 706 of the real world environment, i.e., the movement of the object 705. The rendering unit 118 presents the real time video 706 in sectional mode such that the real time video 706 occupies a larger area then the ongoing VR content 703. Further, the rendering unit 118 displays a directional cue 707 indicating to move in a direction opposite to the direction of the moving object 705.

FIGS. 8A, 8B, 8C, 8D, and 8E illustrate sixth example 800 of displaying of information from real world environment on a VR device 801, in accordance with an embodiment of the present invention. The VR device 101 includes the units as described in reference to FIGS. 1A and 1B.

Figure 8A:
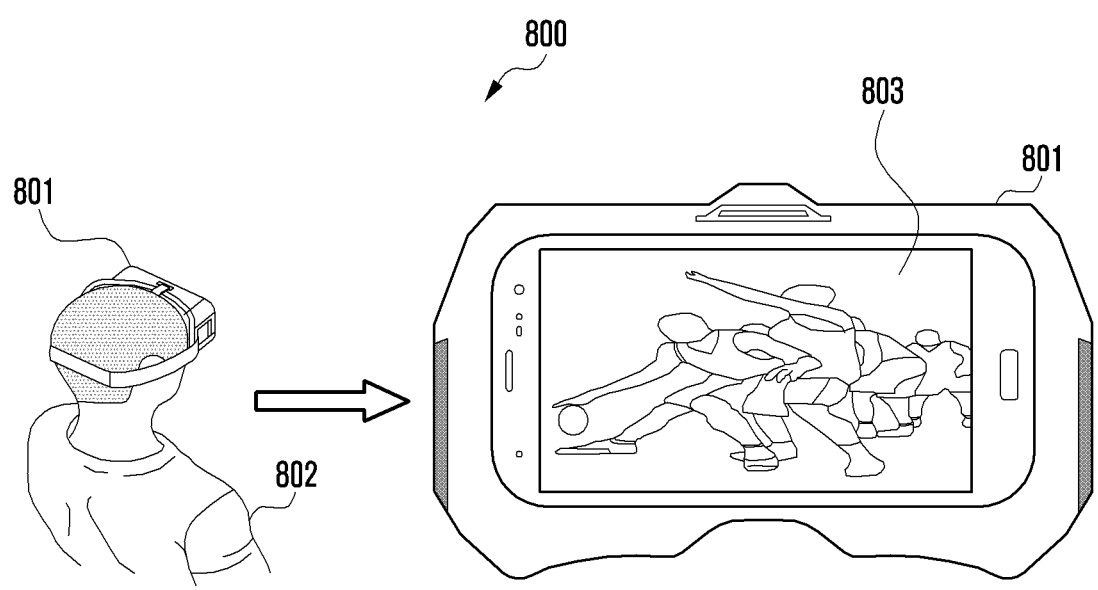

Referring to FIG. 8A, a user 802 wears the VR device 801 and the rendering unit 118 renders a VR content 803 on the VR enabled display unit 106. Additionally, the user 802 may be unable to hear any external audio in a real world environment. The below predetermined rules are set in the example:

| Event 1 | Audio Input |
| Parameter 1.1 | Phrase |
| Value 1.2 | ABC Name of the User |
| Type of Information | Real Time Image |
| Display Mode | Split |
| Event 2 | Movement of the VR device |
| Parameter 2.1 | Direction |
| Value 2.1 | Direction of Audio Input |
| Type of Information | Text Notification |
| Display Mode | Overlay |

Figure 8B:
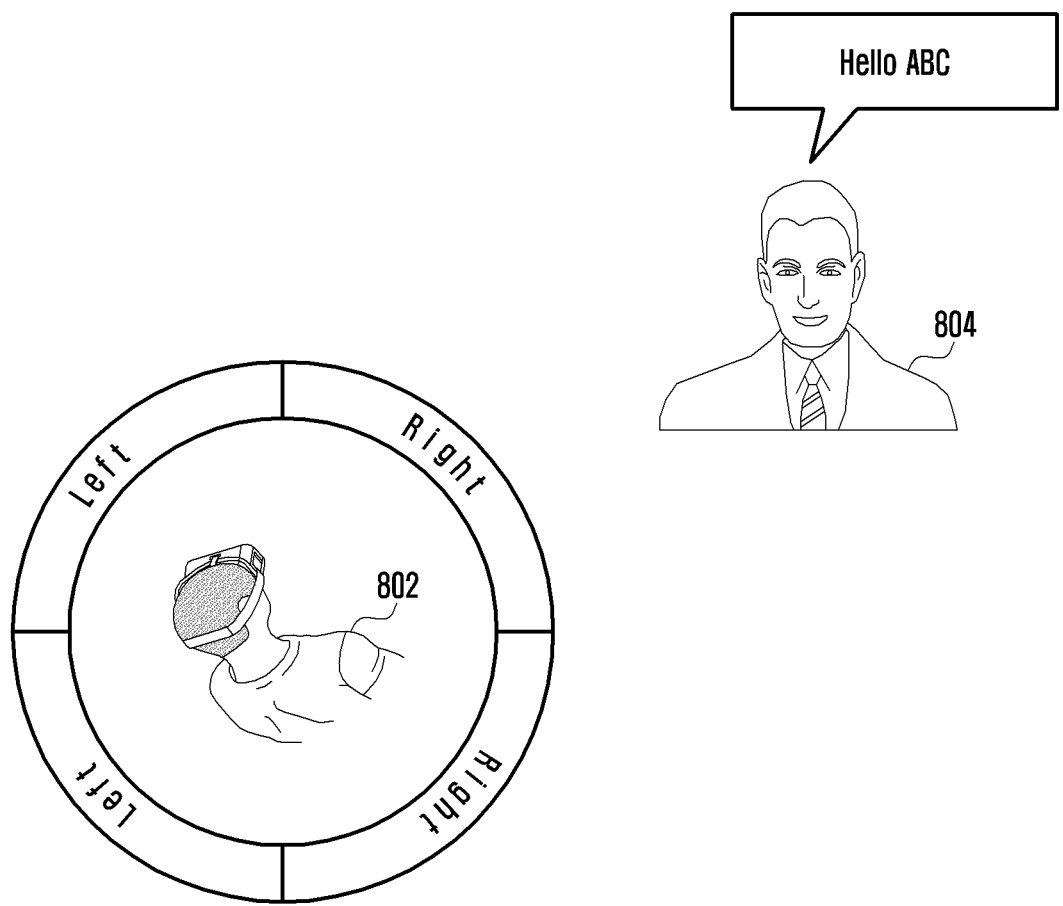

Referring to FIG. 8B, secondary user 804 in a real world environment calls the user 802 using his name ABC, while the user 802 is viewing the VR content on the VR device 101. Accordingly, the sensor unit 116 captures the event as 'audio input'. Upon capturing the event, the event detection unit 117 determines the event satisfies the predetermined rules related to event 1 in the above table as described earlier, i.e., whether the secondary user 804 is calling name of the user 802. Further, the rendering unit 118 determines a direction of the audio input. Accordingly, the rendering unit 118 determines a position on the VR enabled display unit 106 based on the direction. In the figure, the direction is determined as 'towards right of the user' and consequently the position is determined as 'right side of the screen'. Further, the rendering unit 118 determines a display area lesser than an area for the displaying the on-going VR content 803.

Figure 8C:
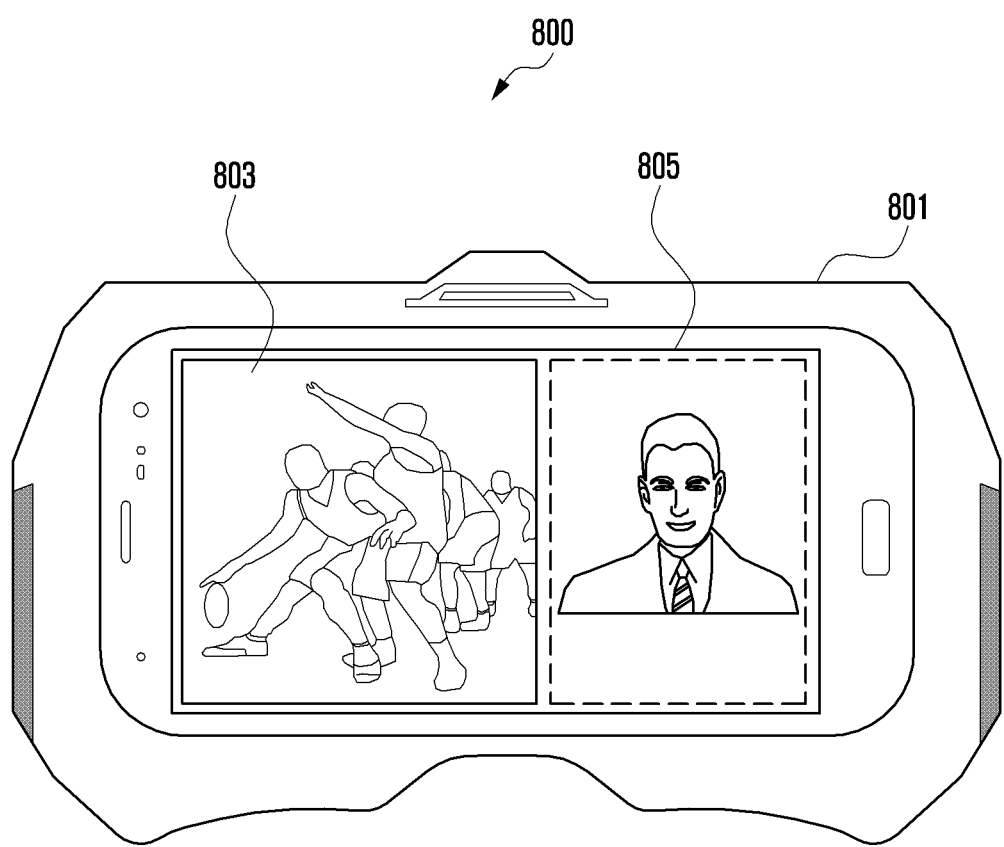
Figure 8D:
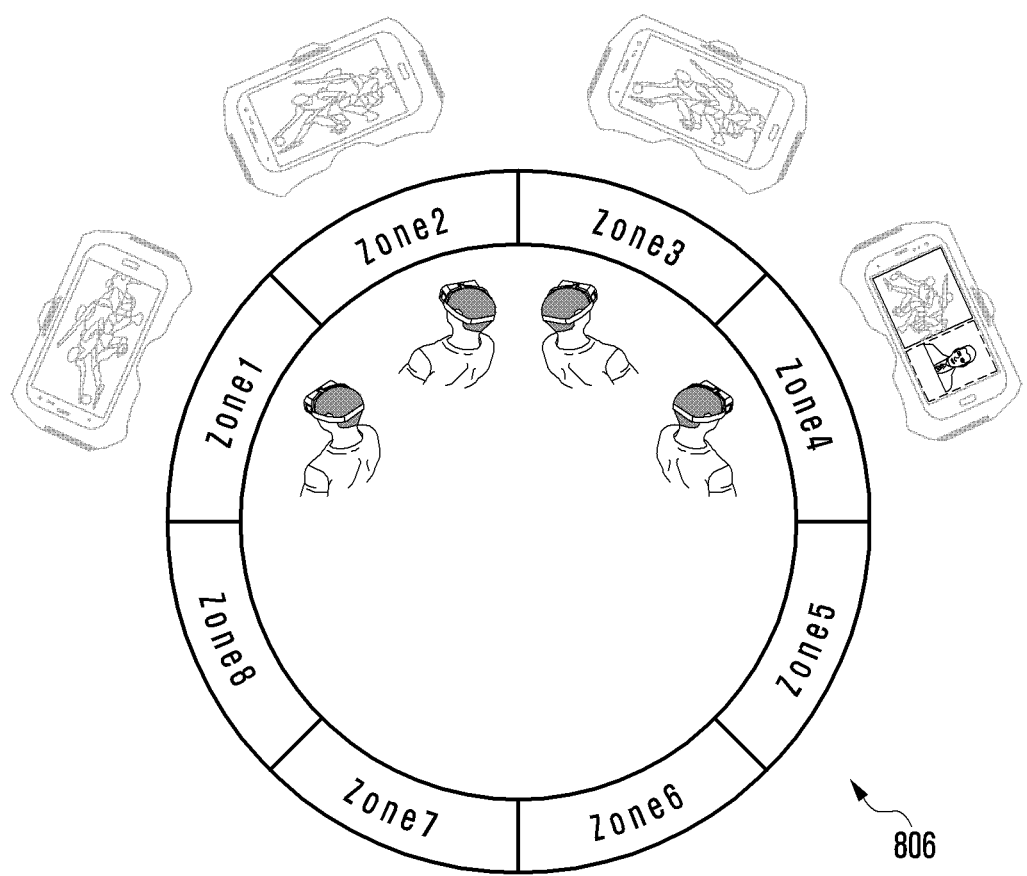

Accordingly, referring to FIG. 8C, the rendering unit 118 presents a real time image 805 of the real world environment, i.e., the secondary person, at the determined position, i.e., 'towards right of the user'. Further, the rendering unit 118 presents the real time image 805 in split screen mode such that screen area of the VR enabled display unit 106 is split into two portions (represented by dashed square and non-dashed square), with one portion displaying the real time image 805 and other portion displaying on-going VR content 803. In the figure, a display area of the portion displaying real time image 805 is lesser than a display area of the portion displaying the on-going VR content 803.

Furthermore, the event detection unit 117 creates virtual circular zones around VR device 801 to map the direction of the audio input with the virtual circular zones. Thus, the event detection unit 117 determines the event satisfies the predetermined rules related to event 2 when the VR device 801 is present in the virtual circular zone mapping the direction of the audio input. Accordingly, referring to FIG. 8D, virtual circular zones 806 is created with eight zones namely, zone 1 to zone 8, such that zone 4 is mapped with the direction of the audio input, i.e., 'towards right of the user'. The virtual circular zone 806 can be created as having a diameter of few meters covering the distance between the user 802 and the secondary user 804. As illustrated, when the VR device 801 is present in zone 1, zone 2, and zone 3, the real time image 805 is not displayed. However, when the VR device 801 is present in zone 4, the real time image 805 is displayed.

Figure 8E:
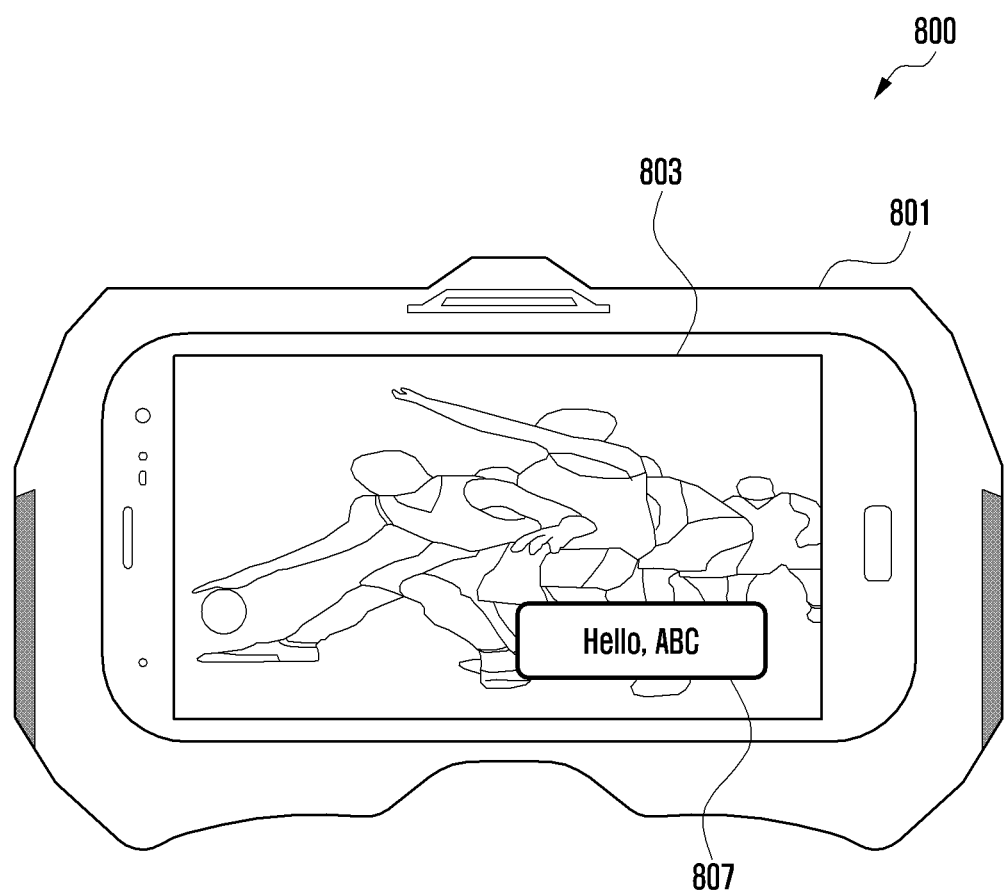

Referring to FIG. 8E, the rendering unit 118 can further display a text notification 807. Accordingly, the event detection unit 117 converts the captured audio into text using speech-to-text conversion techniques as known in the art. Upon converting, the rendering unit 118 displays the text notification 807 at the determined position, i.e., 'towards right of the user' in an overlay mode.

In a similar manner, the event detection unit 117 can set a reminder based on the converted text and sets a period for display of the reminder. The rendering unit 118 displays the reminder upon expiry of the period.

FIGS. 9A, 9B, 9C, 9D, 9E, and 9F illustrate seventh example 900 of displaying of information from real world environment on a VR device 901 and controlling presentation of the information based on user gestures, in accordance with an embodiment of the present invention. The VR device 101 includes the units as described in reference to FIGS. 1A and 1B.

Figure 9A:
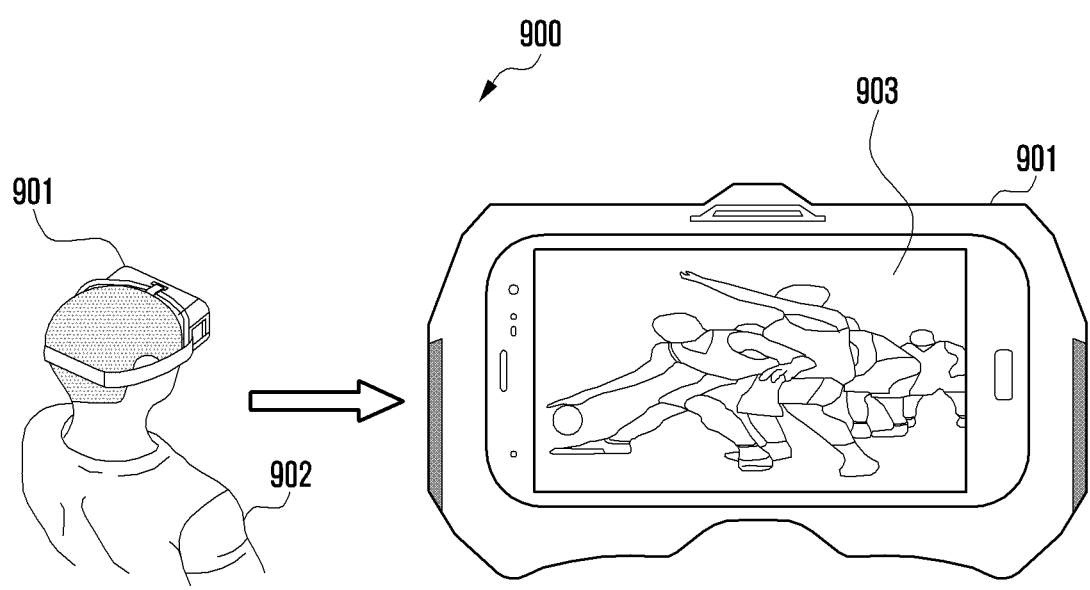

Referring to FIG. 9A, a user 902 wears the VR device 901 and the rendering unit 118 renders a VR content 903 on the VR enabled display unit 106. The below table indicates the predetermined rules set in the example:

| Event | Gesture Input |
|---|---|
| Parameter 1 | Shape of Gesture |
| Value 1.1 | Pair of Inverted L - Real time video in PIP mode |
| Value 1.2 | Pinch out - Zoom Real time video |
| Value 1.3 | Swipe horizontal right - Move Real time video towards right of the screen |
| Value 1.4 | Swipe vertical up - Move Real time video towards top of the screen |
| Value 1.5 | Thumbs-up - Delete Real time video |

Figure 9B:
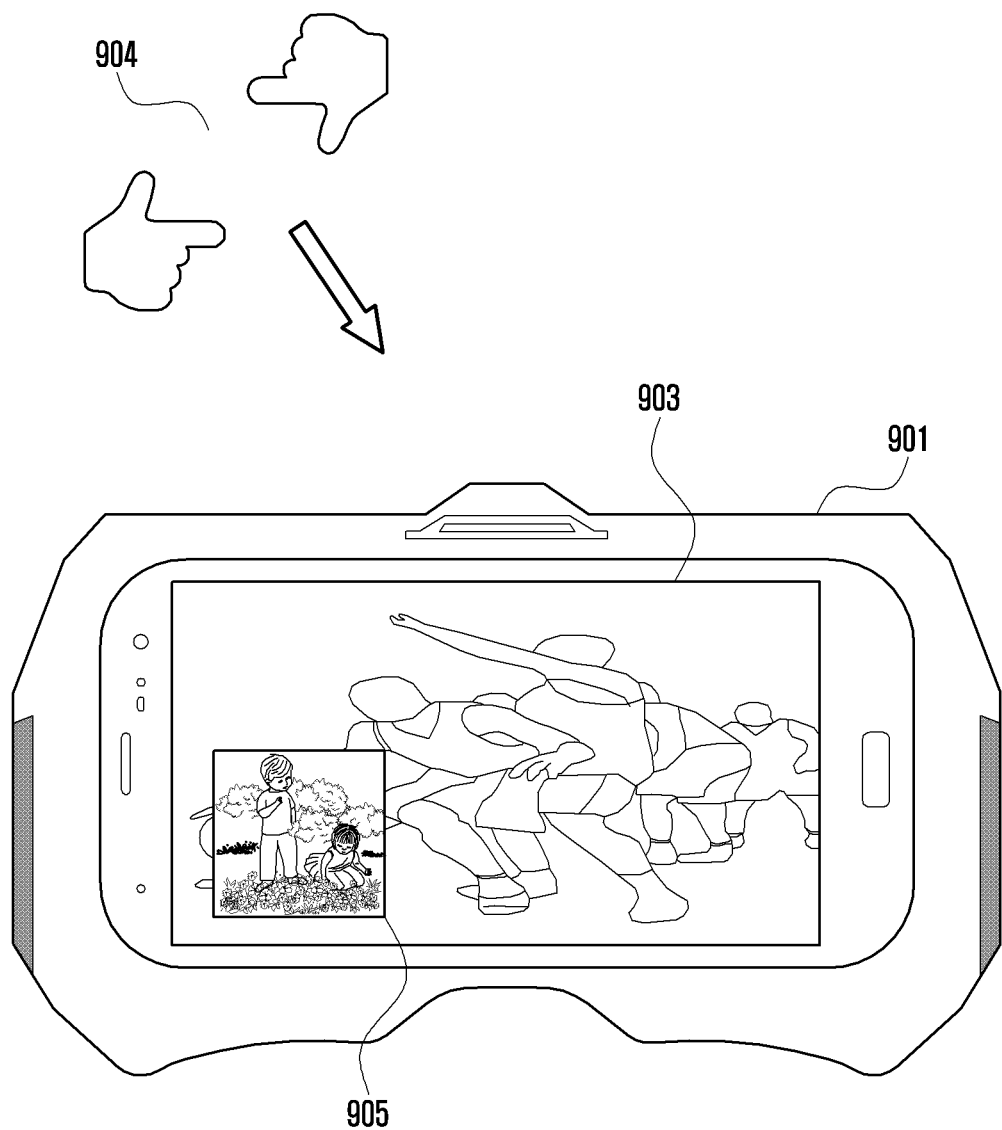

Referring to FIG. 9B, the user 902 may provide gesture input 904 having shape as 'pair of inverted L'. The event detection unit 117 determines the gesture input 904 satisfies the corresponding rule in the above table and the rendering unit 118 presents a real time video 905 of real world environment, i.e., children playing in a garden in PIP mode at left side of the screen on the display unit 106.

Figure 9C:
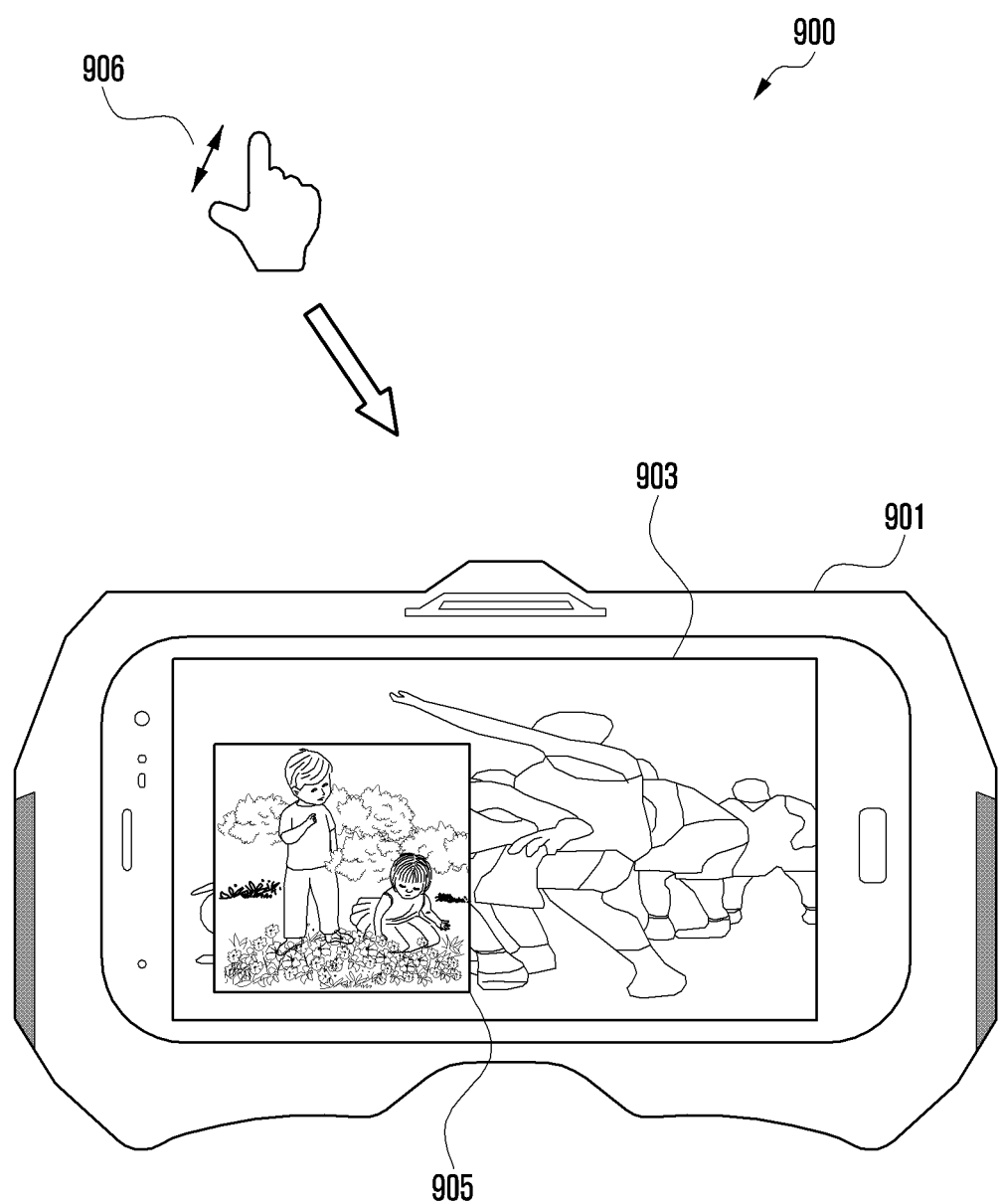

Referring to FIG. 9C, the user 902 may provide gesture input 906 having shape as 'pinching out'. The event detection unit 117 determines the gesture input 906 satisfies the corresponding rule in the above table and the rendering unit 118 increases a display area of the real time video 905, i.e., zoom out.

Figure 9D:
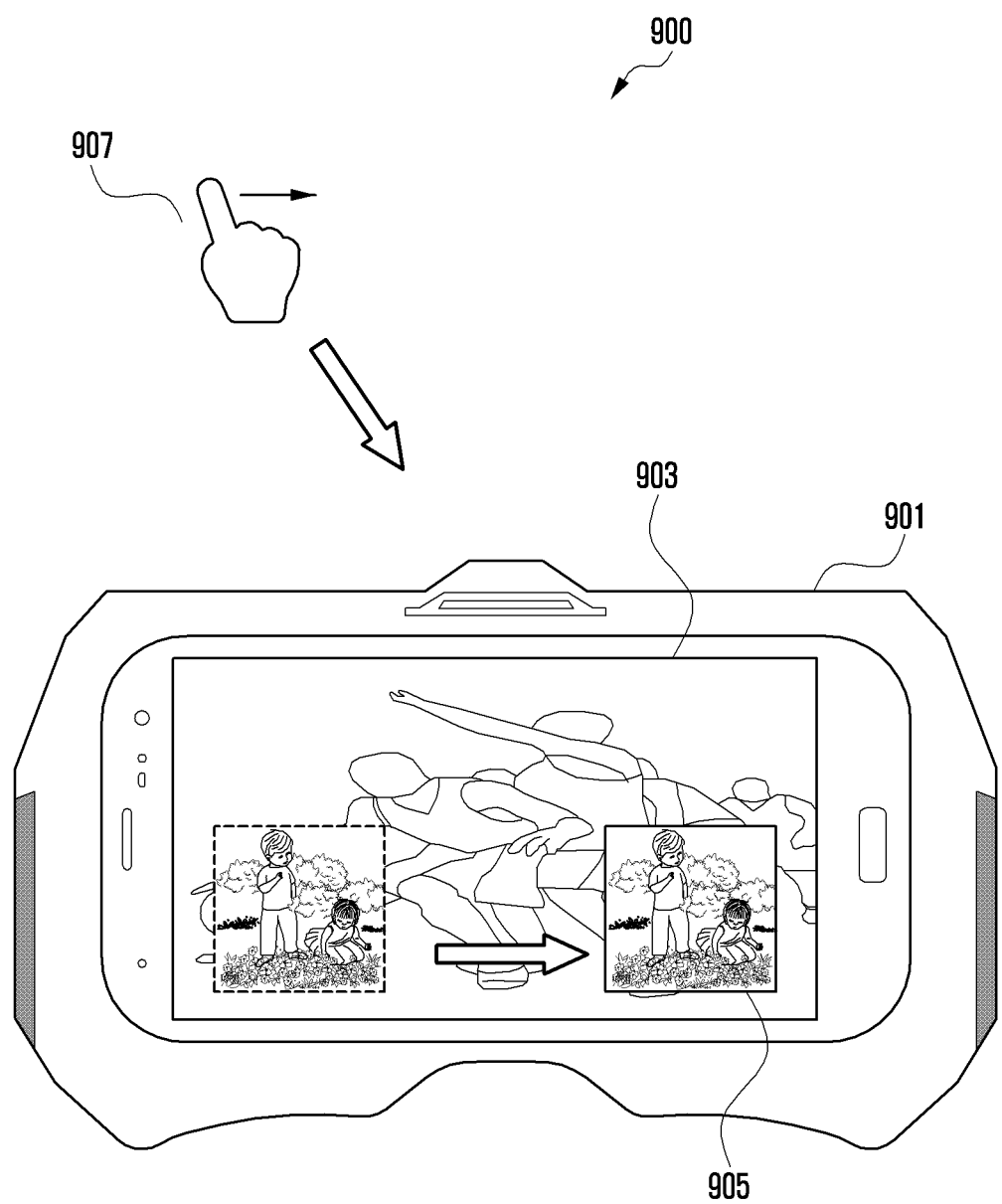

Referring to FIG. 9D, the user 902 may provide gesture input 907 having shape as 'swiping towards horizontal right'. The event detection unit 117 determines the gesture input 907 satisfies the corresponding rule in the above table and the rendering unit 118 moves the real time video 905 towards right side of the screen (represented by solid arrow).

Figure 9E:
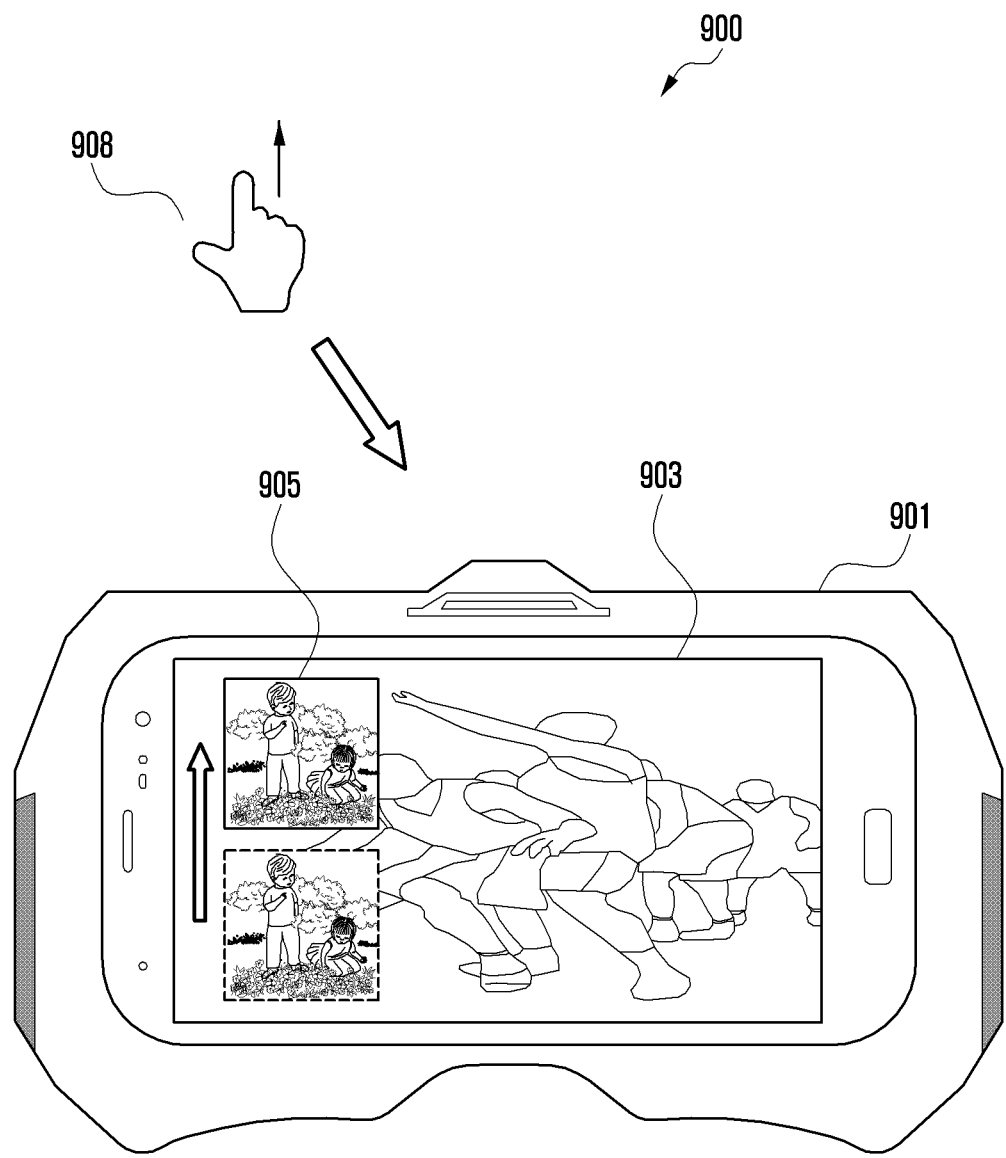

Referring to FIG. 9E, the user 902 may provide gesture input 908 having shape as 'swiping towards vertical up'. The event detection unit 117 determines the gesture input 908 satisfies the corresponding rule in the above table and the rendering unit 118 moves the real time video 905 towards top of the screen (represented by solid arrow).

Figure 9F:
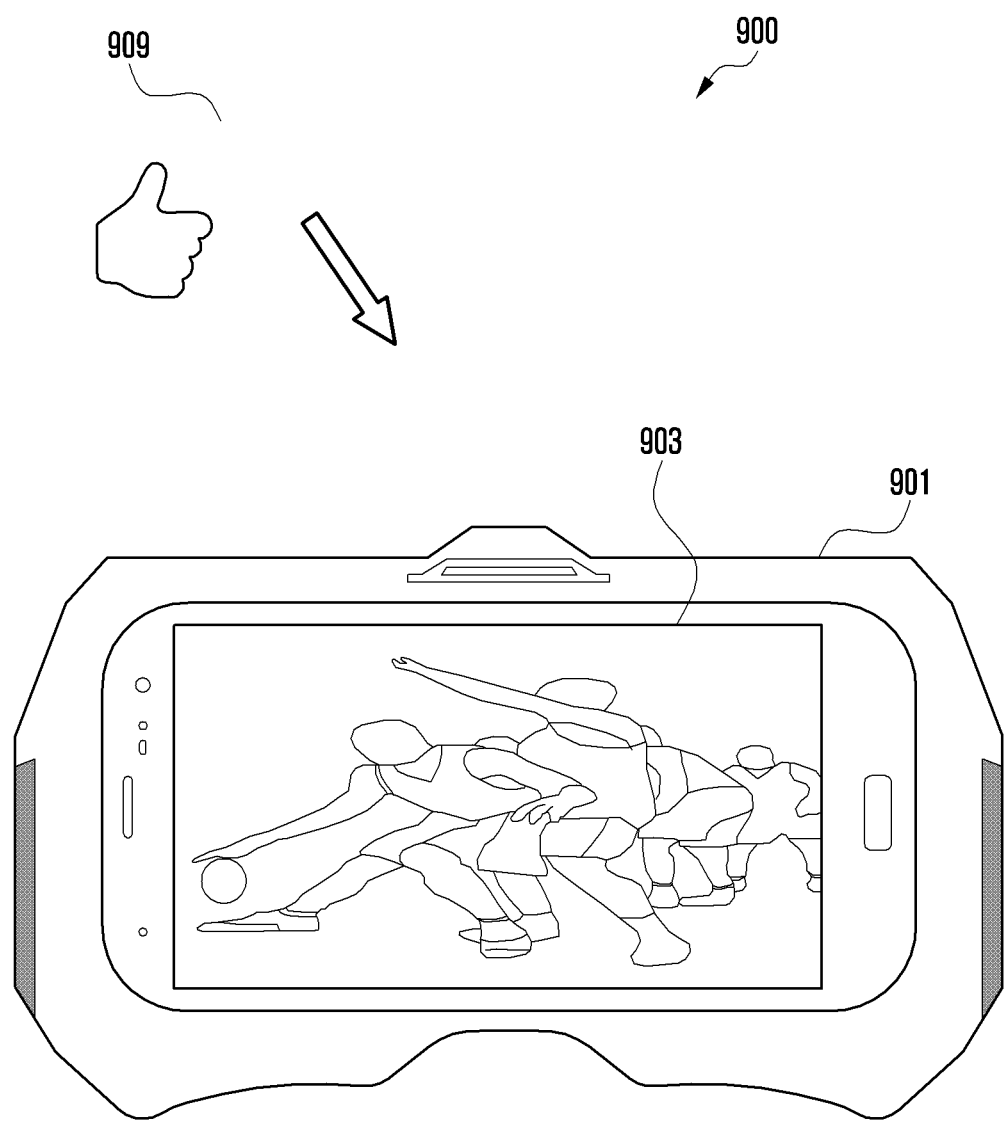

Referring to FIG. 9F, the user 902 may provide gesture input 909 having shape as 'thumbs-up' (represented by OK icon). The event detection unit 117 determines the gesture input 909 satisfies the corresponding rule in the above table and the rendering unit 118 deletes the real time video 905 towards top of the screen and renders only the VR content 903, as illustrated in FIG. 9A.

FIGS. 10A, 10B, and 10C illustrate eighth example 1000 of displaying of different information from real world environment on a VR device 1001 for different users, in accordance with an embodiment of the present invention. The VR device 1001 includes the units as described in reference to FIGS. 1A and 1B.

Referring to FIG. 10A, a user 1002 and a user 1003 wears the VR device 1001 and the rendering unit 118 renders a VR content 1004 on the VR enabled display unit 106. As would be understood, the user 1002 and the user 1003 will wear the VR device 1001 at separate instances.

The below table indicates the predetermined rules set in the example by the user 1002:

TABLE 1

| Event | Proximity of a person |
|---|---|
| Parameter | Proximity/Distance |
| Threshold Value | 2.5 meters |
| Type of Information | Real Time Video |
| Display Mode | Sectional |

The below table indicates the predetermined rules set in the example by the user 1003:

TABLE 2

| Event | Proximity of a person |
|---|---|
| Parameter | Proximity/Distance |
| Threshold Value | 2.5 meters |
| Type of Information | Real Time Image |
| Display Mode | Overlay |

The above rules are saved as profiles of the users 1002 and 1003, and are fetched by the event detection unit 117 for analysing captured events.

A secondary user 1005 may pass by the users 1002 & 1003 in a real world environment. Accordingly, the sensor unit 116 captures the event as 'Proximity of a person' and a distance of the secondary user 1005 from the VR device 1001. When the user 1002 is wearing the VR device 1001, the event detection unit 117 fetches a profile 1006, which includes the predetermined rules as shown in above table 1, and determines the event satisfies the predetermined rules in the profile 1006 as described earlier. Accordingly, the rendering unit 118 presents a real time video 1007 in sectional mode on the display unit 106, as illustrated in FIG. 10B.

Likewise, when the user 1003 is wearing the VR device 1001, the event detection unit 117 fetches a profile 1008, which includes the predetermined rules as shown in above table 2, and determines the event satisfies the predetermined rules in the profile 1007 as described earlier. Accordingly, the rendering unit 118 presents a real time image 1009 in an overlay mode on the display unit 106, as illustrated in FIG. 10C.

FIG. 11 illustrates an exemplary method 1100 for displaying of information on a virtual reality (VR) device, in accordance with an embodiment of the present invention. The order in which the method is described is not intended to be construed as a limitation, and any number of the described method blocks can be combined in any order to implement the method, or an alternative method. Additionally, individual blocks may be deleted from the method without departing from the spirit and scope of the subject matter described herein. Furthermore, the method can be implemented in any suitable hardware, software, firmware, or combination thereof.

At block 1101, an event in a real world environment is captured. For example, the sensor unit 116 captures the event.

At block 1102, a determination is made if the event thus captured satisfies at least one predetermined rule. Upon capturing the event, the event detection unit 117 fetches profile from the memory 104 and determines if the event or at least a parameter associated with the event satisfies the rule(s) saved in the fetched profile.

Upon negative determination, then method flows to block 1101, where the event(s) in the real world environment are continuously captured.

Upon positive determination, the method flows to block 1103. At block 1103, information pertaining to the captured event is presented on a VR enabled display unit. The information is presented without absolute interruption of an ongoing rendering of content on the VR enabled display unit. For example, the rendering unit 118 presents the information associated with the event on the VR enabled display unit 106 without absolute interruption of the on-going VR content.

At block 1104, a view-time event is detected. The view-time event is one of expiry of a predetermined time from a time of capturing of the event; movement of the VR device from a first position to a second position subsequent to capturing of the event; reception of predefined gesture input; and reception of predefined audio input. For example, the event detection unit 117 detects the view-time event.

At block 1105, the presentation of the information on the VR enabled display unit is controlled based on detection of said view-time event. For example, upon detection of the view-time event, the rendering unit 118 controls the presentation of the information on the VR enabled display unit 106.

FIG. 12 is a block diagram of a second electronic device 1200 according to various embodiments of the present invention.

Referring to FIG. 12, the second electronic device 1200 may be an external electronic device including the sensor unit 116 as illustrated in FIG. 1B. Example of such external electronic device includes, but not limited to, a head mounted device (HMD). The second electronic device 1200 may include at least one of a micro controller unit (MCU) 1210, a communication module 1220, a sensor module 1230, an input module 1240, an eye tracking module 1250, a vibrator 1252, an adjustable optics module 1254, a power management module 1260, and a battery 1262.

The MCU 1210 may be a controller of the second electronic device 1200, for controlling other components (for example, the communication module 1220, the sensor module 1230, the input module 1240, the eye tracking module 1250, the vibrator 1252, the adjustable optics module 1254, and the power management module 1260) by driving an operating system (OS) or an embedded software program. The MCU 1210 may include a processor and a memory.

The communication module 1220 may electrically connect other electronic device (for example, the VR device 101) to the second electronic device 1200 by wired or wireless communication and perform data transmission and reception between the electronic devices. According to an embodiment, the communication module 1220 may include a USB module 1221, a WiFi module 1222, a BT module 1223, an NFC module 1224, and a GPS module 1225. According to an embodiment, at least three of the USB module 1221, the WiFi module 1222, the BT module 1223, the NFC module 1224, and the GPS module 1225 may be included in a single integrated chip (IC) or IC package.

The sensor module 1230 may measure a physical property or sense an operation state of the second electronic device 1200 and convert the measured or sensed information to an electrical signal. The sensor module 1230 may include at least one of, for example, an accelerometer 1231, a gyro sensor 1232, a geomagnetic sensor 1233, a magnetic sensor 1234, a proximity sensor 1235, a gesture sensor 1236, a grip sensor 1237, a biometric sensor 1238, and an access sensor 1239. The second electronic device 1200 may sense a head motion of a user wearing the second electronic device 1200, using at least one of the accelerometer 1231, the gyro sensor 1232, and the geomagnetic sensor 1233. The second electronic device 1200 may sense whether the second electronic device 1200 is worn or removed, using the proximity sensor 1235 or the grip sensor 1237. According to an embodiment, the second electronic device 1200 may determine whether the user wears the second electronic device 1200 by at least one of Infrared (IR) recognition, pressure recognition, and sensing of a capacitance (or dielectric constant) variation involved in wearing of the second electronic device 1200. The gesture sensor 1236 may sense a hand or finger motion of the user and receive the hand or finger motion as an input to the second electronic device 1200. The second electronic device 1200 may sense proximity of an object to the user by the proximity sensor 1235. Alternatively or additionally, the sensor module 1230 may include a biometric sensor such as an e-node sensor, an Electromyography (EMG) sensor, an Electroencephalogram (EEG) sensor, an Electrocardiogram (ECG) sensor, an iris sensor, and a finger print sensor and thus may recognize vital information about the user. The sensor module 1230 may further include a control circuit for controlling at least one of internal sensors.

The input module 1240 may receive an input from the user. The input module 1240 may include a touch pad 1241 and a button 1242. The touch pad 1241 may recognize a touch input in at least one of a capacitive manner, a resistive manner, an IR manner, and an ultrasonic manner. The touch pad 1241 may further include a control circuit. If the touch pad 1241 operates in the capacitive manner, the touch pad 1241 may recognize a physical contact or proximity. The touch pad 1241 may further include a tactile layer. In this case, the touch pad 1241 may provide a tactile response to the user. The button 1242 may be, for example, a physical button, an optical key, or a keypad.

The power management module 1260 may manage power of the second electronic device 1200. While not shown, the power management module 1260 may include, for example, a power management integrated circuit (PMIC), a charger IC, or a battery fuel gauge.

The PMIC may be mounted, for example, on an IC or a system on a chip (SOC) semiconductor. A battery may be charged wiredly or wirelessly. The charger IC may charge the battery and prevent introduction of overvoltage or overcurrent from a charger. According to an embodiment, the charger IC may operate wiredly and/or wirelessly. Wireless charging may be performed, for example, by magnetic resonance, magnetic induction, or electromagnetic waves. A circuit for wireless charging, for example, a coil loop, a resonance circuit, or a rectifier may be added.

The battery fuel gauge may measure, for example, a charge level, a voltage while charging, a current, or temperature of the battery 1262. The battery 1262 may store electricity and supply power. The battery 1262 may include a rechargeable battery or a solar battery.

The eye tracking module 1250 may track the eyes of the user by at least one of an electrical ocular graph (EOG) sensor, a coil system, a dual purkinje system, a bright pupil system, and a dark pupil system. Further, the eye tracking module 1250 may include a micro camera for tracking the eyes.

The adjustable optics module 1254 may measure an inter-pupil distance (IPD) of the user so that the user may view an image suitable for the user's sight. The second electronic device 1200 may adjust the distance between lenses according to the IPD of the user measured by the adjustable optics module 1254. The second electronic device 1200 may transmit the IPD of the user measured by the adjustable optics module 1254 to the first electronic device to adjust a displayed position of a screen on the display of the first electronic device.

The MCU 1210 may transmit a motion signal sensed through the motion sensor of the sensor module 1230 and transmit the motion signal to the first electronic device. The motion sensor may be at least one of the accelerometer 1231, the gyro sensor 1232, and the geomagnetic sensor 1233.

The MCU 1210 may sense access of an object to the user of the second electronic device 1200 through the access sensor 1239 and transmit an access sensing signal to the first electronic device. The MCU 1210 may measure a direction from which the object accesses the user of the second electronic device 1200 through the access sensor 1239 and transmit information indicating the direction to the first electronic device.

The access sensor 1239 may be a space recognition sensor such as an IR sensor, an ultrasonic sensor, a radio frequency (RF) sensor, or a radar. A Wisee sensor or an Allsee sensor may be used as the RF sensor. According to an embodiment, a wireless communication module may be used as the access sensor 1239. The wireless communication module may be at least one of the WiFi module 1222, the BT module 1223, the NFC module 1224, and the GPS module 1225. When an object accesses the second electronic device, the received signal strength of a wireless communication signal received at the wireless communication module may get weak. If the received signal strength is fast dropped by a value larger than a predetermined threshold while the user of the second electronic device is stationary, the MCU 1210 may determine that the object is accessing. In addition, the MCU 1210 may determine a direction in which the received signal strength is fast dropped by the value larger than the predetermined threshold to be a direction from which the object is accessing.

FIG. 13 illustrates a block diagram of a first electronic device 1300 according to various embodiments of the present invention or that includes a VR device to which a method for displaying of information from real world environment is applicable. The electronic device 1300 may be, for example, a whole or a part of the VR device 101 illustrated in FIG. 1A.

Referring to FIG. 13, the electronic device 1300 may include one or more application processors (APs) 1330, a communication module 1320, a subscriber identification module (SIM) card 1324, a memory 1330, a sensor module 1340, an input device 1350, a display 1370, an interface 1170, an audio module 1380, a camera module 1391, a power management module 1395, a battery 1396, an indicator 1397, and a motor 1398.

The AP 1330 may have a configuration equal or similar to the processor 133 as described in FIG. 1A. The AP 1330 may control one or more hardware or software components that are connected to the AP 1330 by executing an OS or an application program and may perform processing or computation of various types of data including multimedia data. The AP 1330 may be implemented, for example, as a SoC). According to an embodiment, the AP 1330 may further include a graphics processing unit (GPU; not shown). The AP 1330 may also include at least some of the components of the VR management module 118 as illustrated in FIG. 1B.

The communication module 1320 may have a configuration equal or similar to the communication interface 117 as described in FIG. 1A. The communication module 1320 may transmit and receive data in communication between the electronic device 1300 and other electronic devices. According to an embodiment, the communication module 1320 may include a cellular module 1321, a WiFi module 1323, a BT module 1325, a GPS module 1327, an NFC module 1328, and a RF module 1329.

The cellular module 1321 may provide services such as voice call, video call, SMS, or the Internet, via a communication network (for example, LTE, LTE-A, CDMA, WCDMA, UMTS, WiBro, or GSM). The cellular module 1321 may identify and authenticate electronic devices within a communication network, using a SIM card (for example, the SIM card 1324). According to an embodiment, the cellular module 1321 may perform at least a part of the functionalities of the AP 1330. For example, the cellular module 1321 may perform at least a part of multimedia control functionality.

According to an embodiment, the cellular module 1321 may include a communication processor (CP). The cellular module 1321 may, for example, be implemented as SoC. Although components such as the cellular module 1321 (for example, the CP), the memory 1330, or the power management module 1395 are shown in FIG. 18 as configured separately from the AP 1330, the AP 1330 may include, or be integrated with, one or more of the foregoing components (for example, the cellular module 1321).

According to an embodiment, the AP 1330 or the cellular module 1321 (for example, the CP) may process instructions or data received from at least one of a non-volatile memory or other components by loading the instructions or the data in a volatile memory. In addition, the AP 1330 or the cellular module 1321 may store at the non-volatile memory at least one of data received from at least one of other components or data generated by at least one of the other components.

Each of the WiFi module 1323, the BT module 1325, the GPS module 1327, and the NFC module 1328 may include, for example, a processor that may process data received or transmitted by the respective modules. Although FIG. 18 shows the cellular module 1321, the WiFi module 1323, the BT module 1325, the GPS module 1327, and the NFC module 1328 as separate components, any combination (for example, two or more) of the cellular module 1321, the WiFi module 1323, the BT module 1325, the GPS module 1327, and the NFC module 1328 may be included in an IC or an IC package according to an embodiment. For example, at least some of the processors corresponding to the respective cellular module 1321, the WiFi module 1323, the BT module 1325, the GPS module 1327, or the NFC module 1328 may be implemented as a single SoC. For example, a CP corresponding to the cellular module 1321 and a WiFi processor corresponding to the WiFi module 1323 may be implemented as a single SoC.

The RF module 1329 may transmit and receive data, for example, RF signals. While not shown, the RF module 1329 may include a transceiver, a power amplifier module (PAM), a frequency filter, or a low noise amplifier (LNA). The RF module 1329 may further include one or more components for transmitting and receiving electro-magnetic (EM) waves in free space, such as conductors or conductive wires. Although FIG. 18 shows that the cellular module 1321, the WiFi module 1323, the BT module 1325, the GPS module 1327, and the NFC module 1328 share the single RF module 1329, at least one of the cellular module 1321, the WiFi module 1323, the BT module 1325, the GPS module 1327, or the NFC module 1328 may transmit and receive RF signals via a separate RF module according to an embodiment.

The SIM card 1324 may be a card including a SIM, and may be configured to be inserted into a slot disposed at a specified location of the electronic device. The SIM card 1324 may include a unique identifier (for example, integrated circuit card identifier (ICCID)) or subscriber information (for example, international mobile subscriber identity (IMSI)).

The memory 1330 may include an internal memory 1332 or an external memory 1334. The internal memory 1332 may be at least one of, for example, a volatile memory (for example, dynamic RAM (DRAM), static RAM (SRAM), or synchronous Dynamic RAM (SDRAM)) or a non-volatile memory (for example, one time programmable ROM (OTPROM), programmable ROM (PROM), erasable and programmable ROM (EPROM), electrically erasable and programmable ROM (EEPROM), mask ROM, flash ROM, NAND flash memory, or NOR flash memory).

According to an embodiment, the internal memory 1332 may be a solid state drive (SSD). The external memory 1334 may be, for example, a flash drive (for example, a compact flash (CF) drive, a secure digital (SD), a micro secure digital (micro-SD), a mini secure digital (mini-SD), an extreme digital (xD), or a Memory Stick). The external memory 1334 may be operatively coupled to the electronic device 1300 via various interfaces. According to an embodiment, the electronic device 1300 may further include recording devices (or recording media) such as a hard disk drive (HDD). In one implementation, the internal memory 1332 may have a configuration equal or similar to the memory 114 as described in FIG. 1A.

The sensor module 1340 may measure physical properties or detect operational states associated with the electronic device 1300, and convert the measured or detected information into electric signals. The sensor module 1340 may have a configuration equal or similar to the sensor unit 137 as described in FIG. 1A.

The sensor module 1340 may include at least one of, for example, a gesture sensor 1340A, a gyro sensor 1340B, an atmospheric pressure sensor 1340C, a magnetic sensor 1340D, an accelerometer sensor 1340E, a grip sensor 1340F, a proximity sensor 1340G, a color sensor 1340H (for example, a red, green, blue (RGB) sensor), a biometric sensor 1340I, a temperature/humidity sensor 1340J, an illuminance sensor 1340K, or an ultra violet (UV) sensor 1340M. Additionally or alternatively, the sensor module 1340 may include, for example, an electrical-nose sensor (not shown), an EMG sensor (not shown), an EEG sensor (not shown), an IR sensor (not shown), an iris sensor (not shown), or a finger print sensor. The sensor module 1340 may further include a control circuit for controlling one or more sensors included therein.

The input device 1350 may include a touch panel 1352, a (digital) pen sensor 1354, a key 1356, or an ultrasonic input device 1358. The touch panel 1352 may detect a touch input using at least one of, for example, capacitive, resistive, infrared, and ultrasonic methods. The touch panel 1352 may further include a control circuit. A capacitive-type touch panel may detect physical touch inputs or proximity inputs. The touch panel 1352 may further include a tactile layer, which may provide haptic feedback to the user.

The (digital) pen sensor 1354 may be implemented, for example, using methods identical to or similar to receiving a touch input from a user, or using a separate detection sheet. The key 1356 may include, for example, a physical button, an optical key, or a keypad. The ultrasonic input device 1358 may be a device configured to identify data by detecting, using a microphone (for example, a microphone 1388), ultrasonic signals generated by a device capable of generating the ultrasonic signal. The ultrasonic input device 1358 may detect data wirelessly. According to an embodiment, the electronic device 1300 may receive a user input from an external device (for example, a computer or a server) connected to the electronic device 1300 using the communication module 1320. The input device 1350 may further have a configuration equal or similar to the VR enabled input unit 325 as described in FIG. 3B.

The display module 1370 may include a panel 1372, a hologram device 1374, or a projector 1376. The panel 1372 may be, for example, a LCD or an active-matrix organic light-emitting diode (AM-OLED) display. The panel 1372 may be configured to be, for example, flexible, transparent, or wearable. The panel 1372 and the touch panel 1352 may be implemented as a single module. The hologram device 1374 may utilize the interference of light waves to provide a three-dimensional image in empty space. The projector 1376 may provide an image by projecting light on a display. The display may be positioned, for example, inside or outside the electronic device 1300. According to an embodiment, the display module 1370 may further include a control circuit for controlling the panel 1372, the hologram device 1374, or the projector 1376. The display module 1370 may further have a configuration equal or similar to the VR enabled display unit 306 as described in FIG. 3A.

The interface 1170 may include, for example, a high-definition multimedia interface (HDMI) 1172, a USB 1174, an optical interface 1176, or a D-sub 1178. Additionally or alternatively, the interface 1170 may include, for example, a mobile high-definition link (MHL) interface, an SD/Multi-Media Card, or an infrared data association (IrDA) interface. The interface 1170 may be incorporated into, for example, the communication interface 307 as described in FIG. 3A.

The audio module 1380 may encode/decode a voice into an electrical signal, and vice versa. At least a part of components of the audio module 1380 may be incorporated in, for example, the I/O interface 135 as described in FIG. 1A. The audio module 1380 may process audio information input into, or output from, for example, a speaker 1382, a receiver 1384, an earphone 1386, or the microphone 1388.

The camera module 1391 may capture still images or a video. According to an embodiment, the camera module 1391 may include one or more image sensors (for example, a front sensor or a rear sensor), a lens (not shown), an image signal processor (ISP, not shown), or a flash (for example, a LED or a Xenon lamp, not shown). Examples of the camera module 1391 include, but not limited to, 3D camera, depth camera, and infrared camera.

The power management module 1395 may manage power of the electronic device 1300. While not shown, the power management module 1395 may include, for example, a PMIC, a charger IC, or a battery or fuel gauge.

The PMIC may be disposed, for example, in an IC or a SoC semiconductor. The charging method for the electronic device 1300 may include wired or wireless charging. The charger IC may charge a battery, or prevent excessive voltage or excessive current from a charger from entering the electronic device 1300. According to an embodiment, the charger IC may include at least one of a wired charger IC or a wireless charger IC. The wireless charger IC may be, for example, a magnetic resonance type, a magnetic induction type or an electromagnetic wave type, and may include additional circuits for wireless charging, such as a coil loop, a resonance circuit, or a rectifier.

The battery gauge may measure, for example, a charge level, a voltage while charging, current, or temperature of the battery 1396. The battery 1396 may store or generate electricity and supply power to the electronic device 1300 using the stored or generated electricity. The battery 1396 may include, for example, a rechargeable battery or a solar battery.

The indicator 1397 may indicate one or more states (for example, boot status, message status, or charge status) of the electronic device 1300 or a part of the electronic device 1300 (for example, the AP 1330). The motor 1398 may convert an electrical signal into a mechanical vibration. While not shown, the electronic device 1300 may include a device for supporting mobile TV (for example, a GPU). The device for supporting mobile TV may process media data compliant with, for example, digital multimedia broadcasting (DMB), digital video broadcasting (DVB), or Media Flow.

Each of components of an electronic device described above according to the present disclosure may include one or more components, and each component's name may vary according to the type of the electronic device. The electronic device according to the present disclosure may include at least one of the above-described components, and some may be omitted or additional components may be included. In addition, some of the components of the hardware according to the present disclosure may be combined into a single component and perform functions identical to those of the respective components before their combination. Similarly, some of the components of the hardware according to the present disclosure may be split into a plurality of entities that collectively perform functions identical to those of the respective component before their split.

The term "module" as used herein may include its ordinary meaning including, but not limited to, for example, a unit of one, or a combination of two or more, hardware, software or firmware. The term "module" may be used interchangeably with a term such as unit, logic, logical block, component, or circuit. A module may be the smallest unit for performing one or more functions, or a portion thereof. A module may be implemented mechanically or electronically. For example, a module according to the present disclosure may include at least one of a known or to-be-developed application-specific integrated circuit (ASIC) chip, field-programmable gate array (FPGA) or programmable logic device that perform certain operations.

According to various embodiments, at least a part of devices (for example, modules or their functions) or methods (for example, operations) according to the present disclosure may be implemented, for example, in the form of a programming module, as commands stored in a non-transitory computer-readable storage medium. When a command is executed by one or more processors (for example, the processor 113), the one or more processors may execute a function corresponding to the command. The non-transitory computer-readable storage medium may be, for example, the memory 114. At least a part of the programming module may be implemented (for example, executed) by the processor 113. At least a part of the programming module may include, for example, a module, a program, a routine, a set of instructions, and/or a process to execute one or more functions.

The non-transitory computer-readable recording medium may include any kind of hardware device configured specially to store a program command (for example, a programming module). Examples of the hardware device may include magnetic media such as a hard disk, floppy disk, and a magnetic tape, optical media such as a compact disc read only memory (CD-ROM) and a digital versatile disc (DVD), magneto-optical media such as a optical disk, a ROM, a RAM, a flash memory, and the like. The program command may include a premium language code that can be executed in a computer using an interpreter as well as a mechanical code produced by a compiler. The above-mentioned hardware device may be implemented as one or more software modules to perform the operations of the present disclosure and vice versa.

While certain present preferred embodiments of the invention have been illustrated and described herein, it is to be understood that the invention is not limited thereto. Clearly, the invention may be otherwise variously embodied, and practiced within the scope of the following claims.

We claim:

1. A method for display of information on a virtual reality (VR) device, the method comprising:
   displaying at least one VR content on a screen of a VR enabled display unit;
   detecting at least one event in a real world environment;
   determining information corresponding to the detected at least one event; and
   dividing, if the detected at least one event satisfies at least one predetermined rule, the screen of the VR enabled display unit into at least two display areas including a first display area and a second display area, displaying continuously the at least one VR content on the first display area and displaying the determined information on the second display area,
   wherein the information includes at least one of a real time video depicting the real world environment and a real time image depicting the real world environment and is captured by at least one sensor unit of the VR device.

2. The method of claim 1, wherein the at least one event is detected by the at least one sensor unit, the at least one sensor unit comprising an eye-tracing sensor, a facial expression sensor, a touch panel, a vibrator, an optics module, an accelerometer, a gyroscope, a geomagnetic sensor, a magnetic sensor, a proximity sensor, a gesture sensor, a grip sensor, a biometric sensor, an access sensor, a camera module, an audio module, an atmospheric pressure sensor, a red, green, blue (RGB) sensor, a temperature sensor, a humidity sensor, a light sensor, a physiological sensor, a location/position detection sensor, or an ultraviolet (UV) sensor.

3. The method of claim 1, wherein the at least one event corresponds to a change within a predefined area in the real world environment surrounding the VR device and includes at least one of:
   a risk or a threat to a user of the VR device,
   a physiological state of the user of the VR device,
   a gesture input,
   an audio input,
   an eye gaze movement,
   a facial expression of a person proximate to the VR device,
   a movement of the VR device,
   a proximity of a person to the VR device,
   a proximity of an object to the VR device, or
   a sudden movement in proximity to the VR device.

4. The method of claim 1, wherein the at least one predetermined rule includes:
- the at least one event or at least one parameter associated with the at least one event is predefined in a memory;
- the at least one event or at least one parameter associated with the at least one event is specified by a user;
- at least one parameter associated with the event has a value higher than a predefined threshold value; and
- at least one parameter associated with the event has a constant value for a predefined threshold value of time.

5. The method of claim 1, wherein the determined information is displayed on the screen of the VR enabled display unit in one of: an overlay mode, a picture-in-picture mode, a split screen mode, a split view mode, and a sectional view mode.

6. The method of claim 1, wherein the information is displayed based on the at least one predetermined rule.

7. The method of claim 1, wherein the displaying the information comprises:
- determining a direction of the detected at least one event;
- determining a position on the VR enabled display unit based on the determined direction;
- selecting the first display area on the VR enabled display unit based on the determined position; and
- presenting the information at the first display area on the screen of the VR enabled display unit.

8. The method of claim 1, wherein the displaying the information comprises:
- determining at least one of a type of the detected at least one event, a priority level of the detected at least one event, or an application rendering the at least one VR content, based on the at least one predetermined rule;
- selecting the second display area on the VR enabled display unit based on the determined type; and
- presenting the information at the second display area on the screen of the VR enabled display unit.

9. The method of claim 1, further comprising:
- detecting a view-time event, the view-time event being one of:
  - expiry of a predetermined time from a time of capturing of the event;
  - a movement of the VR device from a first position to a second position subsequent to the detecting of the at least one event;
  - a reception of a predefined gesture input; or
  - a reception of a predefined audio input; and
- controlling the presentation of the information on the VR enabled display unit based on the view time event.

10. A virtual reality (VR) device for displaying information, the VR device comprising:
- at least one sensor unit to detect at least one event;
- a VR enabled display unit;
- at least one processor; and
- a memory configured to store instructions which, when executed, cause the at least one processor to:
  - display at least one VR content on a screen of the VR enabled display unit,
  - detect the at least one event in a real world environment,
  - determine information corresponding to the detected at least one event through the at least one sensor unit,
  - divide, if the detected at least one event satisfies at least one predetermined rule, the screen of the VR enabled display unit into at least two display areas including a first display area and a second display area,
  - display continuously the at least one VR content on the first display area, and
  - display the determined information on the second display area,
- wherein the information includes at least one of a real time video depicting the real world environment and a real time image depicting the real world environment and is captured by the at least one sensor unit of the VR device.

11. The VR device of claim 10, wherein the at least one sensor unit comprises an eye-tracing sensor, a facial expression sensor, a touch panel, a vibrator, an optics module, an accelerometer, a gyroscope, a geomagnetic sensor, a magnetic sensor, a proximity sensor, a gesture sensor, a grip sensor, a biometric sensor, an access sensor, a camera module, an audio module, an atmospheric pressure sensor, a red, green, blue (RGB) sensor, a temperature sensor, a humidity sensor, a light sensor, a physiological sensor, a location/position detection sensor, or an ultraviolet (UV) sensor.

12. The VR device of claim 10, wherein the at least one event corresponds to a change within a predefined area in the real world environment surrounding the VR device and includes at least one of:
- a risk or a threat to a user of the VR device,
- a physiological state of the user of the VR device,
- a gesture input,
- an audio input,
- an eye gaze movement,
- a facial expression of a person proximate to the VR device,
- a movement of the VR device,
- a proximity of a person to the VR device,
- a proximity of an object to the VR device, or
- a sudden movement in proximity to the VR device.

13. The VR device of claim 10, wherein the at least one predetermined rule includes:
- the at least one event or at least one parameter associated with the at least one event is predefined in a memory;
- the at least one event or at least one parameter associated with the at least one event is specified by a user;
- at least one parameter associated with the event has a value higher than a predefined threshold value; and
- at least one parameter associated with the event has a constant value for a predefined threshold value of time.

14. The VR device of claim 10, wherein the determined information is displayed on the screen of the VR enabled display unit in one of: an overlay mode, a picture-in-picture mode, a split screen mode, a split view mode, and a sectional view mode.

15. The VR device of claim 10 wherein the determined information is displayed based on the at least one predetermined rule.

16. The VR device of claim 10, wherein the instructions further cause the at least one processor to:
- determine a direction of the detected at least one event;
- determine a position on the VR enabled display unit based on the determined direction;
- select the first display area on the display based on the determined position; and
- present the information on the first display area of the screen of the VR enabled display unit.

17. The VR device of claim 10, wherein the instructions further cause the at least one processor to:
- determine at least one of a type of the detected at least one event, a priority level of the detected at least one event, or an application rendering the at least one VR content based on the at least one predetermined rule;

select the second display area on the display based on the determined type; and present the information at the second display area of the screen of the VR enabled display unit.

18. The VR device of claim 10, wherein the instructions further cause the at least one processor to:
   detect a view-time event, the view-time event being one of:
      expiry of a predetermined time from a time of capturing of the event;
      a movement of the VR device from a first position to a second position subsequent to the capturing of the event,
      a reception of a predefined gesture input, or
      a reception of a predefined audio input; and
   control the presentation of the information on the VR enabled display unit based on the view-time event.

* * * * *